US011596683B2

(12) United States Patent
Heaton et al.

(10) Patent No.: US 11,596,683 B2
(45) Date of Patent: Mar. 7, 2023

(54) ENGINEERED INFLUENZA POLYNUCLEOTIDES, VIRUSES, VACCINES AND METHODS OF MAKING AND USING THE SAME

(71) Applicant: Duke University, Durham, NC (US)

(72) Inventors: Nicholas Scott Heaton, Durham, NC (US); Alfred Theodore Harding, Durham, NC (US); Brook Elizabeth Heaton, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 16/317,427

(22) PCT Filed: Jul. 12, 2017

(86) PCT No.: PCT/US2017/041737
§ 371 (c)(1),
(2) Date: Jan. 11, 2019

(87) PCT Pub. No.: WO2018/013704
PCT Pub. Date: Jan. 18, 2018

(65) Prior Publication Data
US 2019/0224305 A1 Jul. 25, 2019

Related U.S. Application Data

(60) Provisional application No. 62/505,256, filed on May 12, 2017, provisional application No. 62/361,131, filed on Jul. 12, 2016.

(51) Int. Cl.
*C07H 21/02* (2006.01)
*A61K 39/145* (2006.01)
(Continued)

(52) U.S. Cl.
CPC ............ *A61K 39/145* (2013.01); *A61K 39/12* (2013.01); *A61K 39/39* (2013.01); *A61P 31/16* (2018.01); *C07K 14/00* (2013.01); *C07K 14/005* (2013.01); *C07K 14/11* (2013.01); *C12N 7/00* (2013.01); *C12N 9/2402* (2013.01); *C12N 15/86* (2013.01); *A61K 2039/5252* (2013.01); *C07K 2319/42* (2013.01); *C07K 2319/50* (2013.01);
(Continued)

(58) Field of Classification Search
None
See application file for complete search history.

(56) References Cited

U.S. PATENT DOCUMENTS

2008/0069821 A1* 3/2008 Yang .................... A61K 39/145
424/139.1

OTHER PUBLICATIONS

Szymczak-Workman et al., "Design and construction of 2A peptide-linked multicistronic vectors," Cold Spring Harb Protoc 2012(2): 199-204 (Year: 2012).*

(Continued)

*Primary Examiner* — M Franco G Salvoza
(74) *Attorney, Agent, or Firm* — Quarles & Brady LLP

(57) ABSTRACT

Engineered Influenza polynucleotides, viruses, vaccines, and methods of making and using the same are provided. More specifically, the present inventors have developed replication competent engineered influenza viruses having, for example, a modified segment 4 and/or segment 6 that include at least one additional polynucleotide encoding a heterologous polypeptide.

15 Claims, 56 Drawing Sheets
(52 of 56 Drawing Sheet(s) Filed in Color)
Specification includes a Sequence Listing.

(51) Int. Cl.

| | | |
|---|---|---|
| A61P 31/16 | (2006.01) | |
| C07K 14/11 | (2006.01) | |
| C07K 14/005 | (2006.01) | |
| C07K 14/00 | (2006.01) | |
| A61K 39/12 | (2006.01) | |
| C12N 7/00 | (2006.01) | |
| C12N 15/86 | (2006.01) | |
| A61K 39/39 | (2006.01) | |
| C12N 9/24 | (2006.01) | |
| A61K 39/00 | (2006.01) | |

(52) U.S. Cl.
CPC ............... C07K 2319/60 (2013.01); C12N 2760/16121 (2013.01); C12N 2760/16122 (2013.01); C12N 2760/16134 (2013.01); C12N 2760/16143 (2013.01); C12Y 302/01018 (2013.01)

(56) References Cited

OTHER PUBLICATIONS

Breen M, et al. 2016. Replication-competent influenza A viruses expressing reporter genes. Viruses 8:E179. https://doi.org/10.3390/v8070179.

Fiege JK, et al. 2015. Investigating influenza A virus infection: tools to track infection and limit tropism. J Virol 89:6167-6170. https://doi.org/10.1128/JVI.00462-15.

Fodor, E., et al. "Rescue of influenza A virus from recombinant DNA." Journal of virology 73.11 (1999): 9679-9682.

Gao, Q., et al. 2008. A seven-segmented influenza A virus expressing the influenza C virus glycoprotein HEF. J Virol 82:6419-6426. https://doi.org/10.1128/JVI.00514-08.

Gao, Q., et al. 2012. The influenza A virus PB2, PA, NP, and M segments play a pivotal role during genome packaging. J Virol 86:7043-7051. https://doi.org/10.1128/JVI.00662-12.

Gao, Q., et al. "A nine-segment influenza a virus carrying subtype H1 and H3 hemagglutinins." Journal of virology 84.16 (2010): 8062-8071.

Harding, A. T., et al. "Rationally designed influenza virus vaccines that are antigenically stable during growth in eggs." MBio 8.3 (2017): e00669-17.

Harvey, R., et al. "A promoter mutation in the haemagglutinin segment of influenza A virus generates an effective candidate live attenuated vaccine." Influenza and other respiratory viruses 8.6 (2014): 605-612.

Heaton NS, et al. 2013. In vivo bioluminescent imaging of influenza A virus infection and characterization of novel cross protective monoclonal antibodies. J Virol 87: 8272-8281. https://doi.org/10.1128/JVI.00969-13.

Heaton NS, et al. 2016. Targeting viral proteostasis limits influenza virus, HIV, and dengue virus infection. Immunity 44:46-58. https://doi.org/10.1016/j.immuni.2015.12.017.

Hoffmann, E., et al. "A DNA transfection system for generation of influenza A virus from eight plasmids." Proceedings of the National Academy of Sciences 97.11 (2000): 6108-6113.

International Searching Authority, International Search Report and Written Opinion for application PCT/US2017/041737, dated Sep. 22, 2017.

Kim, JH, et al. "High cleavage efficiency of a 2A peptide derived from porcine teschovirus-1 in human cell lines, zebrafish and mice." PloS one 6.4 (2011).

Li, F. et al. Generation of replication-competent recombinant influenza A viruses carrying a reporter gene harbored in the neuraminidase segment. J Virol 84, 12075-12081, doi:10.1128/JVI.00046-10 (2010).

Manicassamy, B., et al. "Analysis of in vivo dynamics of influenza virus infection in mice using a GFP reporter virus." Proceedings of the National Academy of Sciences 107.25 (2010): 11531-11536.

Masic, A., et al. "An eight-segment swine influenza virus harboring H1 and H3 hemagglutinins is attenuated and protective against H1N1 and H3N2 subtypes in pigs." Journal of virology 87.18 (2013): 10114-10125.

Pan W, et al. 2013. Visualizing influenza virus infection in living mice. Nat Commun 4:2369. https://doi.org/10.1038/ncomms3369.

Pena L, et al. 2013. Influenza viruses with rearranged genomes as live-attenuated vaccines. J Virol 87:5118-5127. https://doi.org/10.1128/JVI.02490-12.

Sekikawa, K. et al. Defects in functional expression of an influenza virus hemagglutinin lacking the signal peptide sequences. Proc Natl Acad Sci US A 80, 3563-3567 (1983).

Soema PC, et al. 2015. Current and next generation influenza vaccines: formulation and production strategies. Eur J Pharm Biopharm 94:251-263. https://doi.org/10.1016/j.ejpb.2015.05.023.

Spronken, M. I., et al. "Optimisations and challenges involved in the creation of various bioluminescent and fluorescent influenza A virus strains for in vitro and in vivo applications." PLoS One 10.8 (2015).

\* cited by examiner

Figures 1A-1C
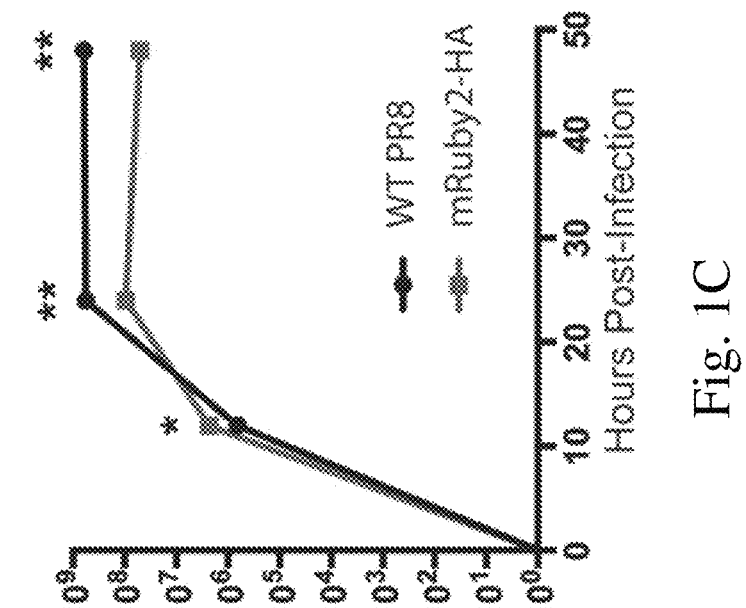
Fig. 1A
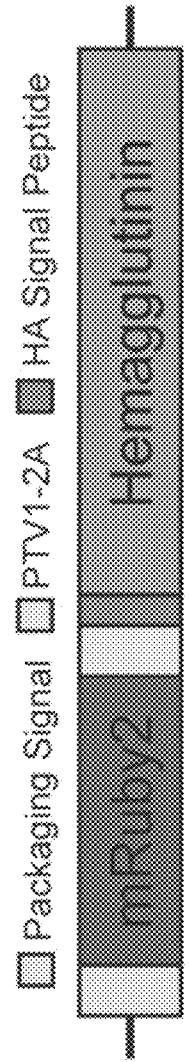
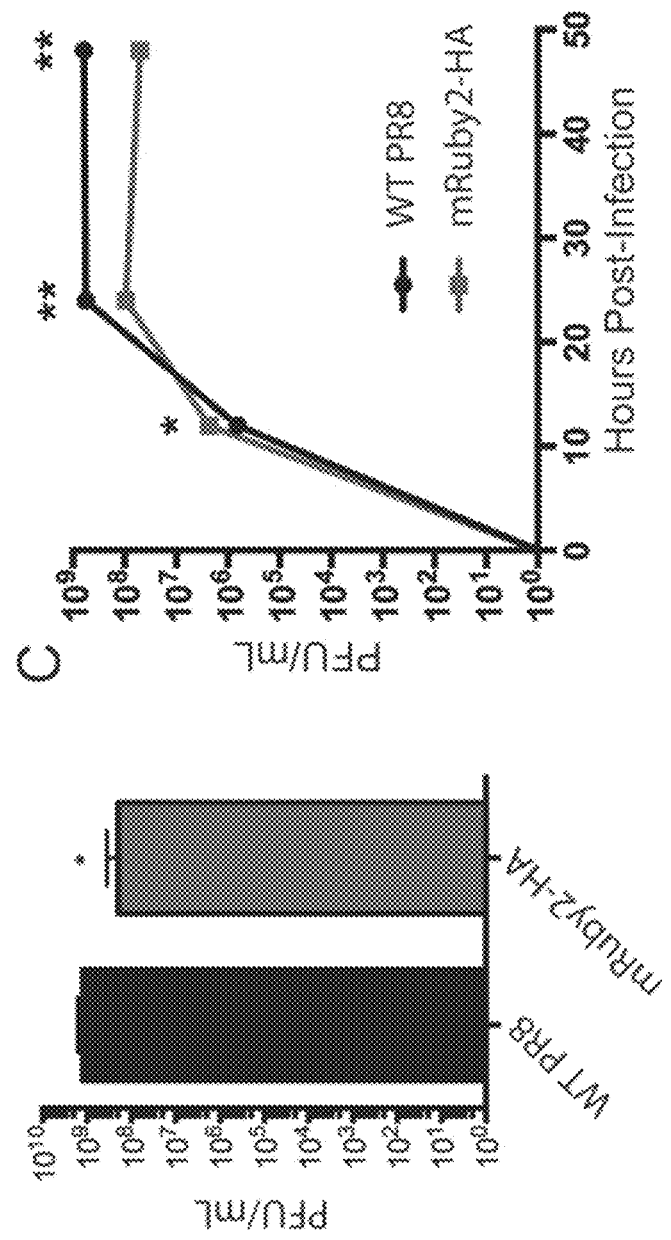
Fig. 1B
Fig. 1C

Figures 3A-3C
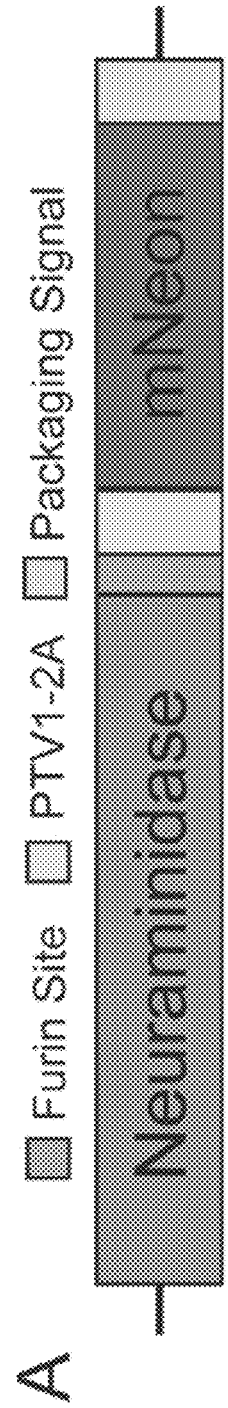
Fig. 3A
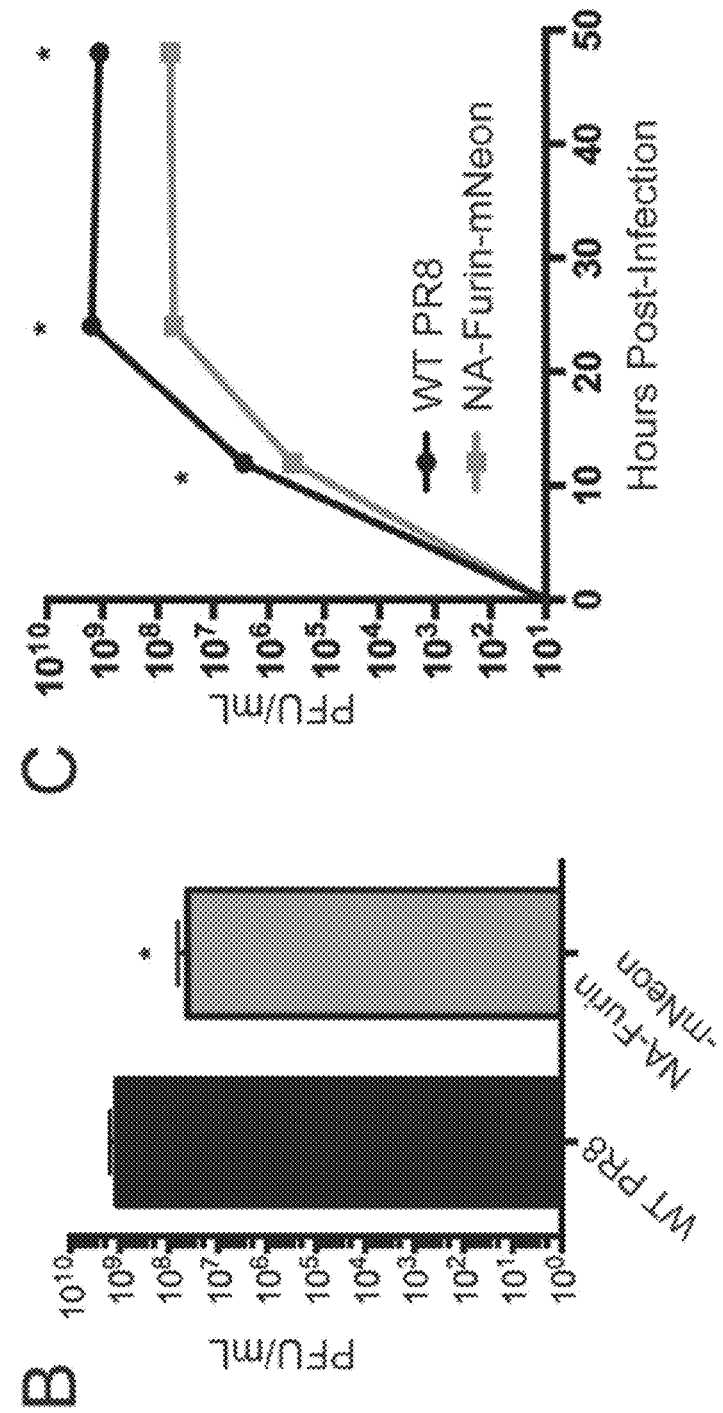
Fig. 3B
Fig. 3C

Figures 3D-3E
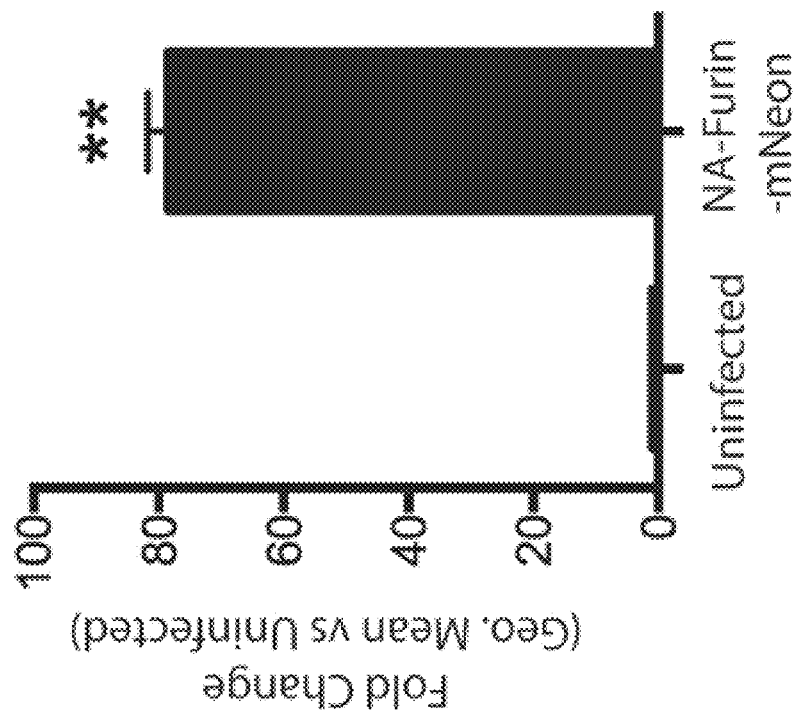
Fig. 3D
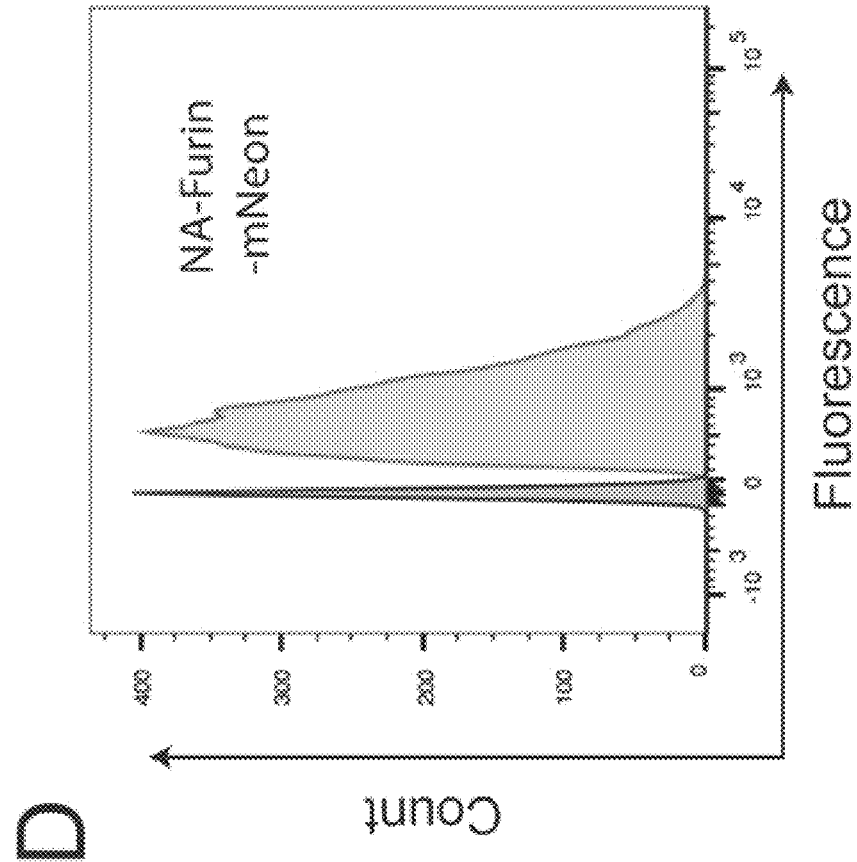
Fig. 3E

Figure 4

SEQ ID NOs: 3 (Furin site), 4 (PTV1-2A), 56 (

Figures 6C-6E
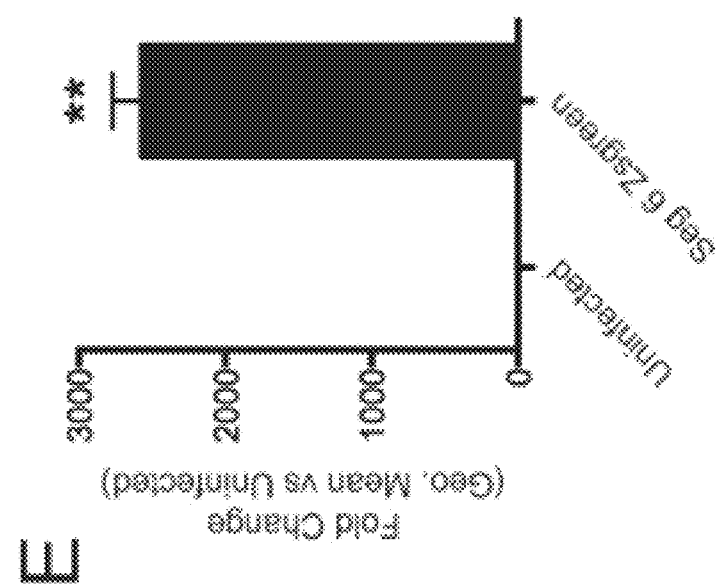
Fig. 6E
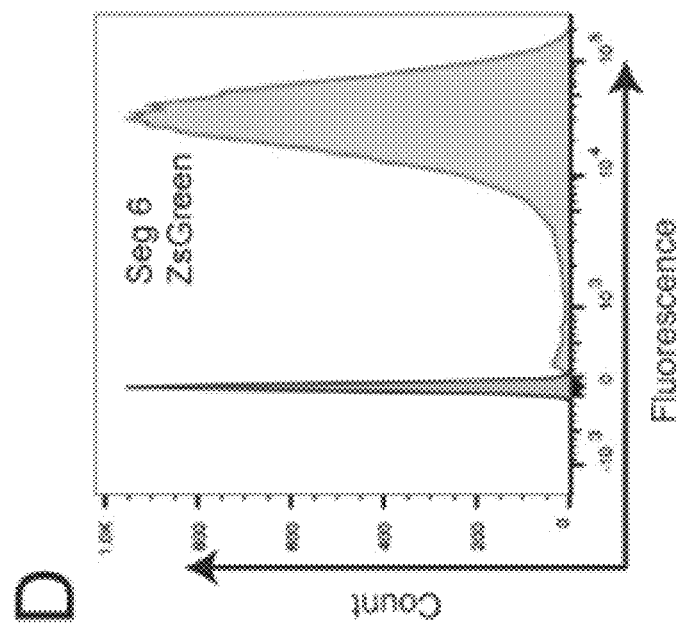
Fig. 6D
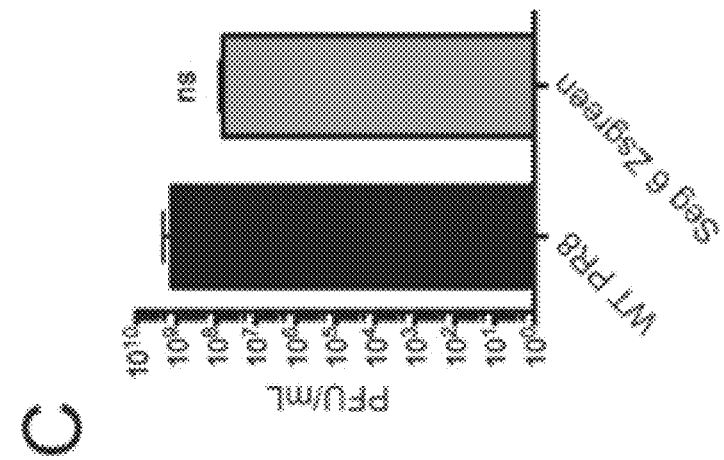
Fig. 6C

Figures 6F-6G
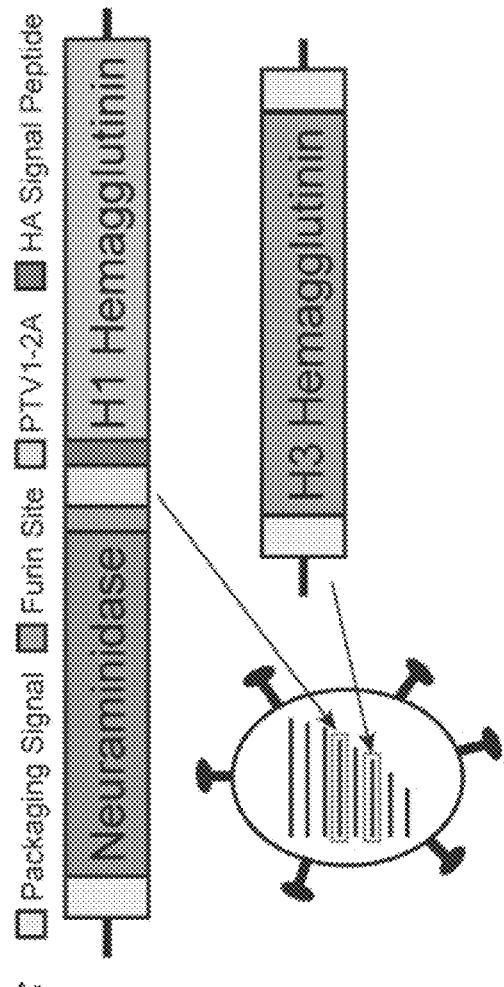
Fig. 6F
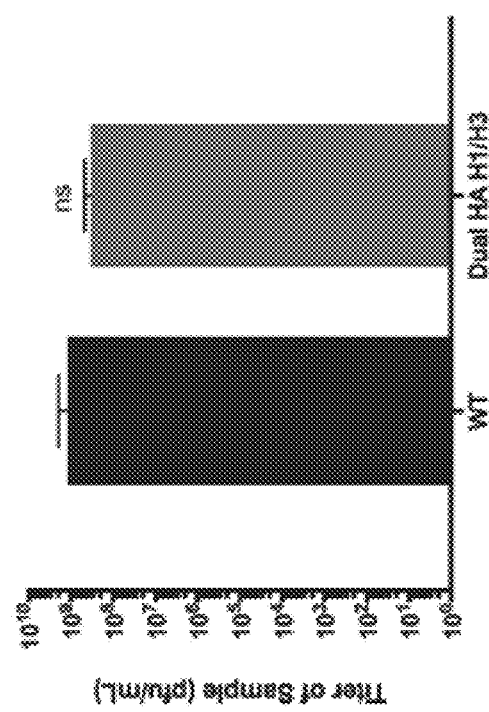
Fig. 6G

Figures 6H-6I
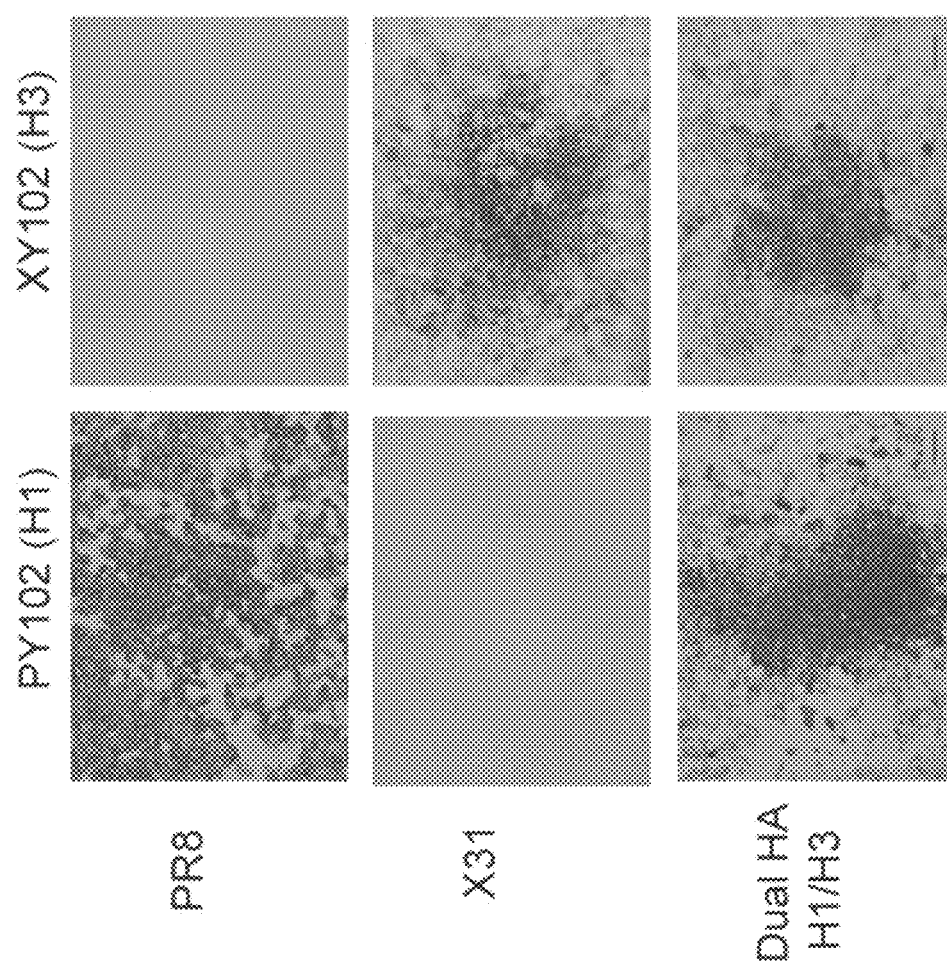
Fig. 6I
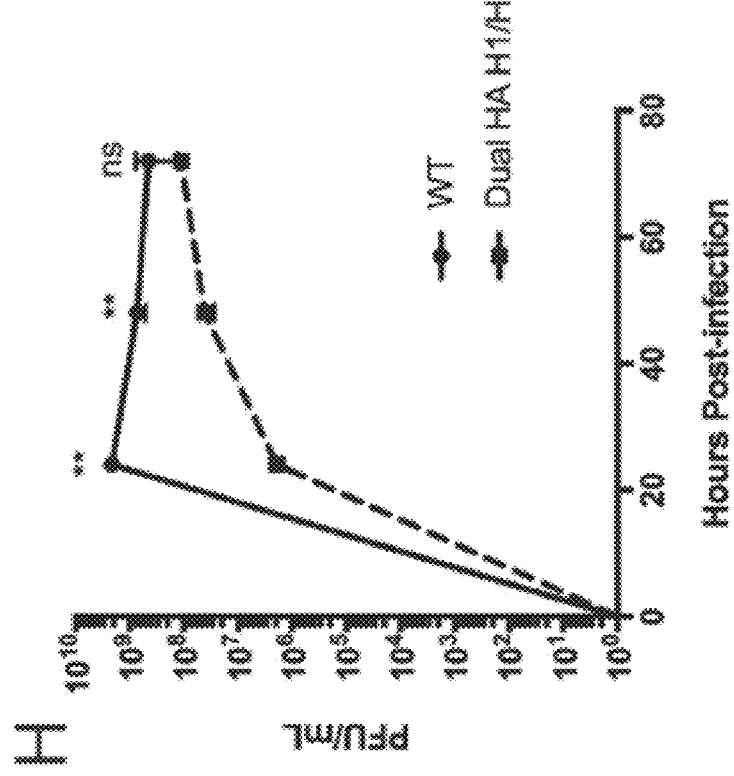
Fig. 6H

Figure 9E-9H
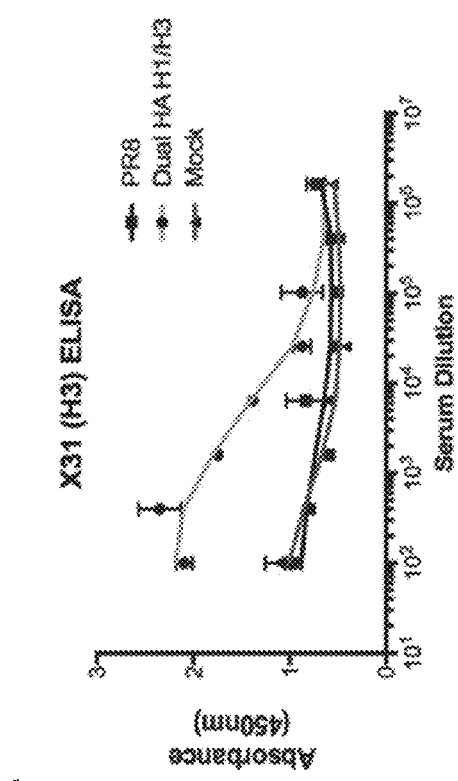
Fig. 9E
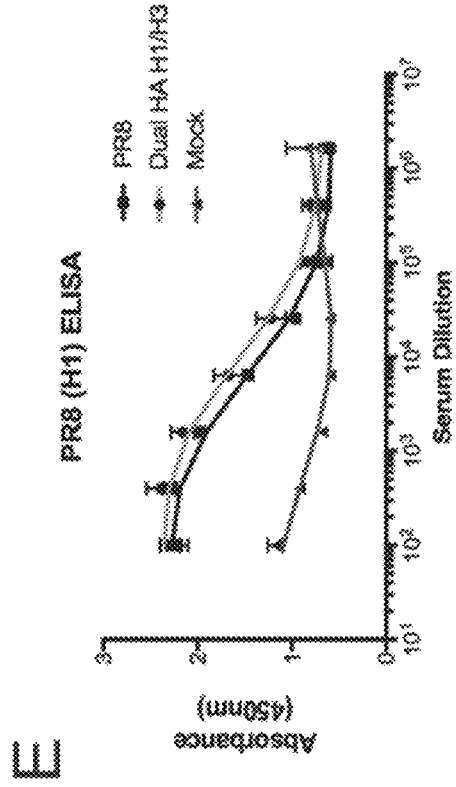
Fig. 9G
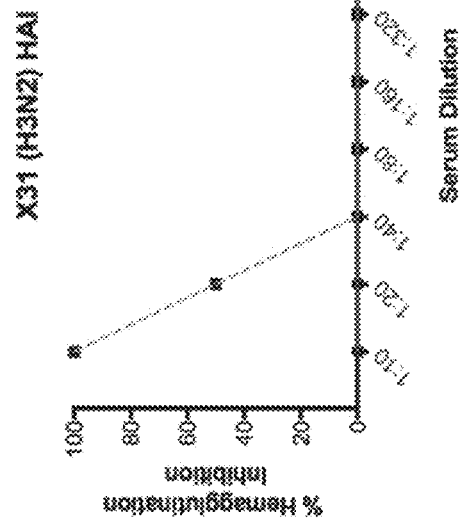
Fig. 9F
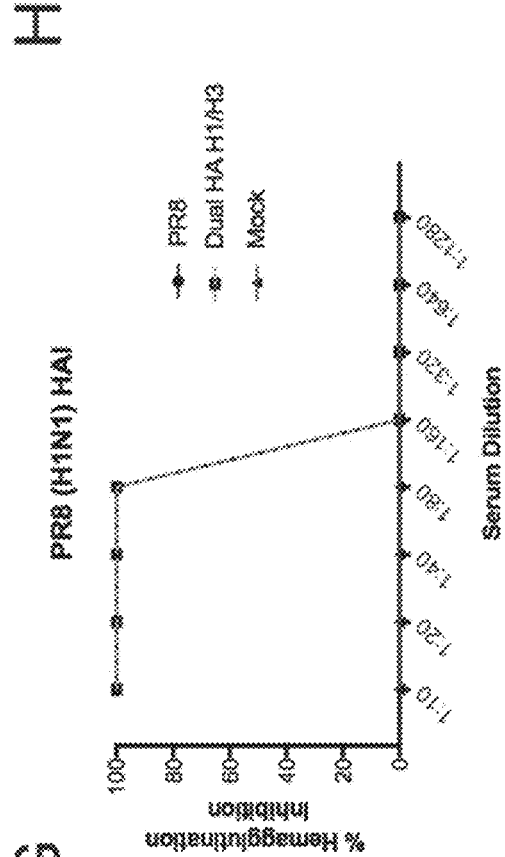
Fig. 9H Figure 9I-9J
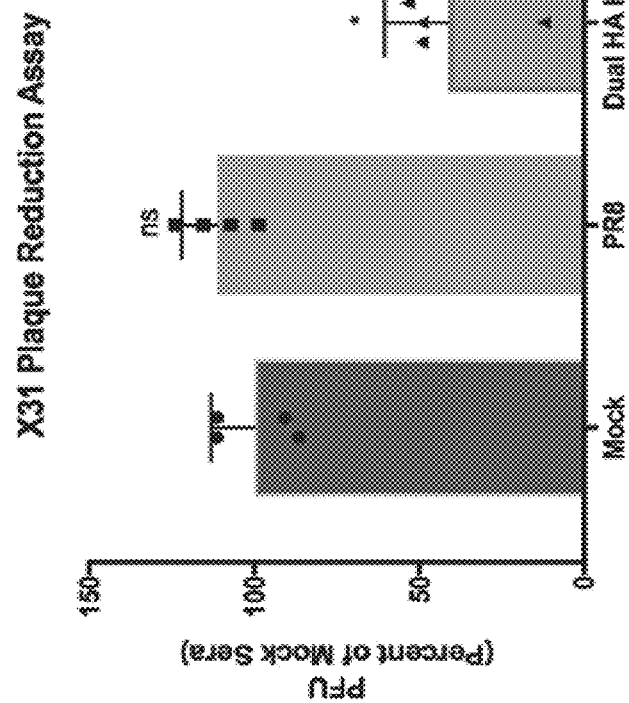
Fig. 9I
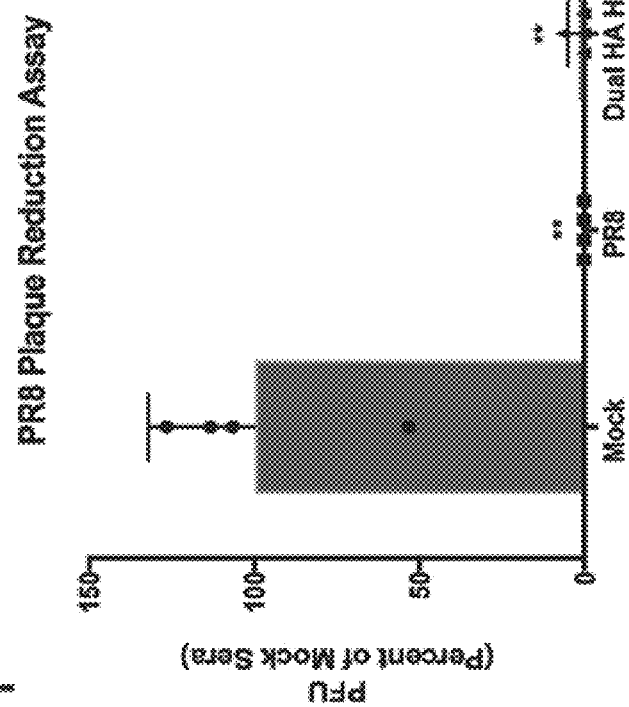
Fig. 9J Figure 10A-10B
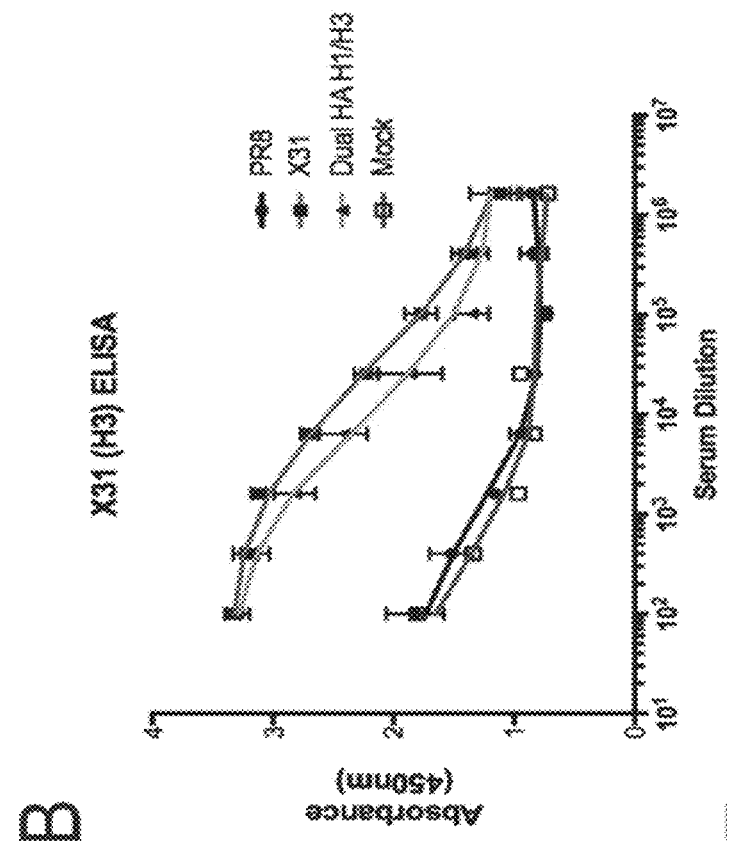
Fig. 10A
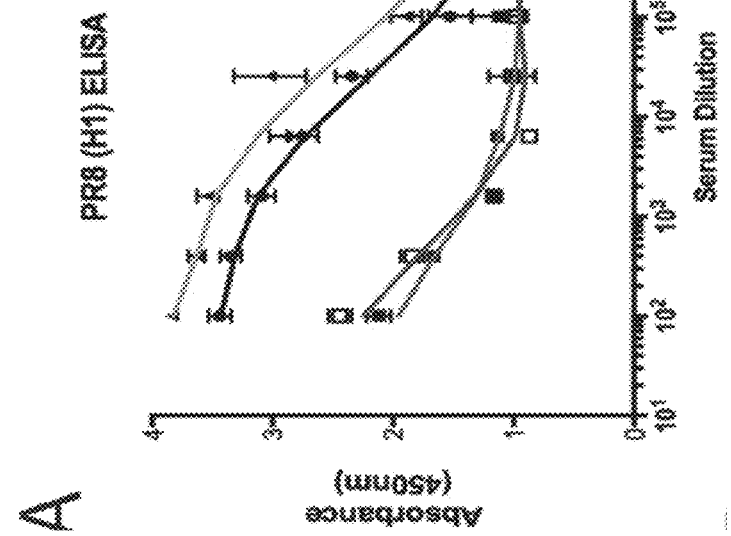
Fig. 10B Figure 10E-10F
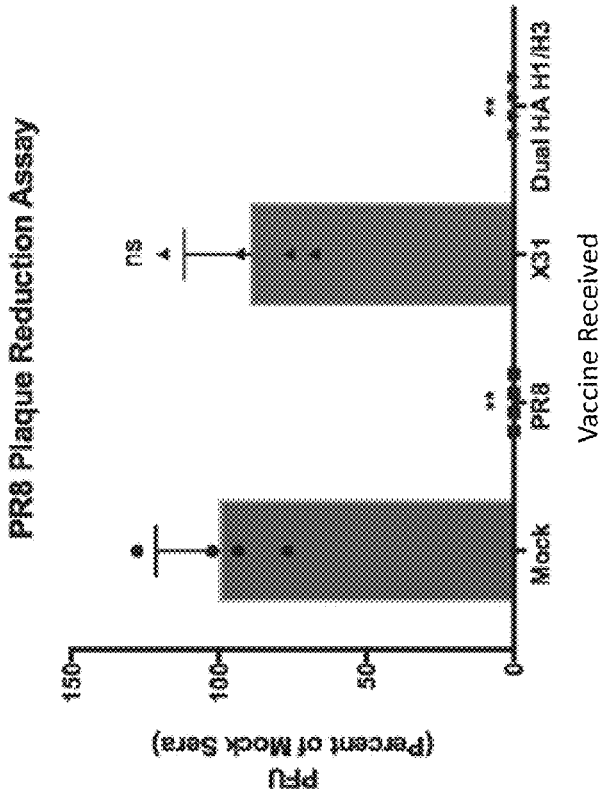
Fig. 10F
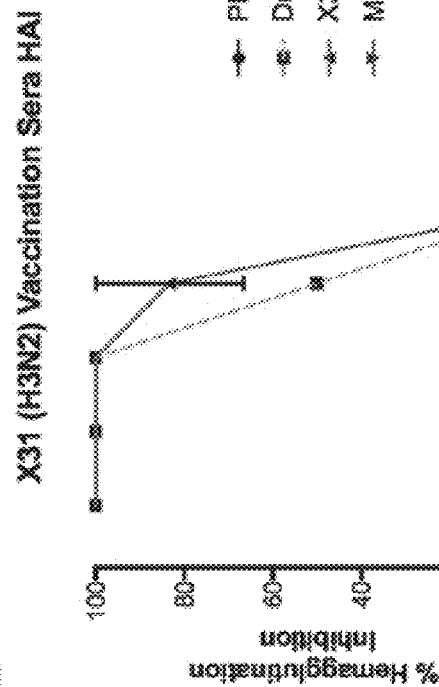
Fig. 10E Figure 10G-10H
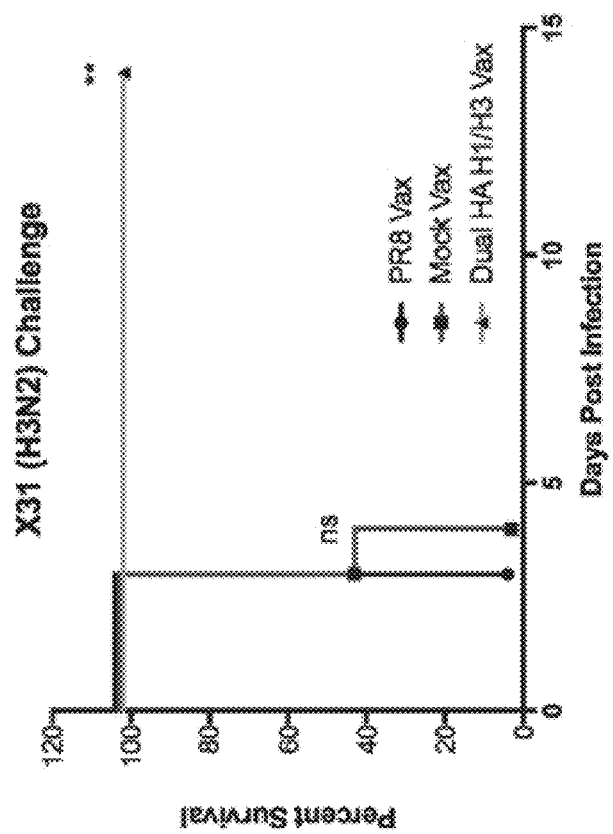
Fig. 10H
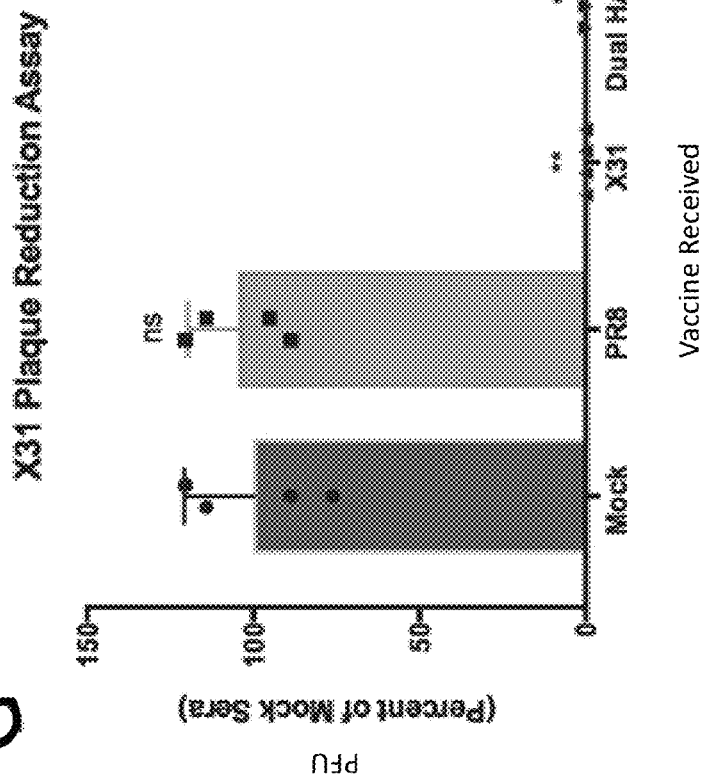
Fig. 10G

Figure 11
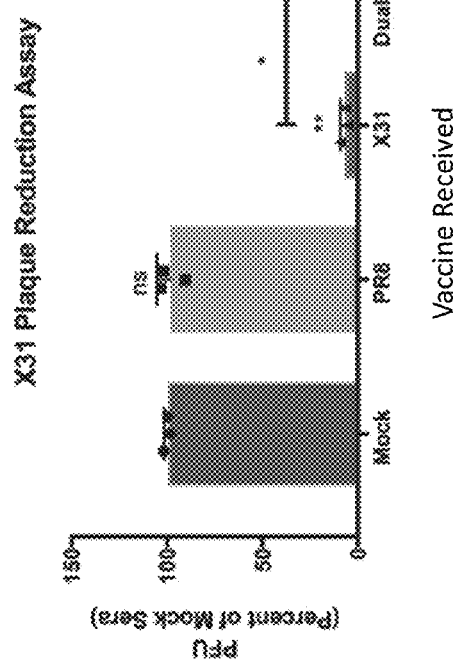
Fig. 11B
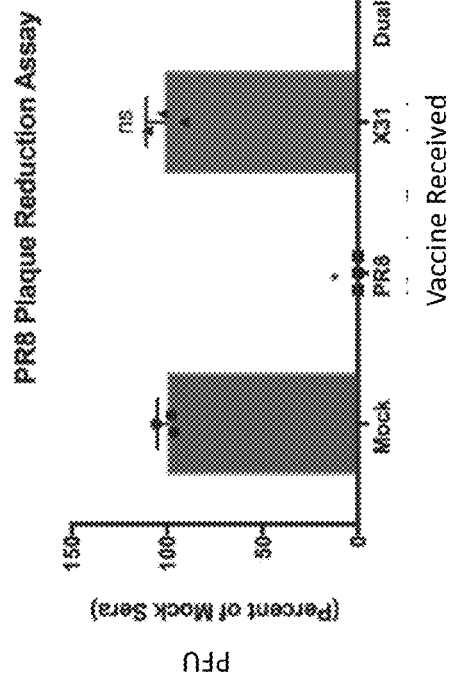
Fig. 11A

Figures 12A-12D
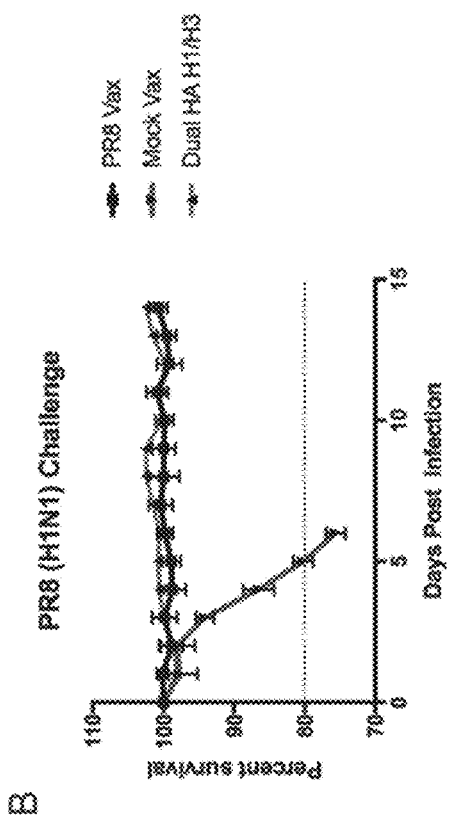
Fig. 12A
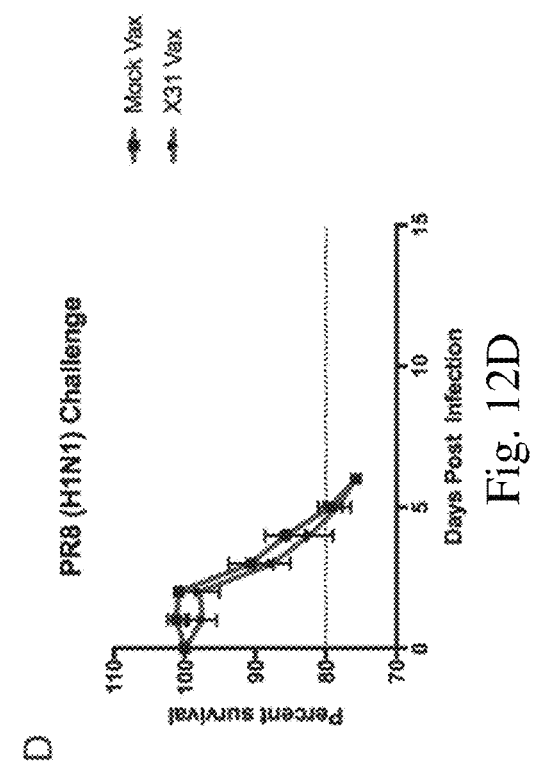
Fig. 12B
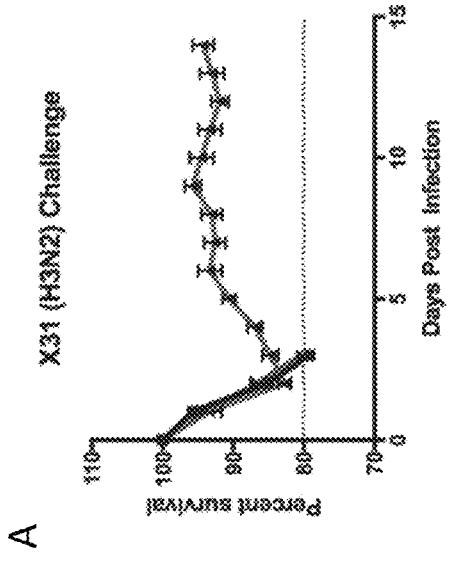
Fig. 12C
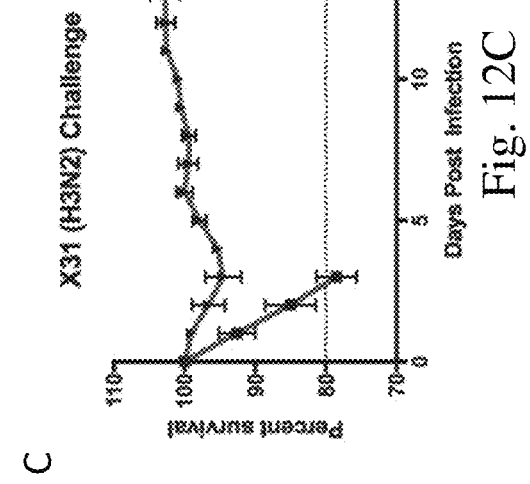
Fig. 12D Figures 12E-12F
Fig. 12F
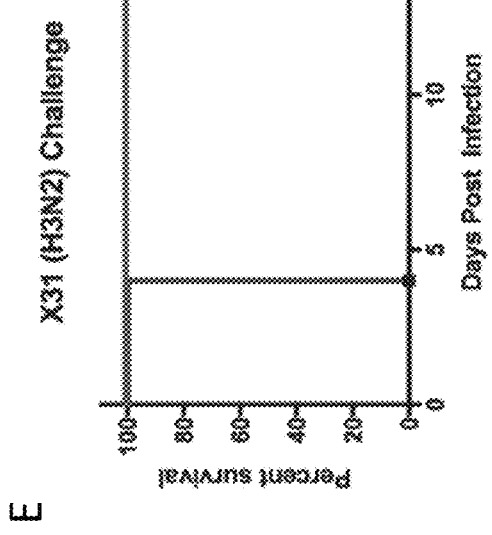
Fig. 12E

Figure 13F

| Origin of HA Sequence | Amino Acid at Position Indicated for HA1 | | | | | | | HA2 |
|---|---|---|---|---|---|---|---|---|
| | 128 | 183 | 186 | 188 | 219 | 226 | 309 | 150 |
| Parental Fujian NCBI: CY112933.1 | T | L | G | D | S | V | V | D |
| Lu et al. 2005 (Ref 9) | T or A | L | V | | F or Y | I | | G |
| Nicolson et al. 2005 (Ref 33) | | L | | Y | | | | |
| Widjaja et al. 2006 (Ref 10) | | | V | | F | I | I | |
| A/Fujian/02-PR8 Dual HA | T | L | G | D | S | V | V | D |

Figure 14
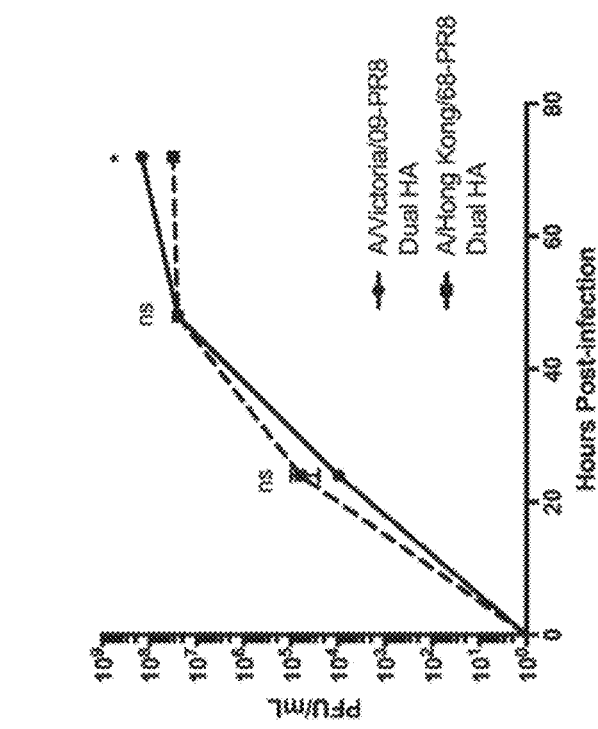
Fig. 14A
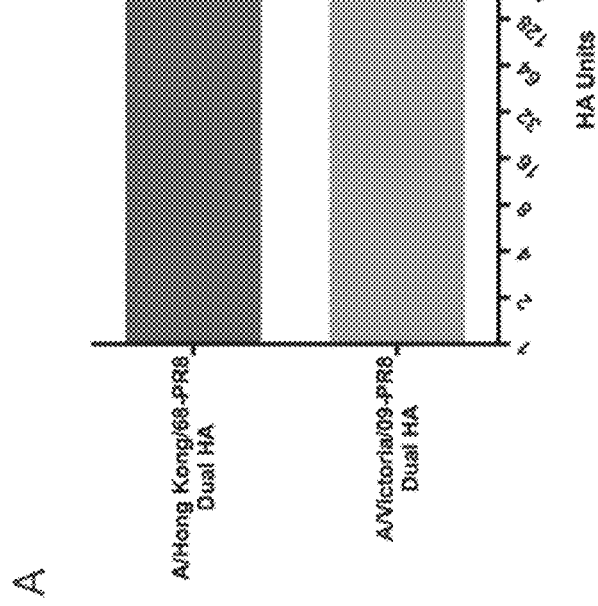
Fig. 14B

Figure 15
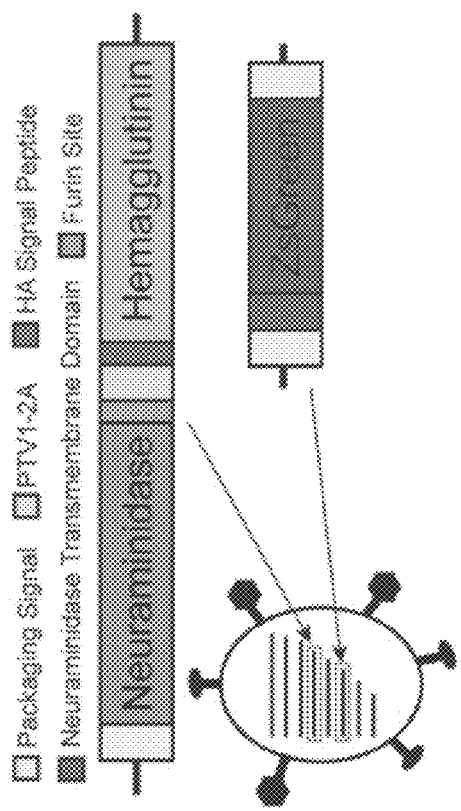
Fig. 15A
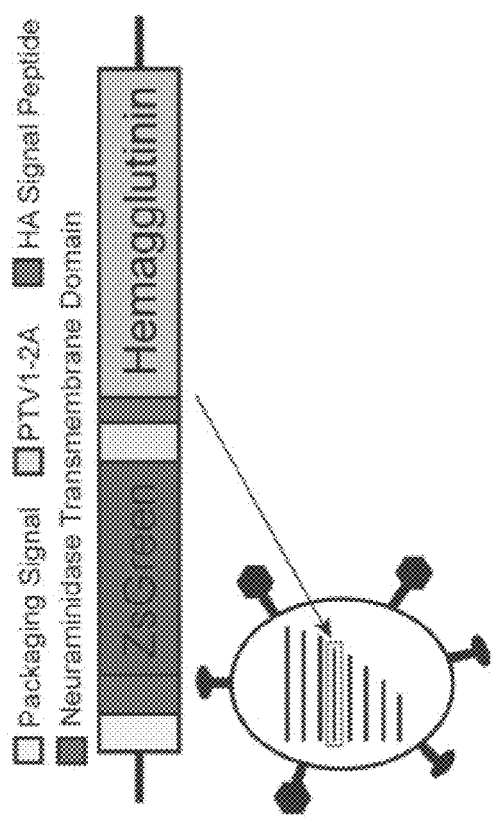
Fig. 15B

Figure 15C and 15D
Fig. 15C
Fig. 15D
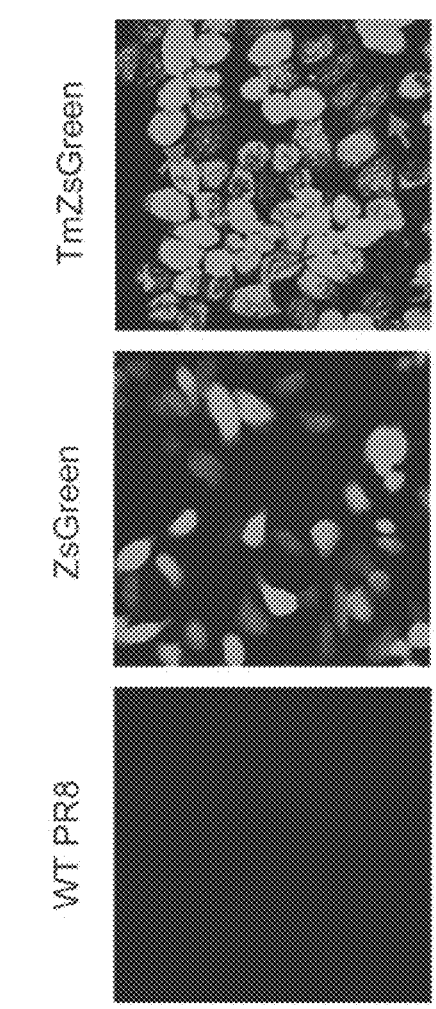
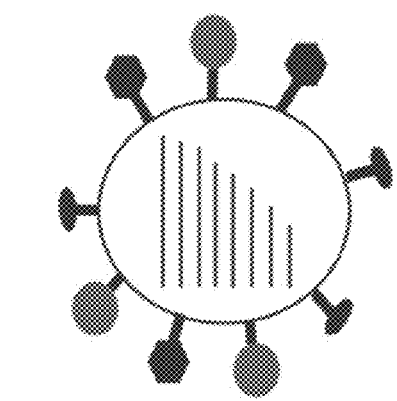

Figure 16
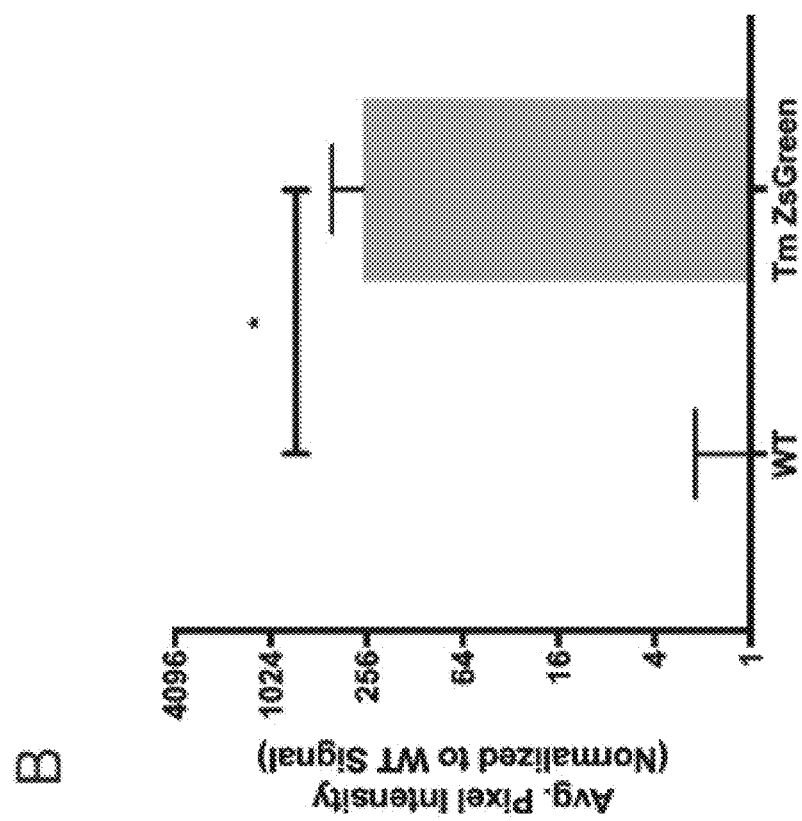
Fig. 16B
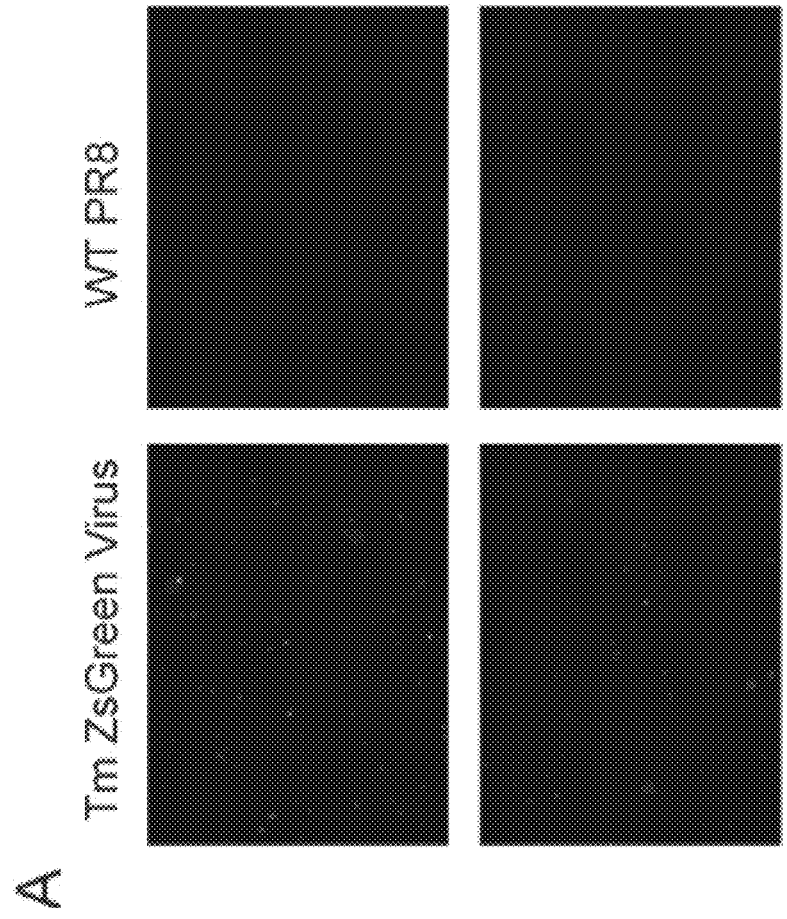
Fig. 16A

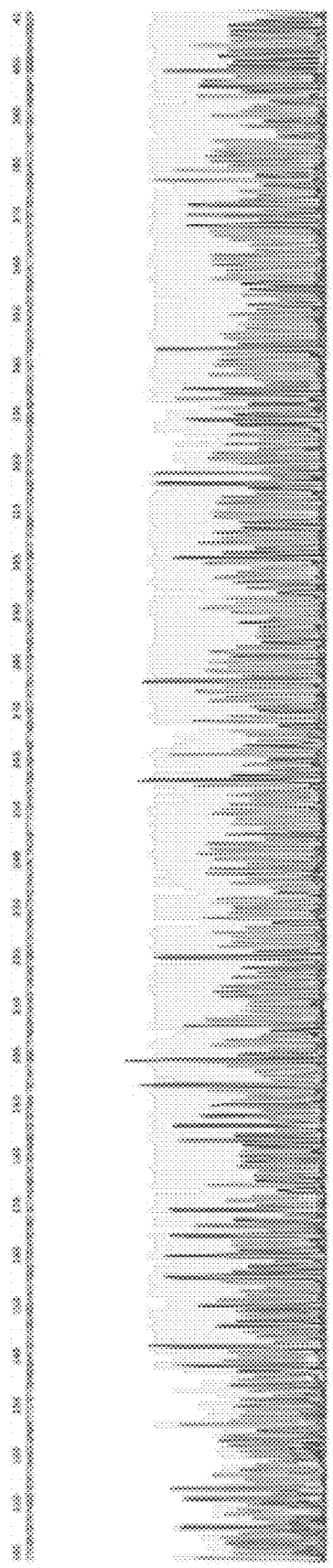
Fig. 16D: SEQ ID NO: 55

Figure 17 – SEQ ID NO: 44

```
agcgaaagcaggggtttaaaatgaatccaaatcagaaaataacaaccattgatcatctgtcgtagtcgaactaattgcctaatat
tgcaaatgggaaatatatcatcaatatggattgccattcaattcaaacggaagtcataccgaaacaatcatgcaacaaacatc
attacctataaaaatagcaccctggtaaaggacacacaacttcagtagatattaaccggcaattcatctcttgtccatcgtgggtggctat
atacagcccaaagacaatagcctaagcaatgttccaaaggagcgctgttttgtcatcaaagagccctttatttcatgttctcacttgaagtgc
aggaccttttctgaccaagtcgtccttactgaataacaagcattcaaatggactgttaagaacagaagccttatagccttaatga
gctgccctgtcgtgaagtccgtccccgtacaattcaagatttcatcggttcttcgtcgcagtgcatgtcatgtgtcatggctgg
ctaacaatcggaattcagtcagtcgaataatgagcatgctgttatttaaatcaacatgtctataaccatgaaaaacatgaaagttgaag
gaagaaaatattgaaggaacacaagagtcgaagtgcctgtaaatgttcatgtttactataatgactcattctcactatgaggaatgttcct
gcctgtacaaaatttcaagatgcaaagtgatgtgtgtccagagacaactgccatggttccgaaccgatggaaccgatgatgatggtt
gttacctgatccggcaaagttgatggggttttcggtgccagagacaacagccgctgtgtggctgagtgttcagttatctg
attatcaaatgagatacatctgcagtgggttgtcatatggatttcatatgtagtaataggttgtttggatagagcaacagtccagaacaagg
atggacaacgaagtaaggaattttcatatgacatggacagagctagcactgaagtcagttcctcttgttggagccgtactattcaa
tttggagattggaatccaatcgatatggaacatcctgactaacaaggctagaggcgtatgaagccgtccttcgtcgattgaattaatcaggagagcgac
gatagcgacattgagttcgttcaacatcctgacggtcaacatggcgaaggactatgaagccgtcttctcggttgaattaatcagaaggacgac
ctaagaaaaacactcggactagtgcgaccgcagcgtttttttgccgtgaatagatagtaCacCgtagaCtcgAGCtgccGgaTg
gCgcCgaACtAccGttTTCTatCgaTaaAaggaaGggagaggGGAAGGGAGCAAAGGAGGACAACATGGCTA
AAGGAGATGTGGCCACTCATGAGCTTCATATATTCGGTTCATTAAGGAGAGATATTCAACAAAGGAGACCTCCA
GCCTACCTGCCACTCATGAGCTTCATATATTCGGTTCATTAAGGAGAGATATTCAACAAAGGAGACCTCCA
AAGGGACAGGGCAATCCAAATGATGATGCAAGGATATACCGAGGGTCATCAATACCTACCTTCATGAGA
ATTTTCCCCTGGATCTTGGTCCCACACATGGTGGACGGGAGTGGATACGGAGGGCTGAGAACGACAAGCTGACT
ATGTCACCGTTTCAAGCAGCAAGGGTTCCCAGCAGCTATCCAAATGACAAAAACAATATTTCCACTTCAAGTGGAGCAGCA
GGTGCAGGAGTAAAAGAGACGTATCCAAATGACAAAAACAAGGACTACACAGCAGGTTAAACATTCAAAACCGAG
ACTGGTAATGGGAAGAGATAATCAACCATGTCTACACGAAGGGCCAAGGCCAAGGCCAAGGCTG
CAAACTATCTCAAGAATCAAGAATTTAAGGAATGGCAAAAGGCCCATTCAGGAAAACAGAGCTTAAACATTCAAAACCGAG
TTAAATTTAAGGAATGGCAAAAGGCATTTACGGATGTGATGGATGAACTGTATAAAgaag
acgactgTAGccgtgcttctgagttgaattaatcggttgaattgcttgaattggagcagagcatttctttt
tgtggcgtgaatgtgatctgtaggtgtgattgtcttggccagacgtgctgcttccattcagcattgacaagtgctgttcaaaaactc
cttgttctact
```

_____ UTR
Bold - Mutated PS
_Italics - PTV-2A Site_
Underline - ORF NA
░░░ - highlight - Furin Site
Bold Underline - ORF mNeon
_Italics_ Bold - KDEL Seq.

Figure 18 – SEQ ID NO: 45

Legend:
- UTR
- Bold – HA Signal Peptide sequence
- *Italics* – PTV-2A Site
- Underline – ORF HA
- Bold Underline – Kozak Sequence
- *Bold Italics* – ORF mRuby2 agcaaaagcagggggaaataaaaacaaccaaaTtgaaggcaaactactggtctgttaagtcattgagctgcagttgcagacacaattgta
taggccaccATGGTATCCATCAGTTAATGCACAGGGAGGAACTTATTAAAGAAATATGGCGCATGGAAAGTGGTCATGGAGGGTCT
GTTAATGGTCATCAGTTAATGCACAGGGAGGAACTTATTAAAGAAATATGGCGCATGGAAAGTGGTCATGGAGGGTCT
TAAAAGTGATTGAAGGGGCCCACTGCCCTTCGATTCGACATCCTTGGAACATCCTTATGGATCGAGGA
CATTTATTAAATACCCGAAAGGAATACCAGACTTCTTCAAACAGTCTTTCCCGAGGATCTCACCTGGGAGAGAG
TAACTAGAATACGAGGATGGGGGGGTCAATTCCCCTCAATTGTCCTGATGCAGAGAAACTAAAGGATGGAAC
TCATGTCCAAGTGAGGGGGGTCAATTTCCCCTCAATTGTCCTGATGCAGAGAAACTAAAGGATGGAAC
CCAATACTGAAATGATGATGTACCCGTCTCTTGTCACAACATATAGATCTAAAAAAACAGTTGAAATATCAAAATGCCAGG
GGAGGACACCTGTCATGCTCCTTGTCACAACATATAGATCTAAAAAAACAGTTGAAATATCAAAATGCCAGG
GATCCATGCCGTTGATCACAGGCTAGAACACGGAAAGATTGGAAGAGAGCGACAAGAAATGTTTGTAGTGCAGCGGGAA
CATGCCGTAGCCAAGTTTGCTGGATTGGGGAGGGAGGAAGAAAATCCTGGGCCTatgaaAgcGaaTTtGTtAgtTTtACtGTCCgcG
CAGTCCCTCAAACAGGCCGGAGACGTGGAAGAACGTGGAAGAAAATCCTGGGCCTatgaaAgcGaaTTtGTtAgtTTtACtGTCCgcG
*TtGgcGgcCgcGgaCgagaaCgagacaataatgtatatggctaacattaacgcactgttgacacgtacttcggagaagatgtaact*
*gacacactctgttaactgctcgaaaccagaatgcgacccagtcctcagtggatcagtgcttccagtggatcatgtgattcatatatcgcc*
*ggatggcctctggaacccagatgctactggtcggaggctgaggagcaatgcccatgcccatgtcccaagagagaagtcatgcc*
*caaccaccaaacgaagtaaagcagcaatgtcccatgagggaagaagtccttgtactgtggggtattcatcaccgcctaacagtaaggaacaacag*
*aatCtctatcagaatgaaaatgcttatgtctgtagtacttcaaattaacaggagatttacccgaaatagcgaaaggataaaga*
*tcaagctgggagaggtagaactattactggactttgtaaaaccggagcaacataatattgaaagcaaatgaaatctaatagcagcatatgtctt*
*tcgcactgtagtagagcttggtcgcatcatccctcaaacgcatcaatgctcatgagttgtaacagaagtgtcaaatcagtccgagctataac*
*aagcagtcccttaccagatatacaccagtctattgagccgtgatgatggccaaatctttccggttcaaacaagagatgaagttacaggactaagga*
*acactccgtcattcattcaacggatcagctgtggtgttcagcggatcaaaagaattcaaccaatctagaaaaaatgaaaaattcaacaagttgatgcatttgaac*
*tcagaatgaacaggatcgggtatgccagctgtttactgccggatcaaagaattcactggaaagattcactgaaagtcagaatgaatcagtgtaagg*
*aatgaacattcaattcagctgttgtttagttcttcagaagaatgcaaagagactcgagttaaccacggatatcaaaatgaatcaaaatgtcaatgtatggaatcagatttcgac*
*atttgacatataggaaatatcCaaatattcagaagaatcggaaagtcagaagatgatttgttttgaacaggagaagcaagggtcagaagtaagg*
*agccaattaagatcgtgccagtcaatgccaaaagaattcactgaaagttgaacacgtgaagtgaagtgaatcaatggaatcaatggaatcagattcgacg*
*cttatgattaaccaaatatccaataatcagaagaatccaggagtcagatttctcccgggaaccatcagttcccttggtcatggcttcaatgaatcttcaatggatctttcaatgaatcttca*
*atcttactactgtgcgccagttcactggtggtcttttgctccttcggtggaactcaaagcagtttgaaccagtgacatcatccaggagtcatttgaagtgaatcatcggc*
*tggatatagaatttcagaaatatgaggaaaccaccctttgtttctact*

Figure 19 – SEQ ID NO: 46 agcaaaagcaggggaaaataaaaacaaccaaaTtgaaggcaaacctactggtcctgttaagtgcacttgcagctgcagTtgcagacacaatTtgta
taggccaccatgaaCccGaaCcaAaaGatCacGacTatCggGAGCatTtgCTtAgtGgtTggGTtGatCagcctaatattgcaaatagg
gaatataatctcaatatggattagccattcaattcaaactggaagtcaaaaccatactggaatatgcaaccaaaacatcattacctataaaaatag
cacctgggtaaaggacacaacttcagtgatattaaccggcaattcatctctttgtcccatccgtgggtgggctatatacagcaaagacaatagcata
agaattggttccaaaggagacgtttttgtcataagagagccctttatttcatgttctcacttggaatgcaggaccttttttctgacccaaggtgccttac
tgaatgacaagcattcaaatgggactgttaaggacagaagcccttatagggccttaatgagctgccctgtcggtgaagctccgtccccgtacaattc
aagatttgaatcggttgcttggtcagcaagtgcatgtcatgatggcatgggctggctaacaatcggaatttcaggtccagataatggagcagtggct
gtattaaaatacaacggcataataactgaaaccataaaaagttggaggaagaaaatattgaggacacaagagtctgaatgtgcctgtgtaaatg
gttcatgttttactataatgactgatggcccgagtgatgggctggcctcgtacaaaattttcaagatcgaaaaggggaaggttactaaatcaataga
gttgaatgcacctaattctcactatgaggaatgttcctgttaccctgataccggcaaagtgatgtgtgtgtgcagagacaactggcatggttcgaacc
ggccatgggtgtctttcgatcaaaacctggattatcaaataggatacatctgcagtggggttttcggtgacaacccgcgtcccgaagatggaacagg
cagctgtggtccagtgtatgttgatggagcaaacggagtaaagggattttcatataggtatggtaatggtgtttggataggaaggaccaaaagtca
cagttccagacatgggtttgagatgatttgggatcctaatggatggacagagactgatagtaagttctctgttaggcaagatgttgtggcaatgact
gattggtcagggtatagcggaagtttcgttcaacatcctgagctaacagggctagactgtatgaggccgtgcttctgggttgaattaatcaggggac
gacctaaagaaaaaacaatctggactagtgcgagcagcatttctttttgtggcgtgaatagtgaCacCgtagaCtggAGCtggccGgaTggCgc
CgaACtAccGttTTCTatCgaTaaAggaaggagaaggGGATCTGGGGCTACCAACTTCAGTCTCCTCAAACAGGCCGGAG
ACGTGGAAGAAAATCCTGGGCCTatgaaAgcGaaTTtGTtAgtTTtACtGTCCgcGTtGgcGgcCgcGgaCgcagacacaat
atgtataggctaccatgcgaacaattcaaccgacactgttgacacagtactcgagaagaatgtgacagtgacacactctgttaacctgctcgaagaca
gccacaacggaaaactatgtagattaaaaggaatagccccactacaattggggaaatgtaacatcgccggatggctcttgggaaacccagaatgcg
acccactgcttccagtgagatcatggtcctacattgtagaaacaccaaactctgagaatggaatatgttatccaggagatttcatcgactatgaggagc
tgagggagcaattgagctcagtgtcatcattcgaaagattcgaaatatttcccaaagaaagctcatggcccaaccacaacacaaacggagtaacggc
agcatgctcccatgagggaaaagcagtttttacagaaatttgctatggctgacggagaaggagggctcatacccaaagctgaaaaattcttatgtga
acaaaaaagggaaagaagtccttgtactgtggggtattcatcacccgcctaacagtaaggaacaacagaatCtctatcagaatgaaaatgcttatgt
ctctgtagtgacttcaaattataacaggagatttaccccggaaatagcagaaagacccaaagtaagagatcaagctgggaggatgaactattactgg
accttgctaaaacccggagacacaataatatttgaggcaaatggaaatctaatagcaccaatgtatgctttcgcactgagtagaggctttgggtccgg
catcatcacctcaaacgcatcaatgcatgagtgtaacacgaagtgtcaaacacccctgggagctataaacagcagtctcccttaccagaatatacacc
cagtcacaataggagagtgcccaaaatacgtcaggagtgccaaattgaggatggttacaggactaaggaacactccgtccattcaatccagaggtct
atttggagccattgccggttttattgaaggggggatggactggaatgatagatggatggtatggttatcatcatcagaatgaacagggatcaggctatgc
agcggatcaaaaaagcacacaaaatgccattaacgggattacaaacaaggtgaacactgttatcgagaaaatgaacattcaattcacagctgtggg
taaagaattcaacaaattagaaaaaaggatggaaaatttaaataaaaaagttgatgatggatttctggacatttggacatataatgcagaattgttag
ttctactggaaaatgaaaggactctggatttccatgactcaaatgtgaagaatctgtatgagaaagtaaaaagccaattaaagaataatgccaaaga
aatcggaaatggatgttttgagttctaccacaagtgtgacaatgaatgcatggaaagtgtaagaaatgggacttatgattatcccaaatattcagaag
agtcaaagttgaacagggaaaaggtagatggagtgaaattggaatcaatggggatctatcagattctggcgatctactcaactgtcgccagttcactg
gtgcttttggtctccctggggcaatcagtttctggatgtgttctaatggatctttgcagtgcagaatatgcatctgagattagaatttcagaaatatgag
gaaaaacacccttgtttctact __ UTR/HA PS
Bold - Mutated PS
*Italics* - PTV-2A Site
Underline - ORF HA
*Bold Italics* - Kozak Sequence
Bold Underline - ORF NA
*Italics Underline* - Furin Site
*Bold Italics Underline* - HA Signal Peptide sequence

Figure 20 – SEQ ID NO: 47 agcgaaagcaggggttaaaTtgaatccaaatcagaaaataacaacattggatcaattgtctggtagtcggactaattagcTtaatattgcaaata
gggaatataatctcaatTtggattagccattcaaactgaagtcaaaactatcggaatTtgcaaccaaGATATCgccccATGGCAC
AGAGCAAACATGGACTCACCAAGGAAATGACAATGAAGTATAGAAGAGGATAGAAGTATAGAGAGGATGGTCGAGGTCATAAATTC
GTAATCACTGGGGAAGGAATGGTTACCCGTTCAAAGGAACAGGCCATTAACCTGTGTGTCGAGGGGG
TCCTCTTCCTTGCAGAGGATATTCTAAGCGCAGCGTTTATGTATGGAAATAGGGTGTTAACGAATATCCTCAAG
ACATCGTAGATTATTCAAAACAGTTGCCCGCCGGGTACACTGGATAGATCTTTCTGTTCGAGGAGGAGC
AGTGTGCATATGTAAGCAGACATTACAGTGAAGATGAACGTATCAGTATCACGAATCTAAATTCTATGGC
GTAAACTTCCCTGCCGATGGCCGGTTATGAAGGAGAGTCAACTGGACAACTGCTGTGGAAAAGATAATT
CCAGTTCCTAAACAAGGCATTTGAAGGGGAGAGTCAATGTATCTACTCTTAAGGATGGCATTCATCCAGCATAAACT
GCCAGTTCGATACAGTATATAAAGCAAGAGCGTGCCTGAAAGAATGCCACCTGACTGAGCATGCCATAGCCTCTGGTCCGC
GACCCGAGAAGATCGGTCTGATGCAAAGAACCAAAAATGGCACCTGACTGAGCATGCCATAGCCTCTGGTCCGC
CCTCCCATGAAGTTTAAACtgagctaacaggctagactgtatggccgtgcttctggttgaattaatcagggacgacctaaagaaaaa
caatcggactagtgcgacgcagcagcatttctttttggcgtgaatagtgatactgtagattggtcttggccagacgtgctgagttgccattcagcattgac
aagtagtctgttcaaaaactcctgttctact ___ UTR/NA Packaging Signals
Bold - Restriction Digest sites (5′ EcoRV, 3′ PmeI)
*Italics* - Kozak Sequence
<u>Underline</u> - ORF ZsGreen

Figure 21 – SEQ ID NO: 48 agcgaaagcaggggtttaaaTtgaatcaaatcagaaaataacaaccattggattccaaatcatctgtcgtagtcggactaattagccttaatattgcaaata
gggaatataatctcaatTggattagccattcaaactggaagtcaaacatactggaaTtgcaaccaaGATATCgccccccATGAAA
*ACAATAATAGCTCTTAGCTACATCTTCTGCCTAGTCTCTCGGGCAG*gacctcaggaaatgacaacagcacagcaacgctgtgc
ctggaacatcatgcggtgccaaacgaacactagtgaaacaatcctcatgaatcttgatgaatagatagtgcacactgtgttacccttaggtgattcagctctc
aacgggaaaatatgcaacaatcaacatcctcatgaatcttgatgaatagatagtgcacactgtgttacccttatgtgtgcagattgcctcccttaggtgattttca
aatgagacatggaccttttcgttgaacgcagcaaagtttcactgaggtttcactgactgcgatcaaccaatgcttgcaaaggagacctgcttgatgccagctgcct
cgtcaggcactcgaactgttgccaaatcaggagcgaacgcaagaagcacatatccgcctgtagttcagcatcaggagagtcacagtctctacaggaagaagccagcaa
tttttcagtagaatcgaactgtttgccaaatcaggagcgaacgcaagaagcacatatccgcctgtagttcagcatcaggagagtcacagtctctacaggaagaagccagcaa
tgggggggttcaccaccgagcgaacgcaagaacgcaagaacccctgatgaaggctctctggagtttatttcagtagaatatapcatcattgacaatattaatccaggagactgat
actataatccgaaatatgaagtccgaacccctgatgaaggctctctggagtttatttcaaaatgcgactggaaaagctcaataatgagtcgatgcacctattgaatcctg
aattaataagtaatggaacctaatgctcctcggggttatttcaaaatgcgactggaaaagctcaataatgagtcgatgcacctattgaatcctg
tatttcgaatgcatcactccaaatggaagcattccaatgcaaagcccttcaaaacgtaacgataaactagaggcctattccagcaaaagcaggtttcatagaaaatgg
gcaaaaccctgaagtttgccacatagcagcgggtttgtacgcgttgtaacgggtaatgcaaagccaatgaatgctcaaaatctgaaaccaatcatatcaagcagccatc
ttgggaggggatgataaacgttgaaacgcctgattgaaacactaaaatagatctctgtcttacaagatgcgaactttttgtcgctctgagaatcacatacaatgacct
tcaggacctcgagaaatagcttgaagacctaaatagctgcaacatagatctctgtcttacaagatgcgaactttttgtcgctctgagaatcacatacaatgacct
gactactcgaaaatgaacaagctgtttgaaaaatgaacatcaaagaggcaactcaaagaagaaatgctgaaagacatggccaatgttgttcaaaatataccaa
caaatgacacagcctgacatagagtcaaaatagacataaggggaaactagaagaggacaaggaagcattaaacacacggttcaaatcaaa
ggtgttgaactgaagtcggaataccaaagactggatcctgttgaattccttgc*ATTTCTTGCTTCTTCTGTGCGTGGTCTTGCTTGGT*
*TTTATAATGTGGGCTTGTCAAAGGGGGAAACATAAGATGCAACATATGTATATGAGTTTAAAC*tggctaacagggcta
gactgtgaggccgtgcttcggtttgaattaatcagggacgacctaaagaaaaaacaattggactagtgcgagcagcattctttttgtggcgtg
aatagtgatactgtagattgtcttggcagacgtgctgagttgcctgagttcaaaactcctgtttctact ___ UTR/NA Packaging Signals
Bold

Figure 22 – SEQ ID NO: 49 agcgaaagcagggggtttaaaTtgaatcaaatcagaaaataacaaccattggatcaatcgtctgtagtcggactaatattgcaaata
gggaatataattcaaTtggattagccattcaattcaaactggaagtcaaaccatactggaaTtgcaaccaagAIAICgcccccatgaaAgc
GaaTTgTTAgTTTTACtgTCCgcgTTgGgCGgCGgcGgaCgcagacaccaatatatagccTccatgcgaacaattcaacgacactgttg
acacagtactcgagaagaaatgtacagtgacagtgacacactcgttaacctgctcgaagaagcactatgtagattacaaggcaaatagccc
cactacaattggagaaaatgtaacatcgccgatgcctTtgggaaccccagaaatgcgaccactgcttcagtgacatcatgtcctacatgtagaa
acaccaaactcgagaatctgagaatatgttatcaggagattcatcggagattacattgaggaaccaattgactcagtgtctcatcattgaaagatt
cgaaatatttcccaaagaaagaagctcatgcgacaaacggagtaacgacCgcaatgcctcccatgagggaaagcagttttacagaaa
tttgctatgctgcgagaagcagtaaggaacaacagaaatcttatgcctcatacccaagctgaaaatgctaatgtctctgtagtcactttctgtagttacaggaagattacccgga
atcaccgcctaacagtaaggaact

Figure 23 – SEQ ID NO: 50 agcgaagcagggtttaaaTtgaatccaatcggaaataacaaccattggatcaattgtctggatagtcggactaattagcctaatattgcaaata
gggaatataatttcaatTtgattagcccattcaattgaaaccatactggaatTtgcaaccaaGATATCgccaccATGAAG
GCAATAATTGTACTACTCATGGTAGTCACTACTCAAGGGAGTCAATGCACAGATCAATTGACCAAAGCTCAAAGCAC
CACATGTGTCAAAACTGTCTACTCAAGGAACAGAAACCAGAGGAACTCAATGTGACTGGAGTGTAATCCAAAACACCCACCAA
ATCTCATTTGCAAATCTCAAAGGAACAGATGCAGGGAACATACCCTGGCAAGAGTTTCATATCCTCATGAAGTCAGA
GAGTGGCCTTGGGCAGACAAAATGCAGGGGAACATACCCTGGCAAGAGTTTCATATCCTCATGAAGTCAGA
CCTGTTACATCTGGTGTCTTTCCTATAATGCATAAGTTATCAACGTTATCAGAAGACATCATCATCTTCAGAGGAT
ACGAACATATCAGTTACCCTAACGTTACCAATGGAAACGGATTTTCGCAACAATGGCTTGGGCCGTCCAAAAAACGAC
CTCAGGGTCTGCCCTAACTCATGAAACAGAACAAATTCATTAACAATAGAAGTACCATACATTTGTACAGAAGACCAAATTACC
AACAACAAACAGCAACAAATTCATTAACAATAGAAGTACCATACATTTGTACAGAAGACCAAATTACC
GTTTGGGGGTTCACTCTGATAGGCAACACATTACGTTCACAGATTGGTGCTTCCCAAATCAAACAGAAGACGGAGGA
TCATCTGCCAACGGAGTGACCACAGCTTCACAGATTGGTGCTTCCCAAATCAAACAGAAGACGGAGGA
CTACCACAAAGTGGTAGAATTGTTGATTACACATGGTGCAAAAATCTGGAAAACAGGAACAATTACTATCAAA
GAGTATTTTATTGCCTCAAAAGTGTCGTGCCAAGTGCCAGGAGCAAGGTAATAAAGACAAGCCTTACTACAGGGAACATG
TTGGAGAAGCAGATTGCCTTCCGAAGAATTGCCCAATAGGGTTCTTCGGAGCTATGCTGGTTCTTAGAAGGAGGATGGGAAGGAATGA
CAAAGGCCATAACAATTAAAGGAAGGGGTTCTTCGGAGCTATGCTGGTTCTTAGAAGGAGGATGGGAAGGAATGA
CTGCAAACTATTAAAGAAGGAAGGGTTCTTCGGAGCTATGCTGGGTGGCAGCAGATAGCGCGGTGGCAGCAGATAGTGAAGAGCACTCAA
GAGGCCAAAACAAGATAACAAGAAAATCTCAACTCTTTGAGTGAGTGAAGTAAAGAGAGAATAATAAACAGTGAAGATGACTCTCTTGCGC
GGTGCCATGGATGAACTCCACAAGATCCAGTCGTCACAGAAAATGCTGGGCCCTCTGCTCTGCTACTTCTGCAGGAGAATTCTCTCCCACTTTGAT
AGCTCAAGAAGCTGAAGAAATAGAACTCGCAGTCGTCTCGACAGAATAGCTGGGCCCTCTGCTCTGCTACTTCTGCAGGAGAATTCTCTCCCACTTTGAT
TTGAAAGAAAGTGAAGAAATAGAACTCGCAGTCGTCTCGACAGAATAGCTGGGCCCTCTGCTCTGCTACTTCTGCAGGAGAATTCTCTCCCACTTTGAT
AGTGCAACCAGAACTGTCTGACAGAATAGCTGGGCCCTCTGCTCTGCTACTTCTGCAGGAGAATTCTCTCCCACTTTGAT
TCACTGAATATTACTGCTGCATCTTAAATGACGATGGATGATAATCATATACTATACGGATCATCATATATGGTCTCCAGAGACAATGTTTCTGCTC
GCCTCCAGTTGGCTTGGCTGTAACATTGATGATAGCTATCTTTGTTGTTTATATGGTCTCCAGAGACAATGTTTCTGCTC
ATCTGTCTATAAGTTTAAACtggctaacagggtctagactgtatgaggcgtgcttctgggttgaattaatcagggagggacgacctaaggaaaa
aacaatggactagtcgagcagcagcattttttttggcgtgaatagtgtactgtagattggtcttggccagcagcgtgctgagtgtgcattcagcattg
acaagtagtcgttcaaaaaactccttgttctact <u>UTR/NA Packaging Signals</u>
Bold - Restriction Digest sites (5' EcoRV, 3' Pmel)
*Italics* - Kozak Sequence
<u>Underline</u> - ORF HA

Figure 24 – SEQ ID NO: 51 agcgaaagcagggtttaaaTgaatcaaatcagaaaataacaaccattgaatcatcgtctgtagtggactaattgcctaatattgcaaata
gggaatataatcaatTtggattagccattcaatTcaaactggaagtcaaaaccatactggaatTtgcaaccagGATATCgccccaATGAAG
GCAATAATTGTACTACTCATGGTAGTAACATCCAACGCAGATCGAATCTGCACTGGGATAACATCTTCAAACTCAC
TCAATGTGGTCAAAACAGCTACTCAAGGGAAGTTAATGTGACTGGTGTGATACCACTGACACTGTCACTGCACAGATCTG
AATCTCATTTGCAAATCTCAAAGGAACAAAGACCAGAGGGAAACATATGCCCAAAAGCTTCAATACTTCACGAAGTCAGA
GATGTGGCCTTGGGCAGACAATGTGTATGGGACCATACCTTCGCAAAAGCTTCAATACTTCACGAAGTCAGA
CCTGTACATCCGGGTGCTTCTTCCTATAATGCAGACAGAACAAAAATCAGACAGTACCAATCTTCTCAGAGGAT
ATGAAAATATCAGATTATCAACCATAACGTTATCAACGTTATCAACGGGACAGAAGGGCACCAGGAGGACCTACAGACTGGAA
CCTCAGAATCTTGCCTAACGTTACCAGTAGAAAACGGATTCTTCGCAACAATTTGCACAAAAGGAGAAGACCAAATTACTGTTG
CAAAACAGCAACGAATCCACTACAATAACGAAATGTGATCCATAATCATTTGAGAAGACAATTGACGAGACAAATACTGTTG
GGGGTTCCATTCTGATAACAACAAAAACCAATGAAAAATCTCATATGCAGATTGGTGACTCCAAATCAACAGAAAAGTCACTCATCT
GCCAATGGAGTAACCACACATATGTTCTTTGATTACATGGTGCGCAAGTGCAGGAGCAAGGTAGAAACAAAAGCAAGCTTACTACACAGAAGACCGAGGCTACCAC
AAGCGGCAGAATTGTGTTGATTACATGGTGCGCAAGTGCAGGAGCAAGGTAATAAACAGGAACAATTGTCTATCAAAGAGGTG
TTTTGTTGCCTCAAAAGGAATTGCTTCACGAGTAAATACGGTGGATTAAACAAAGCAAGCCTTACTACACAGAAGACTAAGTGCAAAAG
AAGCAGATTGCCTTCACGAGTAAATACGGTGGATTAAACAAAGCAAGCCTTACTACACAGAAGACTAAGTGCAAAAG
CCATAGGAAATTGCCAATATGGTGAAAAACACTTGAAGCTTGCCAATGAGGGAGGATGGGAAGGAATGATGCAG
ACTATTAAAAGGAAAGGGGTTTCTCGGAGCTATTGCTGGTTTCGTGGTGCGCAGTAGAAGCACACCAAATATAGACCTCTGCAAA
GTTGGCACGGATACACATCCAGTCTTGCTTCATTCCAATTCTTTGAAGTGCAGTGGCAGTAGAAGTAAAGAAGCACGCAAGAAGCC
ATAAACAAGATAACAAAAGATAACAAAAACGAAATATCGAGCTGGATGAGAAAGTGATGATCTCAGAGTCGACACAATAAGCTCGC
TGGATGAACTCCACAGCATGCTGCTGATGGATGGAATGATTGGATAATACATACTGTCTACTACTCAACTGTCTTCT
AAATAGAGCTTGCAGTCTTGCTTGCCAACGAAGGAATAATAAACAGTGAAGATGAGCATCTATTGGCACTTGAGA
GAAAACTAAGAGAAAATGCTGGGTCCCTGTCGTGAGATACGGGAATGATGCTTCGAAACCAAACAAGTGCA
ACCAGACCTGCTTAGACAGGATAGCTGCTGCGACCCACCTTAATGCAGGAGAATTCTCTTCCCACTTTGATTCATG
AATATATTACTGCTGAACATCTTAAATGATGAGCTATTTTATGTTATATAGGTCTCCAGAGACAATGTTTTCTGCTCCATCTGT
AGTTTGGCCGTAACATGATGATAGCTATTTTATGTTATATAGGTCTCCAGAGACAATGTTTTCTGCTCCATCTGT
CTATAAGTTTAAAACtggctaacagggtctaagactgagcctgtcttggttgaataatcagggacgacctaaagaaaaacaatct
gaactagtgcagcagcattctttttgcgtgaatagtgatactgagattgctttgccagacggtgctgagttgcattcagcatttcaagta
gtctgttcaaaaactctcttgttttctact ___ UTR/NA Packaging Signals
Bold - Restriction Digest sites (5' EcoRV, 3' PmeI)
*Italics* - Kozak Sequence
<u>Underline</u> - ORF HA

Figure 25 – SEQ ID NO: 52 agcgaaagcagggggtttaaaTtgaatccaaatcagaaataacaaccattggatcaatcgtctggtagtggatactaattgcaaata
gggaatataattcaatTggattagccattcaatcaaactggaagtcaaaaccatactggaatTgcaaccagGATATCgccccATGAAG
ACCATCATAGCACTGTCATATATACTTGCCCTGTGTTGCGCCAGaaacttcccgaaatgacacagcacgacggcctgtgcc
ttggcaccatgcattaccaaatcggaacgatagtgaaaactcctcatagatcttgatggagaaacctcattggagacctcagtgatgcttccta
acaggtggaatatgcgacagtgcctacaactgttacccttatgtatgtcggaattatgcctcctctaggtcactagttgct
aataagaaatggaactttttgttgaacgcagcaaactttcaattgactggagtcactgagacccagtcactgaattgccagttccaa
catccggtacactgagtttaacaatgaaccattaaatcaatacccagtcactgttaaatacaatcaaagcatcacaggatcctaataaaagt
ttctttagtagattgaattggttgaccccggtacgacagtgacccaggtaagggtgtctccagcagagaatcagcatattgccaacaa
gtgtaatcccggaatatcggatcgaataactcaattgctcctaggagttactccaaaatacgaatgtgaaaactcaaatgcctgataaaat
attaacagcacagggaatcTaattgctcctaggagttactcacaataatgagaacactttaaacgaatcagaatagatagctgaaat
gcaattctgaatgcatccaaatgaaggcattccaaatgacaaaccattcaaacagaatcactcaatgtaaacaggtatattgccagatatatta
agcaaaacactctgaaattggcacaggagatgccaatgtaccaagagaaggctgagaatgcaatgcgagtgcggttcataaagaaatg
gttgaggagaatgtgacagttgtacggttgagctcagcctcaaattcggagggcaaccagagaattccatcagatcggagcagcaccaagcagcaa
tcaaccaaatcaatggaaaactggaatggaagttaatcgaagaactaaatgttgaggaaatatgtcatcacacagcgaaagcaagagaatttcagaatcagaagggaa
attcaggaccttcagaaaatatgttgaggacaaactgtttgaaagaaacaactgctgaagatagatctggaaaggcatgagaatagctacgtgat
ctaactgactcagaaatgacaactgcctgaggtcaatcagaatgagtggaaagaactgaggaataagcaactgaggagtatggcaatggtgttcaaatatacc
acaaatgtgacatgcctgcatgggtcaatcagaatggaactgatcagaagaactatgccatgatgtatcacagagataagaacacgttcagatcaa
aggtgtgagctgaatcgaagatacaaagattggatcctatggatttcttttgcATCTCCTGTTTCTACTGTGTGGCTCTGCTGGG
TTTATTATGGGCATGTCAGAGGCAATATACGGTGTAATATCGAGTTTAAACtgactaacaggct
agactgtatgaggccgtgctctgggttgaattaatcaggggacgaccttaaagaaaaaacaatcggactagtgcgagcagtatttttgggcgt
gaatagtgatactgagattggttcgtcgagacgtgcgtgagttgcacaagagtagttgttcaaaaaactcttgttttcact \_\_ UTR/NA Packaging Signals
Bold - Restriction Digest sites (5' EcoRV, 3' PmeI)
*Italics* - Kozak Sequence
Underline - ORF HA
Bold Underline - Mutated Packaging Signals

Figure 26 – SEQ ID NO: 53

```
agcgaaagcagggtttaaaTtgaatcaaatcagaaataacaaccattggatcaatctgtctggtagtcggactaattagcctaatattgcaaata
gggaatataatctcaaTtggattagctcattcaattcaaactggaagtcaaaacatactggaaTtgcaaccaaGATATCgccctcAIGAAA
ACAATTATCGCTCTTTCATACATTCTTGCCTGCTTGCTTCTTGACAAacttccggaaatgccaacagcagcaacgctctgcct
tgggcaccatgcagttaccaaagcgacagtgtaagatggaacatgaagtagtacatgaagttactaatctactgactgttcagaattcctca
acaggtgaaatatgcgacagtgctcatcagatcttgatggaaaactgccactgtgcgcactaataatgtccactgttaccctcttattggagaccctcagtgatgcctca
aaataagaaatggcacttttttgttgaaacgcagcaaagccctacacagcaactgttacctcaaacggaacagctgcttgcataaggagatctcaaaacca
tcatccgccacactggagtttaacatgaaagcttcaattggactgactggagtcactcaatccccagcatgaaactgcctggaacaatgaactatgaccaaatgaacaag
gttctttagtagattgaattggttgactaactaaacttcaaatccccagctttcgtatgtcaagcaatggggatctattgaacagtcttaccaaaagaagcaacaag
ctgtaatcccgaatatcggagatctagaccgagtaagaataagtcctagcagaataagcattattgacaataagtaaaacggagatcatactttg
attaacagcacagggaatctaattgctccaggggttactcaaatgcaaagtggaaaagctcaatatgagatcgatgcatccattggcaaat
gcaattctgaatgcatcactccaaatgaagcattccaaatgaaagcaaacagaggatcacatcaggatcacataggatccatatggcccatccgcctctgtatgtcccagatatgtt
aagcaaaacactctgaaatgtgccacgaggatgcaacaggatcaaactcagcaagaaactcacgggaaatcaactgggaatgcatcgccggtttcatgaaat
gttgggaaggagaatgtggaatgttgttacggtttcagccatcaaatctgaccaggaaagagagacaacagcctcaaagcactcaagcacaagca
atgcatcaaatcaaggaaagctgaatagcattgttggggaaatagctgtgcactaaaatatgatctcagattctcagaagtgaaggggaga
atcaggaccttgaaaatatgttgaggccactaaatagatctctgtatacaacgcgggagctttcttgtcctgaaaccaacatacaattgat
ctaactgactccaggacaactgtttgaaaacctgttacgaggatcaatcagaaatcagagaagaagcaactacagaattgacacaggaatttcaaataaac
cacaaaatgtgacaatgctgcataggatcaatcagaaatcagaaatgcactgaatgagcattaaacaaccgttttcagatca
agggagttgcctgaagtcagggctcagggatcaaagatcagggattTCATTTGCTATATCGTGCTTTCTACTATGCGTAGCACTCC
TCGGGTTATTATGTGGGCCTGCCAAAAGGAAATATTAGATGCAACATCTGTATTGAGTTAAACtgagtaaca
gggctagactgtgatgaggccgtgcttctgggttgaattaatcagggggcgacctaaagaaaaaacaatctggactagtgcgagcagcattctttttgt
gggctgaatagtgatactgtagattggtctgggccagacggtgtgagttgccattcagtcagtgcctgcattcagtcagtgttcaaaaaactccttgttctact
```

___ UTR/NA Packaging Signals
Bold - Restriction Digest sites (5' EcoRV, 3' PmeI)
*Italics* - Kozak Sequence
Underline - ORF HA
Bold Underline - Mutated Packaging Signals

Figure 27 – SEQ ID NO: 54

Legend:
- UTR/HA Packaging Signals
- Bold - PTV-2A Site
- *Italics* - ORF HA
- <u>Underline</u> - Kozak Sequence
- *Bold Italics* - ORF ZsGreen
- <u>Bold Underline</u> - ORF NA Transmembrane and Cytoplasmic Tail
- *<u>Italics Underline</u>* - HA Signal Peptide sequence

```
agcaaaagcagggggaaaataaaaacaacaaaTtgaaggcaaactactgattcctgttaagtgcacttgcagtcgagTtgcagacacaaTTgta
taggcaccATGAATCCAAATCAGAAAATCATTCAGAAAATACCACAATTGGAATACCAATGAAATCAATGGATCAGCCATTCTATACAACGATGATCAACAGCATCTCAT
TCTTCAAAATTGGGAACATCATTCAAATTGGATCAGCCATTCTATACAACGATGATGCTCAAGAGCATCAGTCTCAT
CACTAAAGAAATGACTATGAATCCCTTTAAAGGAAGAACAACGCAATTAACGTGGATGGCCATAAGTTTGTAATTACTGGAGAA
GGCATTGGATACTCTCAGTGCCCCGCGGTTATGTATGGCAATGGGACATGGAAGAAAATTTATGAGTCCAAATTTATGGAGTCAATTCCCG
TTCAAGAACTCATGCCCCGCGGTTACACATGGGACATGGAAGAAATTTATGAGTCCAAATTTATGGAGTCAATTCCCG
ACGCGGATATTACGGTAGTGTGAAGAAGAAATGCATGTATCATGAGTCCAAATTTATGGAGTCAATTCCCG
CAGATGGACCAGTCATGAAGAAGATGACAGATAACTGGACAACCAGTGTGAGAAAATAATACCGGTACCAAA
ACAAGGCATACTCAAGGTGATGTGTCAATCGTATTTACTCTCAAAGACGGTGGACGTTTACGCTGCCAGTTGA
CACAGTGTATAAGGCTAAATCGTCCCCAGGAAATGCCAGATTGGCACTTTATTCAACACAAGCTTACTCGGGA
GGACAGGTCTGATGCAAAGAATCAGAAATGGCATCTTACAGAACAATGTCATTGCCAGTGGTAGTGCTCTCCTG
GCAGTGGGGACTATAAGGACATGATGATGACAAGGAAGCGGTGCTACTAATTTTCACTTCTCAAACAAGGAGG
CGATGTGGAAGAAAACCCCGGACCAAgtgaaAgcGaaTTtGTTAcTTAcTGTCCgGTTgacGgcCaGGaatGcagacac
aatatgtatgtcgaacatgcgaacattcaccgacctgttgcccactcagctgcaggaagtgtgaccacactcctgtcaactgatc
gaagacagccccaccgcgacccactgcttccgtggagctccaccattgtgaaaccacccacctcgcggaatatgttctccgagagcatc
atcgactcctgggagctggggtaccgcccgaataggattgccaatatgttgccggaaagggcaccggagggctcatgcggtaaggcg
acccgaagcgtcgcaacgttctatggtgaacaaagagaagagtccttgtactgtactgcggtggttgtattcaatcaaccagcctcacccctggaccc
cagatcTctatcaggaatgcaatgcttatgtctgtgtagtggactTcaaattataacaggagaacttTccccgggccaatgcagaagcgccccaac
gtaaggagatccaagctgggagggatgagagaagagcatcatactggcctttggtctggaatcagaaccccgcaatggccccagatccatcaagcagc
accaatgtatgttttgcactgagtgaggtaggccttcaatgcaaccatccataccctcaagcaattgcatgtagaggctgggagcaaaggatccaagcg
ccctggaggctctcaagccagtcgacacccagcctctccttgaccagaggtcttcctccagcctcctcaaaatcgtcaaagtgagtgccaattg
aggatggttccagagtgactcgacagagaccatgttggccattcgggccctctttgtcttgcgggggtcacggtcaggggctcatgcctaccgg
tgatcgtgtatggatggtgctgtgctgtgacctttgtctccagcgtgtacagcaatgaacaagggcataaacaaatggccccttaacggg
attacaacaaggcctggacctgagaaggttgaaggcggtggtgttccagcacgccccactttggcatttggtggttgtggtaaggccattgagaaaggaagatgga
tccatgtcttcaaggtggcaggtctgtgtgaaggcgtcctcatgatggttacgcggatcttggctacagcacgggagaccagtagcccaaataccagtcttaagaagattggacggcttttgagttct
accccagtgtgaaatgaatgaagaagcctgaaagaaaaggtgacgagtcaagaatggttcctatctcccccagatccaggacacggttgaccaggggaa
aggtagatgaatggacagtcagtggagaagttcggaaactccggtgcagccggcagcgatggttcctcttcagtgctccgatcctcgatggatccagtatcgggagattagaatcagaaattcagaaatgcagaaaaccctgt
tttctact
```

Figure 28 – SEQ ID NO: 55 agcgaaagcagggtttaaaTtgaatccaaatcagaaatcaTtgcatcaatcgtcTggtagtggactaaTtagcTaatatgcaaata
gggaatataaTcaaTTggaTTagccaTtcaTtgaaTtcaactggaagtcaaaccaTactggaaTTgcaaccaaGATATCgccccATGAAATC
CGGGTTTCGCACTAGCAGCGCGGCCAGCCTACTCAATTCGATGTATAGGTGTCAAACGAGATTCGTTGAAGGAAT
CATGATATCTGCTCATAGCGCCAGCCTACTCAATCGATGTATAGGTGTCAAACGAGATTCGTTGAAGGATAAACC
GTCGGAGGAACATGGGTGGATGTGGGTGCTAGAGCACGAGAGGGTGTGTGACGTAATGCTCAGGATAAACC
CACAGTGGATATAGAACTAGTAACCACTACTAGTTTCTAAACATGGCAGAAGTTAGAAGCTATGCTATGAAGCAA
GTATTAGCGATATGGCCTGGATTCCAGGTGTCCACACAGGAGGATGGGGGAACGGGTGTGGCCTCTCGGGAAAGGAAGT
CAATATGTGTGCAAGAGAACCTAGTGCGATAGAGGATGGGGGAACGGGTGTGGCCTCTCGGGAAAGGAAGT
CTTGTTACATGTGCAAAGTTGCTTGTTCTAAGAGTCAGTCAGCATTCAGATTCAACACAGGCCACAGAAATCTCGAATAT
CGAATTATGCTTAGCGTGCAGGGAGTGAGTTACTCCTAGAGTCAGATGATAGTCACACAGGCCACAGAAATCTCGAATAT
AGAATAGGGCTAAGGTTGAGATTACTCCTAATTCTCTAGACGCAGAGGCTACTCTTGGAGGGTTTGGAAGCTTA
GGATTAGACTGCGAGCCAGGACTGGTTCACGATGGATCTGATACCACTGCAGGGCGAGACACTGTGGGCTAAGGTGTCTG
GCTAGTGCATAAAGGAAGCTCGGTTGAATGCCAGGAGCACATGCAAAACTTAGGTGAAGGCAGAAATGGATGGGTGCTTG
GGAATAATAAGGGCTGTTCATAGGCTTGGCTTGGACTCAAAATGCCACTCAAAATGGACAAACATTGCACGGAACAGTGACACTCTAACTCCAGTGGGAGACTTA
CCAGGAGGCCATCTAAAATGCGACTCAAAATGGACAAACATTGCACGGAACAGTGACACTCTAACTCCAGTGGGAGACTTA
AGTTCAGGCCATTACTTCACCAAATTCCAGCGAGTAGCCGGTTGACATGCAAAGATGGTAGGACGTCTAACATAGCCTCTGTACT
GCCGCATTTACTTCACCAAATTCCAGCGAGTACCGGTTGACATGCAAAGATGCTTGAAGTTCATATAGCCTCTGTACT
AACAGATGACCTTGCAAGTACCGGTGGTGAAAATCCGTGTAATCACAGAGAATGAATTTTGGAGAGTGTGAGACTCGGGG
TTACACAAAATCTGTATCGGCGTGGTGAAAATCCGTGTAATCACAGAGAATGAATTTTGGAGCGGCTCTACCATGGCA
ATTCGTATATTGTTATCGGCGTGGTGAGGGGCCACTAAAAGAATGGTGTGTTGGGACACAGGTGGGGACTCGGTC
AGGCTTTGAAGCCACTGTGAAGTAGCTGGAGGGGCCACTAAATGGGAATGGTGTGTTGGGACACAGGTGGGGACTCGGTC
TGTAGGAGGCGCACTAAATAGCTTGGAGGGGCCAAAATTTTGGAGAATTTTGGAGCACTCATTTATGTGGACACAGGTGGGGACTCAAATGGA
GAGGTATGTCATGGTTAGTCAAATCTGATAGGCACTCTACTTATGTGGACACTAAATAAAAATGA
ICCATTAGGCTAAGCTTAGCTTTGGATTTCTTAAAAAAAAAGGACGACCTAAAGAAAAAACAATCGGGACTAGTGCAGCA
gagctaacagggcTagacTgtatgaggccgtgcTTtggTTggattaatcaggggagcgaccTaaagaaaaaacaatcTggacTagTgcagcagca
ttctttttgtgccgtgaatagtgataCtgtagtacTgaaTtgtcTtggccagacgctgaaTtgccattgccatTcaacaagtagTcTgTTcaaaaaactcctt
gttctact UTR/NA Packaging Signals
Bold - Restriction Digest sites (5' EcoRV, 3' PmeI)
*Italics* - Kozak Sequence
Underline - ZIKA prM Protein
Bold Underline - Zika E Protein

ENGINEERED INFLUENZA POLYNUCLEOTIDES, VIRUSES, VACCINES AND METHODS OF MAKING AND USING THE SAME

CROSS-REFERENCE TO RELATED PATENT APPLICATIONS

The present application is a national stage filing under 35 U.S.C. 371 of International Application No. PCT/US2017/041737, filed Jul. 12, 2017, which claims the benefit of priority to U.S. Provisional Patent Application No. 62/361,131, filed on Jul. 12, 2016, and U.S. Provisional Patent Application No. 62/505,256, filed on May 12, 2017, the contents of which are incorporated herein by reference in their entireties.

STATEMENT REGARDING FEDERALLY SPONSORED RESEARCH

This invention was made with United States government support awarded by the National Institute of Health grant numbers T32-GM007184-41 and T32-CA009111. The United States has certain rights in this invention.

SEQUENCE LISTING

This application is being filed electronically via EFS-Web and includes an electronically submitted Sequence Listing in .txt format. The .txt file contains a sequence listing entitled "155554 00467 ST25.txt" created on Oct. 16, 2020 and is 48,388 bytes in size. The Sequence Listing contained in the .txt file is part of the specification and is hereby incorporated by reference in its entirety.

INTRODUCTION

Influenza A virus (IAV) is a major public health threat and vaccination is currently the best available strategy to prevent infection. While there have been many advances in influenza vaccine production, the fact that we cannot predict the growth characteristics of a given strain under vaccine production conditions a priori, introduces fundamental uncertainty into the process. Clinically relevant IAV strains frequently grow poorly under vaccine conditions, and this poor growth can result in the delay of vaccine production or the substitution of the recommended strain for one with favorable growth properties. Even in strains that grow to high titers, adaptive mutations in the antigenic protein hemagglutinin (HA) that make it antigenically dissimilar to the circulating strain are common.

IAV, a member of the family Orthomyxoviridae, is a negative sense RNA virus with a segmented genome (1). Seasonal IAV is a major public health concern, causing nearly 5 million cases of severe illness a year, and an estimated 250,000-500,000 deaths (2). Vaccination is the main strategy used for limiting the public health burden of this virus; and neutralizing antibodies directed against the HA protein are thought to be the most important contributors to protection (3). Influenza virus vaccines are normalized based solely on HA content (4) and recombinant HA-protein only vaccines are FDA approved and currently in use (5).

Current tri- and quadrivalent inactivated egg and cell based influenza vaccines rely on incorporating the glycoproteins from one of the desired strains into a standardized influenza virus genetic background, amplifying the virus, then inactivating and partially purifying viral proteins for vaccination (6). The vaccine production process can be delayed due to poor growth of the reassortant viruses under laboratory conditions (7-9), and in extreme cases, the failure to grow a desired strain for vaccine production can lead to its complete exclusion from a multivalent vaccine formulation (10). This has been a problem particularly for recent human subtype H3 IAV strain-derived HA proteins that frequently display poor infectivity in embryonated chicken eggs (11-13).

Further, IAV vaccines are notorious for displaying variable rates of protection (14, 15). Poor vaccine efficacy is frequently blamed on improper vaccine strain selection or antigenic drift of circulating viruses, however recent work has shown that the viral antigens acquire mutations during vaccine production, which leads to human vaccination with an antigenically dissimilar virus (16, 17). Thus, the ability to predictably grow any influenza virus strain to high titers, without altering the structure or antigenicity of the HA protein, would represent a significant improvement to current influenza virus vaccine production.

Additionally, expressing heterologous polypeptides in IAV vaccines has proven difficult and cumbersome given that heterologous polypeptides have been incorporated into segments of the IAV genome (i.e., segments other than segments 4 and 6) that are typically not altered when producing commercial reassortant viruses using reverse genetic techniques. Current locations for heterologous protein expression may also be constrained by size limitations and the cis regulatory elements controlling adjacent viral genes. There, thus remains a need in the art for engineered influenza viruses that can express heterologous polypeptides in a more flexible manner and that are amenable to current production techniques. Such influenza viruses may serve as a platform to deliver additional antigens in flu vaccines and could serve as important new diagnostic tools for producing flu vaccines.

SUMMARY

In one aspect of the present invention, engineered influenza virus segment 4 polynucleotides are provided. The engineered influenza virus segment 4 polynucleotides may include a first polynucleotide encoding a first hemagglutinin (HA) polypeptide and a second polynucleotide encoding a heterologous polypeptide, wherein the first polynucleotide is linked to the second polynucleotide by a detachable linker. Alternatively, the engineered influenza virus segment 4 polynucleotides may include a first polynucleotide encoding a first hemagglutinin (HA) polypeptide and a second polynucleotide encoding a first neuraminidase (NA) polypeptide, wherein the first polynucleotide is linked to the second polynucleotide by a detachable linker. In some embodiments, the engineered influenza virus segment 4 polynucleotides may include a first polynucleotide encoding a heterologous polypeptide.

In another aspect, engineered influenza virus segment 6 polynucleotides are provided. The engineered influenza virus segment 6 polynucleotides may include a first polynucleotide encoding a first neuraminidase (NA) polypeptide and a second polynucleotide encoding a heterologous polypeptide, wherein the first polynucleotide is linked to the second polynucleotide by a detachable linker. Alternatively, the engineered influenza virus segment 6 polynucleotides may include a first polynucleotide encoding a first hemagglutinin (HA) polypeptide and a second polynucleotide encoding a first neuraminidase (NA) polypeptide, wherein the first polynucleotide is linked to the second polynucleotide by a detachable linker. In some embodiments, the engineered influenza virus segment 6 polynucleotides may include a first polynucleotide encoding a heterologous polypeptide.

In a further aspect, plasmids are provided. The plasmids may include any one of the engineered influenza virus segment 4 polynucleotides or the engineered influenza virus segment 6 polynucleotides described herein. Suitably, the plasmids may include any one of the engineered influenza virus segment 4 DNA polynucleotides or the engineered influenza virus segment 6 DNA polynucleotides described herein.

In a still further aspect, plasmid compositions are provided. The plasmid compositions may include any one of the engineered influenza virus segment 4 DNA plasmids and/or the engineered influenza virus segment 6 DNA plasmids described herein as well as the remaining plasmids encoding the remaining influenza virus segments 1, 2, 3, 5, 7, and 8.

In another aspect, engineered influenza viruses are provided. The engineered influenza viruses may include any one of the engineered influenza virus segment 4 polynucleotides or the engineered influenza virus segment 6 polynucleotides described herein. Suitably, the engineered influenza viruses may include any one of the engineered influenza virus segment 4 single-stranded negative RNA polynucleotides or the engineered influenza virus segment 6 single-stranded negative RNA polynucleotides described herein.

In another aspect of the present invention, compositions including engineered influenza viruses are provided. The compositions may include any one of the engineered influenza viruses described herein. In some embodiments, the compositions include at least $10^6$ pfu/mL, $10^7$ pfu/mL, $10^8$ pfu/mL, or $10^9$ pfu/mL.

In a further aspect, the present invention relates to vaccine compositions including engineered influenza viruses. The vaccine composition may include any one of the engineered influenza viruses described herein and a pharmaceutically acceptable carrier and/or an adjuvant.

In a further aspect of the present invention, methods for preventing or reducing the symptoms of influenza in a subject are provided. The methods may include administering a therapeutically effective amount of any one of the engineered influenza viruses or the compositions or vaccine compositions including engineered influenza viruses described herein to the subject to prevent or reduce the symptoms of influenza in the subject.

In another aspect, the present invention relates to methods for producing an influenza virus. The methods may include introducing any one of the compositions described herein (i.e., engineered influenza virus segment 4 and segment 6 polynucleotides, plasmids, plasmid compositions, engineered influenza viruses, engineered influenza virus compositions and vaccine compositions) into a cell.

In a still further aspect, the present invention relates to methods for detecting the presence of a rescued influenza virus in a cell in a culture. The methods may include introducing any one of the plasmid compositions disclosed herein including a polynucleotide encoding a heterologous polypeptide into a cell. Suitably, the heterologous polypeptide includes a fluorescent polypeptide or an antigenic polypeptide.

BRIEF DESCRIPTION OF THE DRAWINGS

The patent or application file contains at least one drawing executed in color. Copies of this patent or application publication with color drawings will be provided by the Office upon request and payment of the necessary fees.

FIG. 2 shows the mRuby2-HA virus stably expresses the reporter protein over serial passaging.

FIG. 3 shows encoding a green fluorescent reporter protein in segment 6 without leaving residual tags on the viral NA protein. (FIG. 3A) Diagram of the genomic segment 6 NA based fluorescent reporter virus. (FIG. 3B) Endpoint titer of the NA-Furin-mNeon virus compared to WT PR8 after 72 hr incubation in eggs. (FIG. 3C) Multi-cycle growth kinetics of the NA-Furin-mNeon virus on MDCK cells compared to WT. (FIG. 3D) Flow cytometry of NA-Furin-mNeon infected (green) and uninfected cells (grey) represented as a histogram. (FIG. 3E) A quantification of brightness of fluorescence in the NA-Furin-mNeon infected cells.

FIG. 4 shows a schematic of the Neuraminidase-Furin-mNeon construct, and it's processing. (FIG. 4A) A depiction of the amino acids encoded by the construct, amino acids are color coded to match the specific portions of the construct they come from. (FIG. 4B) A depiction of the inability of ribosomes to form a peptide bond between the final Glycine and Proline of the PTV1-2A sequence, causing the Neuraminidase and mNeon proteins to separate. (FIG. 4C) A depiction of Furin protease recognizing the cleavage RKRR motif and cleaving the remaining PTV1-2A amino acids from Neuraminidase. (FIG. 4D) A depiction of Carboxypetidase B enzymes cleaving the basic amino acids of the furin cleavage site from the N-terminus of Neuraminidase, leaving wild-type protein.

FIG. 5 shows the NA-Furin-mNeon virus stably expresses the reporter protein over serial passaging.

FIG. 6 shows expression of the HA and NA glycoproteins from a single segment allows the generation of a replication competent H1/H3 dual HA virus. (FIG. 6C) Endpoint titer of the segment 4 NA/HA, segment 6 ZsGreen virus compared to wild-type PR8 after 72 hr incubation in 10-day old eggs. (FIG. 6D) Flow cytometry of the segment 4 NA/HA, segment 6 ZsGreen virus infected (green) and uninfected (grey) cells represented as a histogram. (FIG. 6E) A quantification of the fold induction of fluorescence in infected cells, over uninfected cells, caused by the segment 4 NA/HA, segment 6 ZsGreen virus. (FIG. 6F) Diagram of the H1/H3 dual HA virus expressing both the subtype 1 HA and NA from the genomic segment 4, and the subtype 3 HA from the genomic segment 6. (FIG. 6G) Endpoint titer of the segment 4 NA/HA, segment 6 A/Hong Kong/1968 HA virus compared to wild-type PR8 after 72 hr incubation in 11-day old eggs. (FIG. 6H) Multicycle growth curve of the H1/H3 virus compared to wild-type PR8 after incubation in 11-day old eggs. (FIG. 6I) Subtype specific antibody staining of PR8, X31, and H1/H3 virus plaques.

FIG. 9 shows infection with the live-attenuated H1/H3 dual HA virus generates high levels of neutralizing antibodies against PR8 and X31. (FIGS. 9E-F) H1 (FIG. 9E) or H3 (FIG. 9F) specific ELISA using sera from infected mice that received the highest dose of each strain and survived (PR8: 10^1, H1/H3 dual HA: 10^5). (FIGS. 9G-H) HAI assays with subtype 1 (PR8; FIG. 9G) and 3 (X31; FIG. 9H) HA viruses with pooled RDE treated sera from mice that received the highest dose of infection and survived (PR8: 10^1, H1/H3 dual HA: 10^5). (FIGS. 9I-J) Plaque reduction assays with PR8 (FIG. 9I) or X31 (FIG. 9J) using pooled RDE treated sera from infected mice diluted 1:25. For all panels *p≤0.05, **p≤0.001.

FIG. 10 shows vaccination with inactivated H1/H3 dual HA virus generates high levels of protective antibodies against PR8 and X31. (FIGS. 10A-B) H1 (FIG. 10A) or H3 (FIG. 10B) specific ELISA from vaccinated mouse serum. (FIG. 10C) Neutralization of the H1/H3 dual HA influenza virus with polyclonal mouse sera raised against H1, H3, or H1/H3 expressing viruses. (FIGS. 10D-E) HAI assays with subtype 1 (PR8; FIG. 10D) and 3 (X31; FIG. 10E) HA viruses with pooled RDE treated sera from vaccinated mice. (FIGS. 10F-G) Plaque reduction assays with PR8 (FIG. 10F) or X31 (FIG. 10G) using pooled RDE treated sera from vaccinated mice diluted 1:25. (FIGS. 10H-I) Challenge experiments with X31 (FIG. 10H) or PR8 (FIG. 10I) in mice receiving inactivated PR8 or H1/H3 dual HA vaccination. For all panels *p≤0.05, **p≤0.001.

FIG. 11 shows plaque reduction assays performed with sera from vaccinated mice. Plaque reduction assays were repeated at a dilution 2× higher (1:50) than that reported in FIGS. 10F & 10G against the PR8 (H1N1) virus (FIG. 11A) and X31 (H3N2) virus (FIG. 11B).

FIG. 12 shows weight-loss and survival curves from X31 and PR8 challenges of vaccinated mice. Mice were vaccinated with 7 µg of protein from concentrated samples of either inactivated PR8 WT, X31 or Bivalent virus. After 2 weeks mice were boosted and then challenged with the H3N2 strain X31 (FIGS. 12A, C, & E) or the H1N1 strain PR8 (FIGS. 12B, D, & F). Each cage of mice (n≥4) was weighed daily for 14 days and the average percent weight-loss was recorded.

FIG. 13 shows dual HA viruses can be generated with a variety of HA proteins and are antigenically stable during growth in eggs. (FIG. 13F) Comparison of the parental A/Fujian/411/2002 sequence with the dual HA virus after growth in eggs, along with previously published reports of mutations that occur in the HA of A/Fujian/411/2002 which are required to allow egg growth.

FIG. 14 shows dual HA viruses using modern H3 HA exhibit similar growth kinetics and HA content to egg-adapted dual HA viruses. (FIG. 14A) HA assay of A/Victoria/210/09 expressing dual HA virus as compared to A/Hong Kong/1968 dual HA. (FIG. 14B) Growth kinetics in 11-day-old eggs of A/Victoria/210/2009 expressing dual HA virus as compared to the A/Hong Kong/1968 dual HA virus.

FIG. 15 shows delivery of a TmZsGreen polypeptide into an influenza virus. (FIG. 15A) A schematic showing the TmZsGreen polypeptide introduced into segment 4 of an influenza virus. (FIG. 15B) A schematic showing the TmZsGreen polypeptide introduced into segment 6 of an influenza virus and a segment 4 encoding both the NA and HA proteins. (FIG. 15C) A diagram showing GFP incorporated onto the surface of a viral particle. (FIG. 15D) Images showing the fluorescence of concentrated viral particles from WT PR8 or rescued viruses including ZsGreen or TmZsGreen.

FIG. 16 shows antigen packaging and delivery in engineered influenza viruses. (FIG. 16A) Images showing the fluorescence of concentrated viral particles from either concentrated TmZsGreen or WT stocks. (FIG. 16B) Quantification of the average pixel intensity from images displayed in FIG. 15A using ImageJ software. (FIG. 16D) The chromatogram from Sanger sequencing of segment 6 from the virus.

FIG. 17 shows an annotated polynucleotide including NA-Furin-2A-mNeon Sequence in Segment 6 (SEQ ID NO: 44).

FIG. 18 shows an annotated polynucleotide including mRuby2-2A-HA in Segment 4 (SEQ ID NO: 45). The ORF of the HA protein starts immediately after the PTV-2A site. The first 16 amino acids of this ORF comprise the naturally encoded signal peptide sequence. The 5' packaging signals normally encoded in the first 48 nucleotides of the HA ORF have been silently mutated and are indicated by capital letters following the atg immediately after the PTV-2A site.

FIG. 19 shows an annotated polynucleotide including NA-Furin-2A-HA in Segment 4 (SEQ ID NO: 46). The ORF of the HA protein starts immediately after the PTV-2A site. The first 16 amino acids of this ORF comprise the naturally encoded signal peptide sequence. The 5' packaging signals normally encoded in the first 48 nucleotides of the HA ORF have been silently mutated and are indicated by capital letters following the atg immediately after the PTV-2A site.

FIG. 20 shows an annotated polynucleotide including ZsGreen in Segment 6 (SEQ ID NO: 47).

FIG. 21 shows an annotated polynucleotide including Hong Kong 68 HA in Segment 6 (SEQ ID NO: 48).

FIG. 22 shows an annotated polynucleotide including Puerto Rico 8 HA in Segment 6 (SEQ ID NO: 49).

FIG. 23 shows an annotated polynucleotide including Malaysia 04 HA in Segment 6 (SEQ ID NO: 50). Notably, the packaging signals did not need to be mutated for this construct since Influenza A viruses and Influenza B viruses do not reassert. Thus, their packaging signals do not interfere with one another.

FIG. 24 shows an annotated polynucleotide including Yamagata 88 HA in Segment 6 (SEQ ID NO: 51). Notably, the packaging signals did not need to be mutated for this construct since Influenza A viruses and Influenza B viruses do not reassert. Thus, their packaging signals do not interfere with one another.

FIG. 25 shows an annotated polynucleotide including Fujian 2002 HA in Segment 6 (SEQ ID NO: 52).

FIG. 26 shows an annotated polynucleotide including Victoria 2009 HA in Segment 6 (SEQ ID NO: 53).

FIG. 27 shows an annotated polynucleotide including Transmembrane ZsGreen in Segment 4 with the HA Protein (SEQ ID NO: 54). The ORF of the HA protein starts immediately after the PTV-2A site. The first 16 amino acids of this ORF comprise the naturally encoded signal peptide sequence. The 5' packaging signals normally encoded in the first 48 nucleotides of the HA ORF have been silently mutated and are indicated by capital letters following the atg immediately after the PTV-2A site.

FIG. 28 shows an annotated polynucleotide including Zika Full Length E in Segment 6 (SEQ ID NO: 55). Only the last 33 amino acids of the Zika prM protein have been encoded in this construct to ensure proper folding of the E protein.

DETAILED DESCRIPTION

Figure 1D:
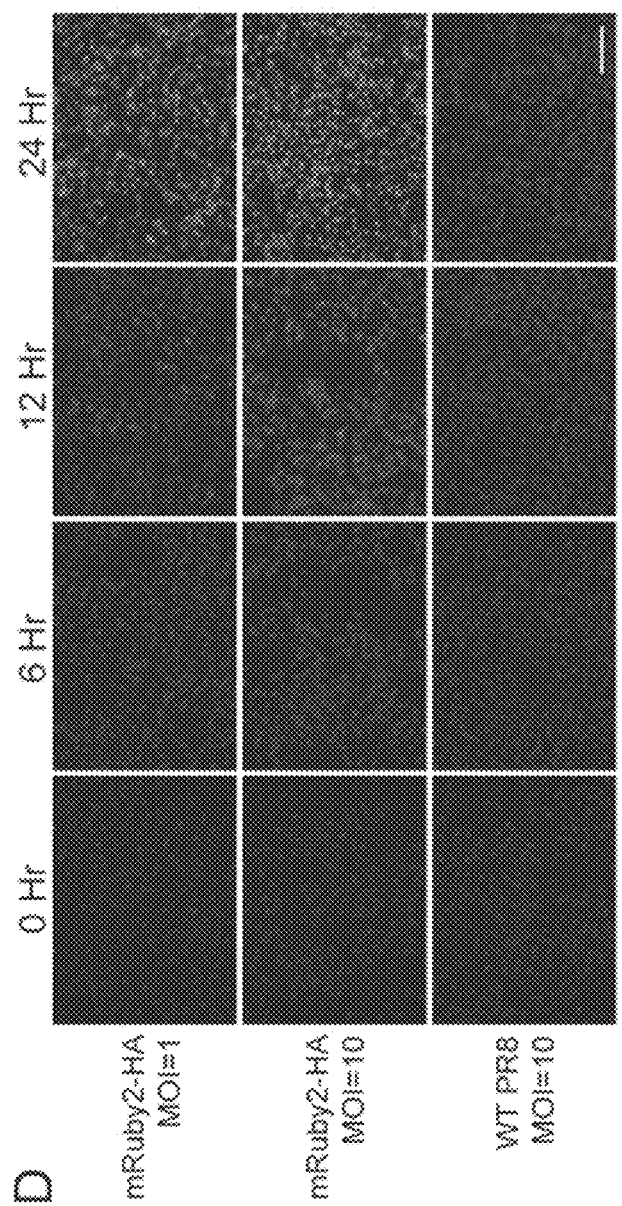
(FIG. 1D) Fluorescent microscopy timecourse of a single cycle infection on MDCK cells comparing red fluorescence between wild-type and mRuby2-HA viruses.

Here, in the non-limiting Examples, the present inventors have developed replication competent engineered influenza viruses having, for example, a modified segment 4 and/or segment 6 that include at least one additional polynucleotide encoding a heterologous polypeptide. The present inventors contemplate that such engineered influenza viruses may be useful in several applications including, without limitation, the development of dual hemagglutinin (HA) viruses that may improve the production of current influenza vaccines and/or may lead to the generation of a more universal influenza vaccine, the development of new diagnostic assays for confirming the rescue of recombinant influenza viruses, and the development of influenza viruses as a platform for delivering antigens other than influenza antigens.

For example, with respect to dual HA influenza viruses, influenza virus vaccine production is currently limited by the ability to grow circulating human strains in chicken eggs or in cell culture. To facilitate cost-effective growth, vaccine strains are serially passaged under production conditions, which frequently results in mutations of the major antigenic protein, the viral hemagglutinin (HA). Human vaccination with an antigenically drifted strain is known to contribute to poor vaccine efficacy. To address this problem, in the non-limiting Examples, the present inventors developed a replication competent influenza A virus (IAV) with an artificial genomic organization that allowed the incorporation of two independent and functional HA proteins with different growth requirements onto the same virion. Vaccination with these viruses induced protective immunity against both strains from which the HA proteins were derived, and the magnitude of the response was as high, or higher than, vaccination with either of the monovalent parental strains alone. Dual HA viruses also displayed remarkable antigenic stability; even when using an HA protein known to be highly unstable during growth in eggs, we observed high titer virus amplification without a single adaptive mutation. Thus, the viral genomic design described herein can be used to grow influenza virus vaccines to high titers without introducing antigenic mutations.

Engineered Influenza Virus Segment 4 and Segment 6 Polynucleotides

In one aspect of the present invention, engineered influenza virus segment 4 polynucleotides are provided. The engineered influenza virus segment 4 polynucleotides may include a first polynucleotide encoding a first hemagglutinin (HA) polypeptide and a second polynucleotide encoding a heterologous polypeptide, wherein the first polynucleotide is linked to the second polynucleotide by a detachable linker. Alternatively, the engineered influenza virus segment 4 polynucleotides may include a first polynucleotide encoding a first hemagglutinin (HA) polypeptide and a second polynucleotide encoding a first neuraminidase (NA) polypeptide, wherein the first polynucleotide is linked to the second polynucleotide by a detachable linker. The first polynucleotide may be either 5' or 3' to the second polynucleotide. In some embodiments, the engineered influenza virus segment 4 polynucleotides may include a first polynucleotide encoding a heterologous polypeptide.

In another aspect of the present invention, engineered influenza virus segment 6 polynucleotides are provided. The engineered influenza virus segment 6 polynucleotides may include a first polynucleotide encoding a first neuraminidase (NA) polypeptide and a second polynucleotide encoding a heterologous polypeptide, wherein the first polynucleotide is linked to the second polynucleotide by a detachable linker. Alternatively, the engineered influenza virus segment 6 polynucleotides may include a first polynucleotide encoding a first hemagglutinin (HA) polypeptide and a second polynucleotide encoding a first neuraminidase (NA) polypeptide, wherein the first polynucleotide is linked to the second polynucleotide by a detachable linker. The first polynucleotide may be either 5' or 3' to the second polynucleotide. In some embodiments, the engineered influenza virus segment 6 polynucleotides may include a first polynucleotide encoding a heterologous polypeptide.

Optionally, the engineered influenza virus segment 4 polynucleotides and/or the engineered influenza virus segment 6 polynucleotides may further include additional polynucleotides typically found in segment 4 and/or segment 6 of influenza viruses that are known in the art. Such additional polynucleotides may include, without limitation, polynucleotides encoding an influenza virus packaging signal. As used herein, an "influenza virus packaging signal" refers to any cis-acting sequence or sequences that are required to ensure that each influenza virion has a full complement of the influenza genome. Influenza virus packaging signal(s) have been identified for each influenza A virus segment. See, e.g., Gao et al., *J. Virol.* 86:7043-7051 (2012). A suitable influenza virus packaging signal for engineered influenza virus segment 4 polynucleotides may include, without limitation, SEQ ID NO: 1 and SEQ ID NO: 2. Preferably, the engineered influenza virus segment 4 polynucleotides and/or the engineered influenza virus segment 6 polynucleotides described herein are flanked by appropriate influenza virus packaging signals. For example, the engineered influenza virus segment 4 polynucleotides described herein may include at the 5' end the polynucleotide of SEQ ID NO: 1 or a polynucleotide having at least 60%, 65%, 70%, 75%, 80%, 85%, 90%, 95%, 98%, or 99% sequence identity to SEQ ID NO: 1 and may include at the 3' end the polynucleotide of SEQ ID NO: 2 or a polynucleotide having at least 60%, 65%, 70%, 75%, 80%, 85%, 90%, 95%, 98%, or 99% sequence identity to SEQ ID NO: 2.

A suitable influenza virus packaging signal for engineered influenza virus segment 6 polynucleotides may include, without limitation, SEQ ID NO: 42 and SEQ ID NO: 43. For example, the engineered influenza virus segment 6 polynucleotides described herein may include at the 5' end the polynucleotide of SEQ ID NO: 42 or a polynucleotide having at least 60%, 65%, 70%, 75%, 80%, 85%, 90%, 95%, 98%, or 99% sequence identity to SEQ ID NO: 42 and may include at the 3' end the polynucleotide of SEQ ID NO: 43 or a polynucleotide having at least 60%, 65%, 70%, 75%, 80%, 85%, 90%, 95%, 98%, or 99% sequence identity to SEQ ID NO: 43.

As used herein, the terms "polynucleotide," "polynucleotide sequence," "nucleic acid" and "nucleic acid sequence" refer to a nucleotide, oligonucleotide, polynucleotide (which terms may be used interchangeably), or any fragment thereof. These phrases also refer to DNA or RNA of natural or synthetic origin (which may be single-stranded or double-stranded and may represent the sense or the antisense strand or the positive strand or the negative strand). In some embodiments, the engineered influenza virus segment 4 and segment 6 polynucleotides disclosed herein are DNA. In some embodiments, the engineered influenza virus segment 4 and segment 6 polynucleotides disclosed herein are single-stranded negative RNA.

The polynucleotides disclosed herein may "encode" a particular polypeptide or a particular cis-regulatory sequence. As used herein, the term "encode" is used in the broadest sense to refer to any sequence that may ultimately give rise to a noted polypeptide or cis-regulatory sequence. Thus, as mentioned above, the polynucleotide may be single-stranded or double-stranded and may represent the sense or the antisense strand or the positive strand or the negative strand.

The polynucleotides provided herein may be prepared by methods available to those of skill in the art. Notably each of the polynucleotides claimed are recombinant molecules and as such do not occur in nature. Generally, the nomenclature used herein and the laboratory procedures utilized in the present invention include molecular, biochemical, and recombinant DNA techniques that are well known and commonly employed in the art. Standard techniques available to those skilled in the art may be used for cloning, DNA and RNA isolation, amplification and purification. Such techniques are thoroughly explained in the literature.

As used herein, a "polypeptide" or "protein" or "peptide" may be used interchangeably to refer to a polymer of amino acids. A "protein" as contemplated herein typically comprises a polymer of naturally occurring amino acids (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine).

A "hemagglutinin (HA) polypeptide" refers to the glycoprotein found on the surface of influenza viruses. The HA polypeptide may be any of HA subtypes including, without limitation, H1 through H18. Suitably, the HA polypeptide may be an H1, H2, H3, or H5 subtype. 1. In some embodiments, the HA polypeptide may include an HA signal polypeptide at the N-terminus. The HA signal polypeptide may include the polypeptide of SEQ ID NO: 5 or a polypeptide having at least 70%, 75%, 80%, 85%, 90%, 95%, or 99% sequence identity to SEQ ID NO: 5. An exemplary HA polynucleotide sequence is provided in FIG. 19 and SEQ ID NO: 46 as the underlined sequence in plain text. Other HA polynucleotides are known to those skilled in the art and may be used instead of the sequence provided.

A "neuraminidase (NA) polypeptide" refers the enzymatic protein found on the surface of influenza viruses. The NA polypeptide may be any of the NA subtypes including, without limitation, N1 through N9. Suitably, the NA polypeptide may be an N1, N2, N3, or N7. An exemplary Neuraminadase polynucleotide sequence is provided in FIG. 19 and SEQ ID NO: 46 as the underlined sequence in bold text. Other NA polynucleotides are known to those skilled in the art and may be used instead of the sequence provided.

As used herein, a "heterologous polypeptide" refers to a polypeptide that is not found in an influenza virus in nature. The heterologous polypeptide may be a foreign polypeptide not found in an influenza virus in nature or may be a polypeptide that is found in an influenza virus in nature (i.e., PB2, PB1, PA, HA, NP, NA, M, and NS) but represents an additional version of the influenza polypeptide. Suitable heterologous polypeptides may include, without limitation, fluorescent polypeptides, antigenic polypeptides, HA polypeptides, or NA polypeptides. In some embodiments, the heterologous polypeptide may be localized on the surface of an influenza virus by including, without limitation, a transmembrane domain or signal sequence in the heterologous polynucleotide that allows the heterologous polypeptide to be expressed on the surface of an influenza virion. Suitable transmembrane domains may include, without limitation, a transmembrane domain of an influenza neuraminidase (NA) polypeptide or a transmembrane domain of an influenza hemagglutinin (HA) polypeptide.

The polynucleotides encoding the heterologous polypeptides described herein may be optimized for the codon usage of the specific Influenza (i.e., Influenza A or B) that the polynucleotides are being expressed in. Influenza viruses have low GC content and preferentially utilize different codons than standard eukaryotes. Thus, to enhance expression and stability of desired polynucleotides, the polynucleotides may be optimized using the publicly available Codon Optimization On-Line (COOL) or OPTIMIZER tool. For example, codon usage of the Influenza A virus may be determined using the following table (Table 1) from the Codon Usage Database.

phosphodiester bond and may be linked to allow translation of both encoded polypeptides which are then linked by peptide bonds to form a fusion protein. The polynucleotides or polypeptides may be linked via a linker.

As used herein, a "detachable linker" refers to a chemical entity that is capable of linking the first polynucleotide to the second polynucleotide but, when translated, results in a polypeptide encoded by the first polynucleotide that is not linked to the polypeptide encoded by the second polynucleotide. In some embodiments, the detachable linker may leave at least one additional amino acid on either the polypeptide encoded by the first polynucleotide or the polypeptide encoded by the second polynucleotide or both. In preferred embodiments, the detachable linker does not leave any additional amino acids on the polypeptide encoded by the first polynucleotide or the polypeptide encoded by the second polynucleotide.

The detachable linker may include a self-cleaving 2A polypeptide. Self-cleaving 2A polypeptides are known in the art as described, for example, in Kim, J. H. et al., PLOS ONE, 6(4), e18556. Suitable self-cleaving 2A polypeptides may include, without limitation, FMDV 2A, equine rhinitis A virus (ERAV) 2A (E2A), porcine teschovirus-1 2A (PTV1-2A), and Thoseaasigna virus 2A (T2A). Preferably, the self-cleaving 2A polypeptide includes a porcine teschovirus 2A (PTV1-2A) motif such as found in SEQ ID NO: 4 or a

TABLE 1

| UUU | 17.8 | (293396) | UCU | 12.8 | (210832) | UAU | 14.2 | (233240) | UGU | 7.6 | (125361) |
|-----|------|----------|-----|------|----------|-----|------|----------|-----|------|----------|
| UUC | 20.2 | (332322) | UCC | 11.0 | (181613) | UAC | 12.6 | (207199) | UGC | 11.2 | (184026) |
| UUA | 8.1 | (133967) | UCA | 19.0 | (312168) | UAA | 1.2 | (19221) | UGA | 0.8 | (12569) |
| UUG | 14.6 | (240030) | UCG | 3.8 | (61962) | UAG | 0.5 | (8905) | UGG | 16.4 | (270035) |
| CUU | 16.8 | (276221) | CCU | 11.3 | (185417) | CAU | 9.9 | (162471) | CGU | 2.0 | (33533) |
| CUC | 12.2 | (200260) | CCC | 7.3 | (119819) | CAC | 7.2 | (118729) | CGC | 3.2 | (52445) |
| CUA | 13.3 | (219434) | CCA | 14.7 | (242107) | CAA | 22.5 | (371086) | CGA | 6.1 | (99775) |
| CUG | 14.8 | (243631) | CCG | 4.7 | (76633) | CAG | 18.4 | (302804) | CCC | 5.6 | (91717) |
| AUU | 23.7 | (389594) | ACU | 18.3 | (301672) | AAU | 31.3 | (515196) | AGU | 14.4 | (237994) |
| AUC | 18.1 | (298586) | ACC | 13.2 | (217249) | AAC | 23.5 | (387110) | AGC | 15.3 | (252010) |
| AUA | 24.4 | (402080) | ACA | 27.7 | (455971) | AAA | 35.9 | (591384) | AGA | 31.7 | (521693) |
| AUG | 37.8 | (622324) | ACG | 4.9 | (80019) | AAG | 22.2 | (365188) | ACG | 18.2 | (299901) |
| GUU | 13.4 | (220590) | GCU | 15.4 | (254219) | GAU | 26.1 | (429380) | GGU | 9.9 | (162838) |
| GUC | 11.1 | (183609) | GCC | 12.6 | (207403) | GAC | 20.2 | (332513) | GGC | 9.0 | (148927) |
| CUA | 12.5 | (205254) | GCA | 24.2 | (398856) | GAA | 40.5 | (667159) | GGA | 29.8 | (491304) |
| GUG | 19.6 | (323574) | CCG | 4.5 | (74308) | GAG | 31.2 | (513739) | GGG | 18.1 | (298542) |

Coding GC 43.85% 1st letter GC 46.79% 2nd letter GC 40.45% 3rd letter GC 44.30%

Fluorescent polypeptides may be any polypeptides that emit light when exposed to light and may include, without limitation, zsGreen, mRuby, mCherry, green fluorescent proteins (GFPs) and GFP variants, yellow fluorescent proteins (YFPs), red fluorescent proteins (RFPs), DsRed fluorescent proteins, far-red fluorescent proteins, orange fluorescent proteins (OFPs), blue fluorescent proteins (BFPs), cyan fluorescent protein (CFPs), Kindling red protein, or JRed. A fluorescent polypeptide may be chosen based on its excitation and emission properties which are available to those skilled in the art.

Antigenic polypeptides may be any polypeptides that may serve as antigens. Suitable antigenic polypeptides may include, without limitation, zika virus polypeptides, polypeptides from viruses such as alphaviruses and flaviviruses, or surface exposed bacterial epitopes such as flagellin.

In accordance with the present invention, the first polynucleotide may be linked to the second polynucleotide by a detachable linker. As used herein, the phrase "linked to" refers to being chemically bonded together. Preferably, the chemical bond is a covalent bond. In dealing with linked polynucleotides, the polynucleotides may be linked by a polypeptide having at least 70%, 75%, 80%, 85%, 90%, 95%, or 99% sequence identity to SEQ ID NO: 4.

In some embodiments, the detachable linker may further include a polynucleotide encoding a protease motif located 5' to the polynucleotide encoding the self-cleaving 2A polypeptide. The protease motif may include, without limitation, a furin site; a recognition site for other proprotein convertases such as PC2, PC4, PC5/6, PC7, and PACE4; or a TEV cleavage site. The furin site may include the polypeptide of SEQ ID NO: 3 or a polypeptide having at least 70%, 75%, 80%, 85%, 90%, 95%, or 99% sequence identity to SEQ ID NO: 3.

In some embodiments, the engineered influenza virus segment 4 polynucleotides and/or the engineered influenza virus segment 6 polynucleotides may include any one of the polynucleotides of SEQ ID NOS: 44-55 or a polynucleotide having at least 70%, 75%, 80%, 85%, 90%, 95%, or 99% sequence identity to one of SEQ ID NOS: 44-55. See also FIGS. 17-28.

Plasmids

In a further aspect of the present invention, plasmids are provided. The plasmids may include any one of the engineered influenza virus segment 4 polynucleotides or the engineered influenza virus segment 6 polynucleotides described herein. Suitably, the plasmids may include any one of the engineered influenza virus segment 4 DNA polynucleotides or the engineered influenza virus segment 6 DNA polynucleotides described herein. As used herein, a "plasmid" refers to a circular double-stranded DNA loop into which additional DNA segments may be ligated. Suitable plasmids may include, without limitation, plasmids typically used to rescue influenza viruses in cells such as plasmids used in the 12 plasmid and 8 plasmid reverse genetic systems well-known in the art. See, e.g., Neumann et al., PNAS 96:9345-9350 (1999); Fodor et al., J. Virol. 73:9679-9682 (1999); Hoffmann et al., PNAS 97:6108-6113 (2000); Hoffmann et al., Virology 267:310-317 (2000). Preferably, the plasmid is a pDZ plasmid used with 8 plasmid reverse genetic systems.

The pDZ plasmid is an ambisense plasmid including a human RNA polymerase I promoter and a terminator sequence that controls the expression of the negative sense viral RNA. In an opposite orientation to this viral RNA unit, the viral proteins from the same viral RNA genes are expressed using a chicken β-action promoter and polyA sequence.

Plasmid Compositions

In a still further aspect of the present invention, plasmid compositions are provided. The plasmid compositions may include plasmids encoding influenza virus segments 1, 2, 3, 5, 6, 7, and 8 and a plasmid including any one of the engineered influenza virus segment 4 polynucleotide described herein including a first polynucleotide encoding a first hemagglutinin (HA) polypeptide and a second polynucleotide encoding a heterologous polypeptide, wherein the first polynucleotide is linked to the second polynucleotide by a detachable linker.

Plasmids for encoding the eight segments of influenza viruses are known in the art. For example, eight pDZ plasmids are available that each encode influenza virus segment 1 (PB2), segment 2 (PB1), segment 3 (PA), segment 4 (HA), segment 5 (NP), segment 6 (NA), segment 7 (M), and segment 8 (NS).

The plasmid compositions may include plasmids encoding influenza virus segments 1, 2, 3, 4, 5, 7, and 8 and a plasmid including any one of the engineered influenza virus segment 6 polynucleotides described herein including a first polynucleotide encoding a first neuraminidase (NA) polypeptide and a second polynucleotide encoding a heterologous polypeptide, wherein the first polynucleotide is linked to the second polynucleotide by a detachable linker.

The plasmid compositions may include plasmids encoding influenza virus segments 1, 2, 3, 5, 6, 7, and 8 and a plasmid including any one of the engineered influenza virus segment 4 polynucleotides described herein including a first polynucleotide encoding a first hemagglutinin (HA) polypeptide and a second polynucleotide encoding a first neuraminidase (NA) polypeptide, wherein the first polynucleotide is linked to the second polynucleotide by a detachable linker.

The plasmid compositions may include plasmids encoding influenza virus segments 1, 2, 3, 4, 5, 7, and 8 and a plasmid including any one of the engineered influenza virus segment 6 polynucleotides described herein including a first polynucleotide encoding a first hemagglutinin (HA) polypeptide and a second polynucleotide encoding a first neuraminidase (NA) polypeptide, wherein the first polynucleotide is linked to the second polynucleotide by a detachable linker.

The plasmid compositions may include plasmids encoding influenza virus segments 1, 2, 3, 5, 7, and 8, a plasmid including any one of the engineered influenza virus segment 4 polynucleotides described herein including a first polynucleotide encoding a first hemagglutinin (HA) polypeptide and a second polynucleotide encoding a first neuraminidase (NA) polypeptide, wherein the first polynucleotide is linked to the second polynucleotide by a detachable linker, and a plasmid including any one of the engineered influenza virus segment 6 polynucleotides described herein including a first polynucleotide encoding a heterologous polypeptide.

The plasmid compositions may include plasmids encoding influenza virus segments 1, 2, 3, 5, 7, and 8, a plasmid including any one of the engineered influenza virus segment 4 polynucleotides described herein including a first polynucleotide encoding a heterologous polypeptide, and a plasmid including any one of the engineered influenza virus segment 6 polynucleotides described herein including a first polynucleotide encoding a first hemagglutinin (HA) polypeptide and a second polynucleotide encoding a first neuraminidase (NA) polypeptide, wherein the first polynucleotide is linked to the second polynucleotide by a detachable linker.

Engineered Influenza Viruses

In another aspect of the present invention, engineered influenza viruses are provided. The engineered influenza viruses may include any one of the engineered influenza virus segment 4 polynucleotides or the engineered influenza virus segment 6 polynucleotides described herein. Suitably, the engineered influenza viruses may include any one of the engineered influenza virus segment 4 single-stranded negative RNA polynucleotides or the engineered influenza virus segment 6 single-stranded negative RNA polynucleotides described herein. The engineered viruses may also include both the engineered influenza virus segment 4 polynucleotide and the engineered influenza virus segment 6 polynucleotides described herein.

The engineered influenza viruses may be either an influenza A virus or an influenza B virus. Preferably, the engineered influenza viruses described herein are replication-competent. In some embodiments, the engineered influenza virus may be attenuated or inactivated following replication.

As well known in the art, influenza viruses include a ribonucleoprotein (RNP) complex composed of 8 single-stranded negative RNA viral gene segments (PB2, PB1, PA, HA, NP, NA, M, and NS) encapsidated by the viral nucleoprotein—NP. Surrounding the RNP complex is a lipid bilayer containing the two viral glycoproteins—HA and NA.

The engineered influenza viruses may include influenza virus segments 1, 2, 3, 5, 6, 7, and 8 and a polynucleotide including any one of the engineered influenza virus segment 4 single-stranded negative RNA polynucleotides described herein including a first polynucleotide encoding a first hemagglutinin (HA) polypeptide and a second polynucleotide encoding a heterologous polypeptide, wherein the first polynucleotide is linked to the second polynucleotide by a detachable linker.

The engineered influenza viruses may include influenza virus segments 1, 2, 3, 4, 5, 7, and 8 and a polynucleotide including any one of the engineered influenza virus segment 6 single-stranded negative RNA polynucleotides described herein including a first polynucleotide encoding a first neuraminidase (NA) polypeptide and a second polynucleotide encoding a heterologous polypeptide, wherein the first polynucleotide is linked to the second polynucleotide by a detachable linker.

The engineered influenza viruses may include influenza virus segments 1, 2, 3, 5, 6, 7, and 8 and a polynucleotide including any one of the engineered influenza virus segment 4 single-stranded negative RNA polynucleotides described herein including a first polynucleotide encoding a first hemagglutinin (HA) polypeptide and a second polynucleotide encoding a first neuraminidase (NA) polypeptide, wherein the first polynucleotide is linked to the second polynucleotide by a detachable linker.

The engineered influenza viruses may include influenza virus segments 1, 2, 3, 4, 5, 7, and 8 and a polynucleotide including any one of the engineered influenza virus segment 6 single-stranded negative RNA polynucleotides described herein including a first polynucleotide encoding a first hemagglutinin (HA) polypeptide and a second polynucleotide encoding a first neuraminidase (NA) polypeptide, wherein the first polynucleotide is linked to the second polynucleotide by a detachable linker.

The engineered influenza viruses may include influenza virus segments 1, 2, 3, 5, 7, and 8, a polynucleotide including any one of the engineered influenza virus segment 4 single-stranded negative RNA polynucleotides described herein including a first polynucleotide encoding a first hemagglutinin (HA) polypeptide and a second polynucleotide encoding a first neuraminidase (NA) polypeptide, wherein the first polynucleotide is linked to the second polynucleotide by a detachable linker, and a polynucleotide including any one of the engineered influenza virus segment 6 single-stranded negative RNA polynucleotides described herein including a first polynucleotide encoding a heterologous polypeptide.

The engineered influenza viruses may include influenza virus segments 1, 2, 3, 5, 7, and 8, a polynucleotide including any one of the engineered influenza virus segment 4 single-stranded negative RNA polynucleotides described herein including a first polynucleotide encoding a heterologous polypeptide, and a polynucleotide including any one of the engineered influenza virus segment 6 single-stranded negative RNA polynucleotides described herein including a first polynucleotide encoding a first hemagglutinin (HA) polypeptide and a second polynucleotide encoding a first neuraminidase (NA) polypeptide, wherein the first polynucleotide is linked to the second polynucleotide by a detachable linker.

The engineered influenza virus may include a first polynucleotide encoding a first hemagglutinin (HA) polypeptide and a second polynucleotide encoding a second HA polypeptide, wherein the virus includes eight segments, an unmodified PB1 protein, and is replication-competent. In some embodiments, the first HA polypeptide and the second HA polypeptide may include an HA subtype 1 (HA1) polypeptide or an HA subtype 3 (HA3) polypeptide. In some embodiments, the first HA polypeptide may include an HA subtype 1 (HA1) polypeptide and the second HA polypeptide may include an HA subtype 3 (HA3) polypeptide. In some embodiments, the engineered influenza virus may include unmodified versions of al influenza viral proteins (PB2, PB1, PA, NP, NA, M, and NS) and may include first and second HA polypeptides that are unmodified.

As used herein, an "unmodified" protein refers to a polypeptide that does not include any additional amino acids at either the N-terminus or the C-terminus of the polypeptide from, for example, a detachable linker. For example, an "unmodified" PB1 protein refers to an influenza PB1 protein that does not include any additional amino acids at either the N-terminus or the C-terminus of the PB1 protein from, for example, a detachable linker.

The engineered influenza virus may include a heterologous polynucleotide encoding a heterologous polypeptide, wherein the virus comprises eight segments, unmodified versions of all influenza viral proteins (PB2, PB1, PA, HA, NP, NA, M, and NS), and is replication-competent. The engineered influenza virus may include at least two distinct HA polypeptides, wherein the virus is replication-competent.

Engineered Influenza Virus Compositions and Vaccine Compositions

In another aspect of the present invention, compositions including engineered influenza viruses are provided. The compositions may include any one of the engineered influenza viruses described herein.

In a further aspect, the present invention relates to vaccine compositions including engineered influenza viruses. The vaccine composition may include any one of the engineered influenza viruses described herein and a pharmaceutically acceptable carrier and/or an adjuvant.

The vaccine compositions may include a pharmaceutical carrier, excipient, or diluent, which are nontoxic to the cell or subject being exposed thereto at the dosages and concentrations employed. Often a pharmaceutical diluent is in an aqueous pH buffered solution. Examples of pharmaceutical carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ brand surfactant, polyethylene glycol (PEG), and PLURONICS™ surfactant.

The vaccine compositions described herein may include adjuvants to increase immunogenicity of the composition. The adjuvant may be any of the currently FDA-licensed adjuvants for influenza vaccine usage including, without limitation, aluminum salt (alum) and the squalene oil-in-water emulsion systems MF59 (Wadman 2005 (Novartis)) and AS03 (GlaxoSmithKline).

In some embodiments, these compositions comprise one or more of a mineral adjuvant, gel-based adjuvant, tensoactive agent, bacterial product, oil emulsion, particulated adjuvant, fusion protein, and lipopeptide. Mineral salt adjuvants include aluminum adjuvants, salts of calcium (e.g. calcium phosphate), iron and zirconium. Gel-based adjuvants include aluminum gel-based adjuvants and acemannan. Tensoactive agents include Quil A, saponin derived from an aqueous extract from the bark of *Quillaja saponaria*; saponins, tensoactive glycosides containing a hydrophobic nucleus of triterpenoid structure with carbohydrate chains linked to the nucleus, and QS-21. Bacterial products include cell wall peptidoglycan or lipopolysaccharide of Gram-negative bacteria (e.g. from *Mycobacterium* spp., *Corynebacterium parvum, C. granulosum, Bordetella pertussis* and *Neisseria meningitidis*), N-acetyl muramyl-L-alanyl-D-isoglutamine (MDP), different compounds derived from MDP (e.g. threonyl-MDP), lipopolysaccharides (LPS) (e.g. from the cell wall of Gram-negative bacteria), trehalose dimycolate (TDM), cholera toxin or other bacterial toxins, and DNA containing CpG motifs. Oil emulsions include FIA, Montanide, Adjuvant 65, Lipovant, the montanide family of oil-based adjuvants, and various liposomes. Among particulated and polymeric systems, poly (DL-lactide-coglycolide)

microspheres have been extensively studied and find use herein. Notably, several of the delivery particles noted above may also act as adjuvants.

In some embodiments, the vaccine compositions further include cytokines (e.g. IFN-γ, granulocyte-macrophage colony stimulating factor (GM-CSF) IL-2, or IL-12) or immunostimulatory molecules such as FasL, CD40 ligand or a toll-like receptor agonist, or carbohydrate adjuvants (e.g. inulin-derived adjuvants, such as, gamma inulin, algammulin, and polysaccharides based on glucose and mannose, such as glucans, dextrans, lentinans, glucomannans and galactomannans). In some embodiments, adjuvant formulations are useful in the present invention and include alum salts in combination with other adjuvants such as Lipid A, algammulin, immunostimulatory complexes (ISCOMS), which are virus like particles of 30-40 nm and dodecahedric structure, composed of Quil A, lipids, and cholesterol.

In some embodiments, the additional adjuvants are described in Jennings et al. Adjuvants and Delivery Systems for Viral Vaccines-Mechanisms and Potential. In: Brown F, Haaheim L R, (eds). Modulation of the Immune Response to Vaccine Antigens. Dev. Biol. Stand, Vol. 92. Basel: Karger 1998; 19-28 and/or Sayers et al. J Biomed Biotechnol. 2012; 2012: 831486, and/or Petrovsky and Aguilar, Immunology and Cell Biology (2004) 82, 488-496.

In some embodiments, the adjuvant is an aluminum gel or salt, such as aluminum hydroxide, aluminum phosphate, and potassium aluminum sulfate, AS04 (which is composed of aluminum salt and MPL), and ALHYDROGEL. In some embodiments, the aluminum gel or salt is a formulation or mixture with any of the additional adjuvants described herein.

In some embodiments, pharmaceutical compositions include oil-in-water emulsion formulations, saponin adjuvants, ovalbumin, Freunds Adjuvant, cytokines, and/or chitosans. Illustrative compositions comprise one or more of the following.

(1) ovalbumin (e.g. ENDOFIT);

(2) oil-in-water emulsion formulations, with or without other specific immunostimulating agents, such as: (a) MF59 (PCT Publ. No. WO 90/14837), which may contain 5% Squalene, 0.5% Tween 80, and 0.5% Span 85 (optionally containing various amounts of MTP-PE) formulated into submicron particles, (b) SAF, containing 10% Squalane, 0.4% Tween 80, 5% pluronic-blocked polymer L121, and thr-MDP either microfluidized into a submicron emulsion or vortexed to generate a larger particle size emulsion, (c) RIBI adjuvant system (RAS), (RIBI IMMUNOCHEM, Hamilton, Mo.) containing 2% Squalene, 0.2% Tween 80, and, optionally, one or more bacterial cell wall components from the group of monophosphorylipid A (MPL), trehalose dimycolate (TDM), and cell wall skeleton (CWS), including MPL+ CWS (DETOX™); and (d) ADDAVAX (Invitrogen);

(3) saponin adjuvants, such as STIMULON (Cambridge Bioscience, Worcester, Mass.);

(4) Complete Freunds Adjuvant (CFA) and Incomplete Freunds Adjuvant (IFA);

(5) cytokines, such as interleukins (by way of non-limiting example, IL-1, IL-2, IL-4, IL-5, IL-6, IL-7, IL-12, etc.), interferons (e.g., gamma interferon), macrophage colony stimulating factor (M-CSF), tumor necrosis factor (TNF), etc;

(6) chitosans and other derivatives of chitin or poly-N-acetyl-D-glucosamine in which the greater proportion of the N-acetyl groups have been removed through hydrolysis; and (7) other substances that act as immunostimulating agents to enhance the effectiveness of the composition, e.g., monophosphoryl lipid A.

In other embodiments, adjuvants include a flagellin-based agent, an aluminium salt or gel, a pattern recognition receptors (PRR) agonist, CpG ODNs and imidazoquinolines. In some embodiments, adjuvants include a TLR agonist (e.g. TLR1, and/or TLR2, and/or TLR3, and/or TLR4, and/or TLR5, and/or TLR6, and/or TLR7, and/or TLR8, and/or TLR9, and/or TLR10, and/or TLR11, and/or TLR12, and/or TLR13), a nucleotide-binding oligomerization domain (NOD) agonist, a stimulator of interferon genes (STING) ligand, or related agent.

Suitably, the vaccines compositions described herein are capable of eliciting an immune response to an influenza virus or polypeptide thereof when administered to a subject.

In some embodiments, the compositions or vaccine compositions including engineered influenza viruses described herein may include at least $10^6$ pfu/mL, $10^7$ pfu/mL, $10^8$ pfu/mL, or $10^9$ pfu/mL.

Methods for Preventing or Reducing the Symptoms of Influenza in a Subject

In a further aspect of the present invention, methods for preventing or reducing the symptoms of influenza in a subject are provided. The methods may include administering a therapeutically effective amount of any one of the engineered influenza viruses or the compositions or vaccine compositions including engineered influenza viruses described herein to the subject to prevent or reduce the symptoms of influenza in the subject.

The subject may be any vertebrate, suitably a human, but may also include, without limitation, wild or domestic bird species such as poultry (chickens, turkeys, etc.), pigs, horses, rabbits, goats, canine, or cattle.

Exemplary influenza in accordance with the present invention include, without limitation, influenza A or influenza B.

The symptoms of influenza are well-known in the art and may include, without limitation, one or more of the following symptoms: headaches, chest discomfort, cough, sore throat, fever, aches, chills, fatigue, weakness, sneezing, or stuffy nose.

A "therapeutically effective amount" or an "effective amount" as used herein means the amount of a composition that, when administered to a subject for preventing or reducing the symptoms of influenza is sufficient to prevent or reduce the symptoms of influenza. The therapeutically effective amount will vary depending on the formulation or composition, the influenza and its severity and the age, weight, physical condition and responsiveness of the subject to be treated. Typical therapeutically effective amounts may include 5 μg, 10 μg, 15 μg, 20 μg, 25 μg, 30 μg, 35 μg, 40 μg, 45 μg, 50 μg, 55 μg, 60 μg, 65 μg, 70 μg, 75 μg or more of HA per vaccine virus strain per 0.5 mL dose.

The compositions (i.e. the engineered influenza viruses or the compositions or vaccine compositions including engineered influenza viruses described herein) may be administered by any means known to those skilled in the art, including, without limitation, intramuscular, intradermal, intranasal, oral, topical, parenteral, intravenous, subcutaneous, intrathecal, transcutaneous, nasopharyngeal, or transmucosal absorption. Thus the compositions may be formulated as an injectable, ingestable, topical, or suppository formulation.

The effective dosage amounts described herein refer to total amounts administered, that is, if more than one composition is administered, the effective dosage amounts correspond to the total amount administered. The compositions can be administered as a single dose or as divided doses. For example, the compositions may be administered two or more times separated by 4 hours, 6 hours, 8 hours, 12 hours, a day, two days, three days, four days, one week, two weeks, or by three or more weeks.

Methods for Producing an Influenza Virus

In another aspect, the present invention relates to methods for producing an influenza virus. The methods may include introducing any one of the compositions described herein (i.e., engineered influenza virus segment 4 and segment 6 polynucleotides, plasmids, plasmid compositions, engineered influenza viruses, engineered influenza virus compositions and vaccine compositions) into a cell.

As used herein, "introducing" describes a process by which exogenous polynucleotides (e.g., DNA or RNA) or viral particles are introduced into a recipient cell. Methods of introducing the disclosed polynucleotides, plasmids, and plasmid compositions into a cell are known in the art and may include, without limitation, transfection, transformation, and microinjection methods. Transformation or transfection may occur under natural or artificial conditions according to various methods well known in the art, and may rely on any known method for the insertion of foreign nucleic acid sequences into a host cell. The method for transformation or transfection is selected based on the type of host cell being transformed and may include, without limitation, lipofection, bacteriophage or viral infection, electroporation, heat shock, and particle bombardment. Microinjection of polynucleotides may also be used to introduce the disclosed polynucleotides, plasmids, and plasmid compositions into cells. In some embodiments, the disclosed polynucleotides, plasmids, and plasmid compositions may be introduced into cells using a lipofectamine-based transfection.

The disclosed engineered influenza viruses, engineered influenza virus compositions and vaccine compositions may be "introduced" into a cell by simply contacting these compositions with a cell. Delivery can be to cells (e.g. in vitro or ex vivo administration) or target tissues (e.g. in vivo administration). Suitable cells in accordance with the present invention include eukaryotic cells. Suitable eukaryotic cells include, without limitation, mammalian cells or chicken cells. The cell may be a cell in culture or may be an embryonated chicken egg. Suitable mammalian cells include, without limitation, a MDCK cell, A549 cell, a CHO cell, a HEK293 cell, a HEK293T cell, a HeLa cell, a NS0 cell, a Sp2/0 cell, a COS cell, a BK cell, a NIH3T3 cell, a FRhL-2 cell, a MRC-5 cell, a WI-38 cell, a CEF cell, a CEK cell, a DF-1 cell, or a Vero cell.

The methods for producing influenza virus may also further include additional steps used in harvesting the influenza virus from the cell. In embodiments including cells in culture, the methods may further include harvesting the supernatant of the culture by, for example, centrifugation or pipetting. In embodiments where the cell is an embryonated chicken egg, the methods may further include harvesting the allantoic fluid from the embryonated chicken egg.

The methods may also further include additional steps used in producing polypeptides recombinantly. For example, the methods may include purifying the heterologous polypeptide from the virion or the cell. The term "purifying" refers to the process of ensuring that the heterologous polypeptide is substantially or essentially free from viral or cellular components and other impurities. Purification of polypeptides is typically performed using molecular biology and analytical chemistry techniques such as polyacrylamide gel electrophoresis or high performance liquid chromatography. Methods of purifying proteins are well known to those skilled in the art. A "purified" heterologous polypeptide means that the heterologous polypeptide is at least 85% pure, more preferably at least 95% pure, and most preferably at least 99% pure.

Methods for Detecting the Presence of a Rescued Influenza Virus in a Cell

In a still further aspect, the present invention relates to methods for detecting the presence of a rescued influenza virus in a cell in a culture. The methods may include introducing any one of the plasmid compositions disclosed herein including a polynucleotide encoding a heterologous polypeptide into a cell. Suitably, the heterologous polypeptide includes a fluorescent polypeptide such as, without limitation, zsGreen, mRuby, mCherry, green fluorescent proteins (GFPs) and GFP variants, yellow fluorescent proteins (YFPs), red fluorescent proteins (RFPs), DsRed fluorescent proteins, far-red fluorescent proteins, orange fluorescent proteins (OFPs), blue fluorescent proteins (BFPs), cyan fluorescent protein (CFPs), Kindling red protein, or JRed. ZsGreen or mRuby.

The methods for detecting the presence of a rescued influenza virus in a cell in a culture may further include detecting the presence of the heterologous polypeptide in the cell or in the culture. Suitable detection methods will depend on the identity of the heterologous polypeptide and may include, without limitation, fluorescence such as by fluorescence microscopy or fluorometer, luminescence, colorimetric, optical, or acoustic detection methods.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

The following examples are meant only to be illustrative and are not meant as limitations on the scope of the invention or of the appended claims.

EXAMPLES

Example 1

Rationally Designed Influenza Virus Vaccines that are Antigenically Stable During Egg Growth Results To improve the vaccine production process, we decided to generate a replication competent IAV that incorporated two different HA proteins onto the same virion. We reasoned that by pairing a laboratory adapted HA with a second HA protein, derived from a circulating pathogenic IAV strain, we could ensure robust growth of the resultant IAV regardless of the growth characteristics of the second HA and thereby reduce the selective pressure on this HA to mutate.

To accomplish this goal we needed to establish a genomic organization that would encode two functional HA proteins. There have been reports of successful exogenous expression of foreign reporter proteins from the polymerase segments as well as IAV segments 8 and 6 (reviewed in (18, 19)). All of the previously published reports, however, either generated viral-reporter fusion proteins or left residual amino acids that would inactivate a second HA protein. Since all previously published strategies were unsuitable for our purposes, we first needed to develop new methods to insert proteins into IAV that would not result in modifications to these proteins. For a rapid readout of virus rescue, we began by attempting to insert fluorescent proteins.

Figure 1E:
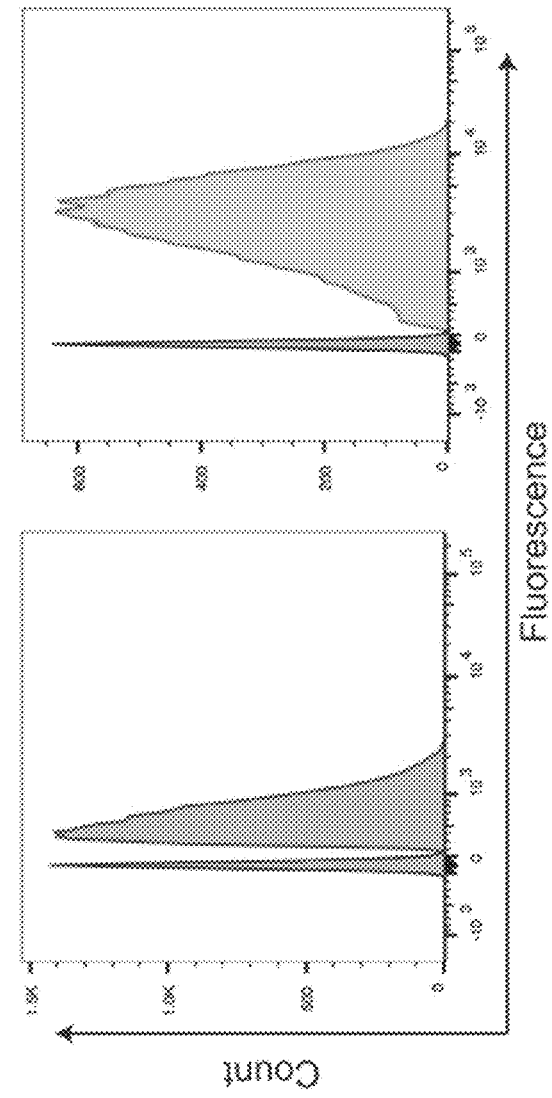
(FIG. 1E) Flow cytometry of mRuby2-HA and mNeon-HA infected (red or green) and uninfected cells (grey) represented as a histogram (FIG. 1F) A quantification of the brightness of mRuby2-HA and mNeon-HA infected cells.
Figure 1F:
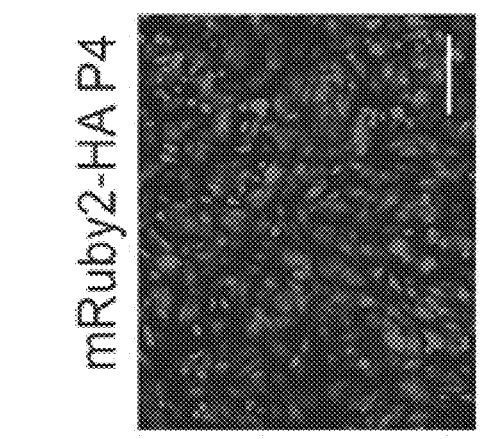
FIG. 1 shows encoding a red fluorescent reporter protein in segment 4 without leaving residual tags on the viral HA protein.
(FIG. 1A) Diagram of the genomic segment 4 HA based fluorescent reporter virus.
(FIG. 1B) Endpoint titer of the mRuby2-HA virus compared to wild-type PR8 after 72 hr incubation in eggs.
(FIG. 1C) Multi-cycle growth kinetics of the mRuby2-HA virus on MDCK cells compared to WT.
(FIG. 1G) Viral segment 4 RT-PCR from wild-type PR8 and the passage 0 and 4 of mRuby2-HA. The red arrowhead indicates the presence of the reporter gene; the black arrowhead indicates no reporter.
(FIG. 1H) Fluorescence microscopy of cells 24 hours post-infection at an MOI of 1 with the passage 4 mRuby2-HA virus. For all panels *p≤0.05, **p≤0.001, and scale bars=100 µm.
Figure 1G:
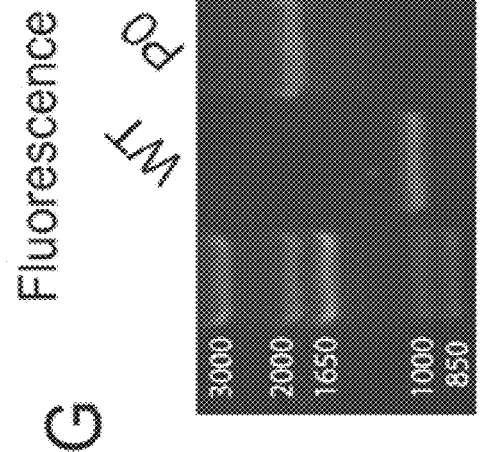
Figure 1H:
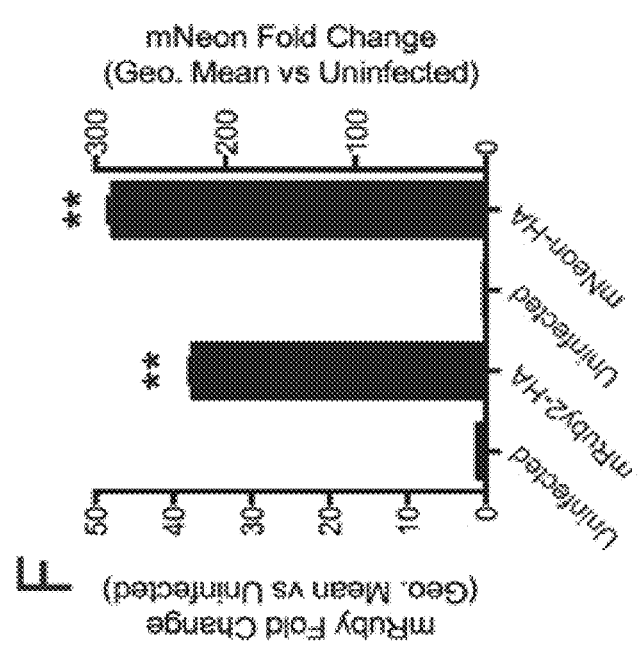
Figures 2A, 2B:
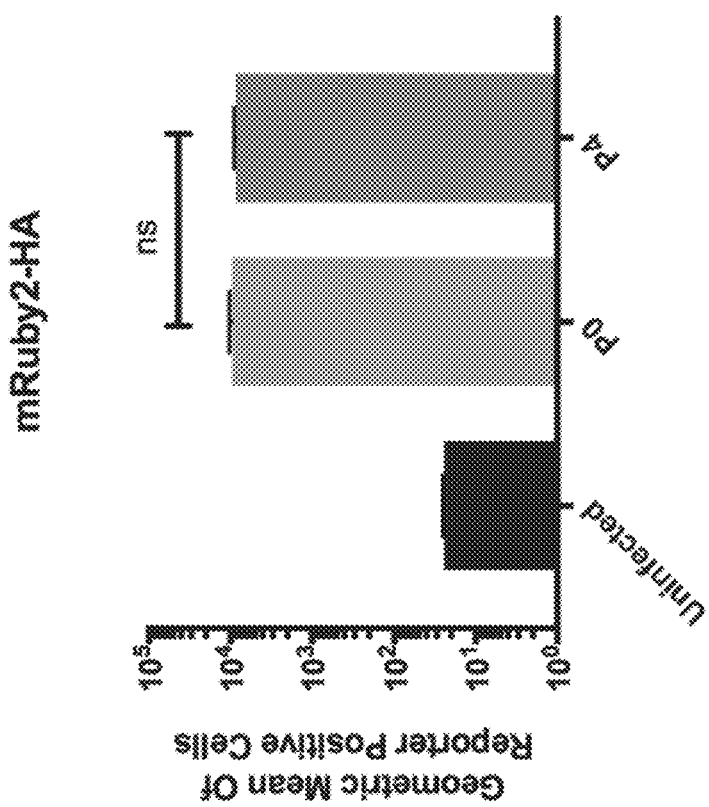
(FIG. 2A) Quantification of the brightness of passage 0 and passage 4 mRuby2-HA infected cells via flow cytometry.
(FIG. 2B) A table comparing the number of reporter positive plaques out of total plaques between passage 0 and passage 4 of the mRuby2-HA virus. Identified plaques were confirmed via staining for flu proteins as described in Methods & Materials.
Figure 2C:
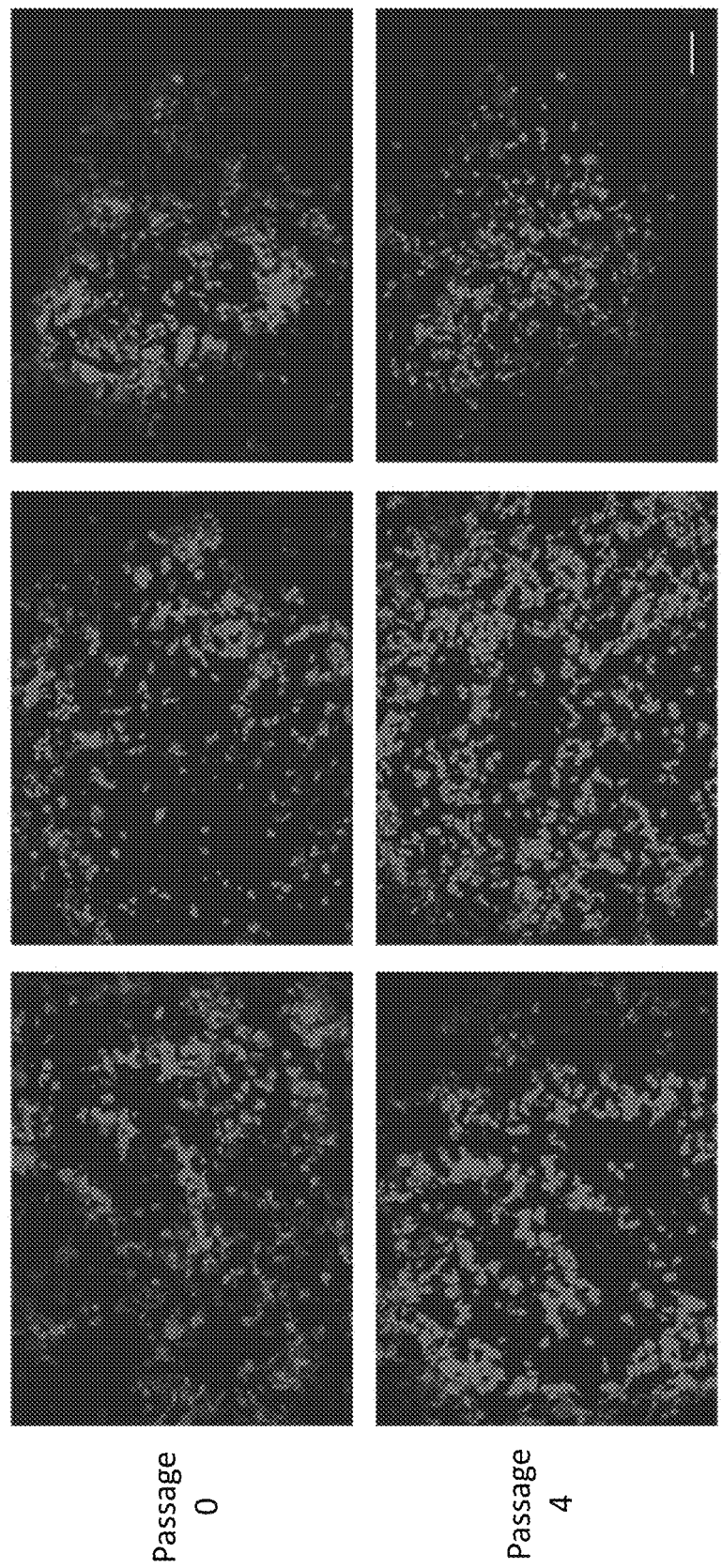
(FIG. 2C) Representative images of the plaques that were counted, demonstrating similar brightness and morphology between passages.

Since the IAV HA encodes an N-terminal signal peptide which mediates appropriate sub-cellular localization and then is removed to generate the mature HA (20), we reasoned that encoding a fluorescent mRuby2 gene before the protein would not leave any additional amino acids on HA after signal peptide removal. To ensure the signal peptide was recognized during translation, we engineered a porcine teschovirus 2A (PTV1-2A) motif to separate the fluorescent reporter and HA (FIG. 1A). Thus, the mRuby2 sequence should be released from the nacent polypeptide as the ribosome translates the PTV1-2A sequence and remain in the cytoplasm, while the HA signal peptide should be recognized and then removed during normal HA trafficking to the plasma membrane. We were able to rescue this virus in the H1N1 A/Puerto Rico/8/1934 (PR8) background and show that the resultant virus grew to high titers (FIG. 1B). In multi-cycle growth, the kinetics were similar to the parental strain (FIG. 1C). The HA segment is normally highly expressed in infected cells, and we were readily able to detect infected cells via microscopy and flow cytometry assays, with brightness of the reporter related to the multiplicity of infection (MOI) (FIGS. 1D,E). While red fluorescent proteins are useful to minimize signal overlap with green autofluoresence in tissue sections (21, 22), they display lower brightness relative to green or yellow fluorescent proteins (23, 24). We therefore also rescued a virus expressing the exceptionally bright mNeonGreen protein (25) in the HA segment and performed flow cytometry (FIGS. 1E,F). Quantification of the brightness of infected cells for both viruses was performed at 24 hr post infection, with an observed ~35-fold increase for the mRuby2 virus and an ~300-fold increase for the mNeon virus (FIG. 1F). Thus, we were able to encode foreign proteins in segment 4 of IAV with minimal effects on virus growth and no residual amino acids left on the viral HA protein. Finally, we assessed the stability of our mRuby2-HA virus over 4 serial passages in eggs. We observed no change in segment length or loss of fluorescence (FIGS. 1G,H), indicating that the virus tolerates these manipulations. We also verified that the brightness of the virus did not decrease during the passaging, as well as performed plaque assays to ensure no minor population of the stock had lost fluorescence (FIG. 2A-C).

While our segment 4 design was successful in producing wild-type HA protein, there were residual C-terminal amino acids left from the PTV1-2A motif on the mRuby2 protein. Thus, we would ultimately not accomplish our goals by simply incorporating two HA proteins in segment 4. However, previous work has shown that foreign proteins can be expressed on the C-terminus of the neuraminidase (NA) encoded in segment 6. Importantly, in those reports NA was forced to tolerate residual amino acids left on the C-terminus after 2A mediated protein separation (26, 27). To generate an untagged NA protein as a second, complementary approach to HA expression, we aimed to take advantage of cellular peptidases to remove tags left on the proteins at a PTV1-2A cleavage site. Previous work on recombinant protein expression has shown that after introduction of the furin cleavage site "RKRR", recognition by furin protease and subsequent cleavage by carboxypeptidases completely eliminates the residual motif (28). We adapted this approach and encoded mNeon after the NA protein, separating the two proteins by a furin cleavage site and a PTV1-2A site (FIG. 3A).

Figures 3F, 3G, 3H:
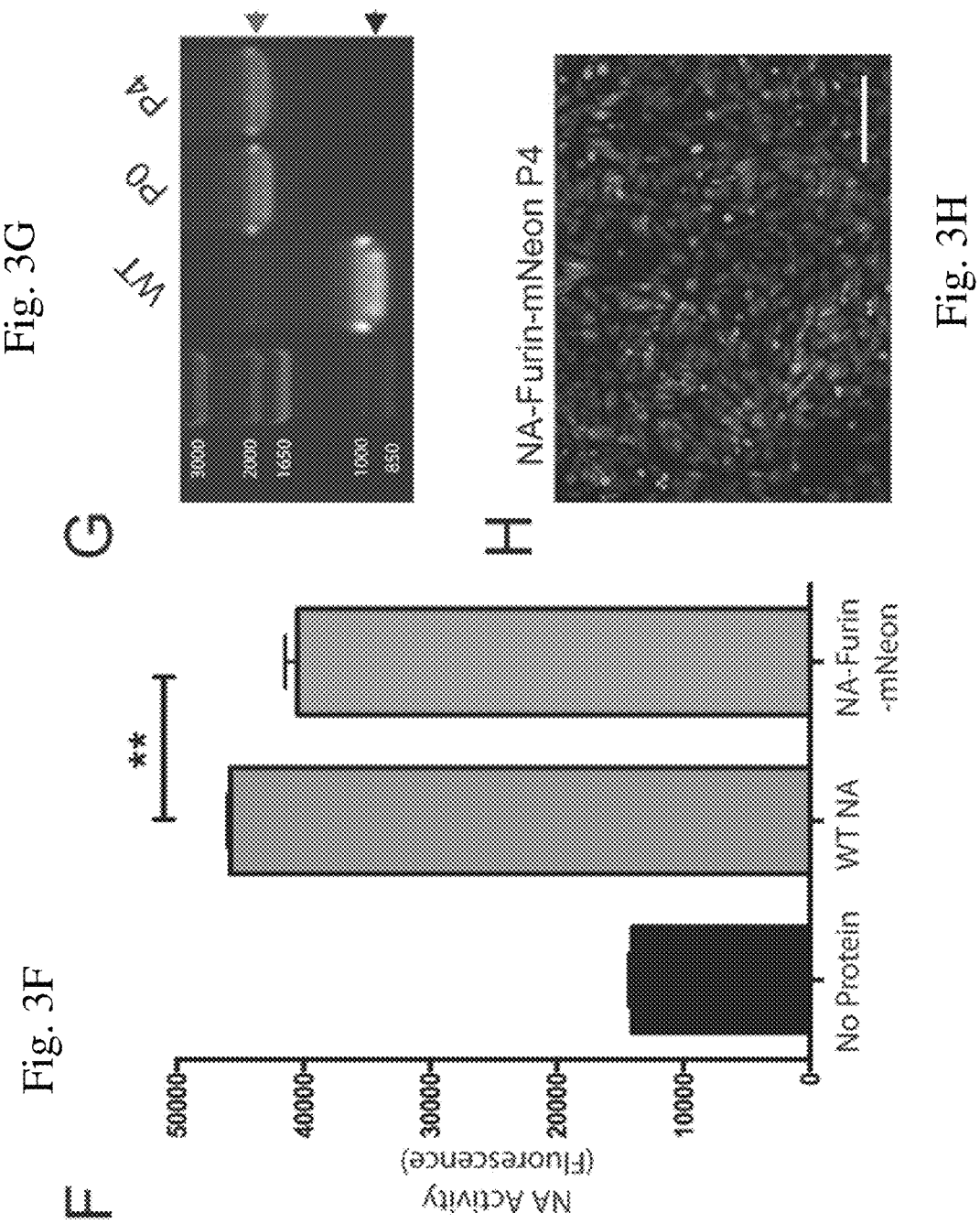
(FIG. 3F) A comparison of neuraminidase activity of purified flag-tagged neuraminidase from WT PR8 and the NA-Furin-mNeon virus.
(FIG. 3G) Viral segment RT-PCR from wild-type PR8 and the passage 0 and 4 of the NA-Furin-mNeon virus (SEQ ID NO: 44). The green arrowhead indicates the presence of the reporter gene; the black arrowhead indicates no reporter.
(FIG. 3H) Fluorescence microscopy of cells 24 hours post infection at an MOI of 1 with the passage four NA-Furin-mNeon virus. For all panels *p≤0.05, **p≤0.001, and scale bars=100 µm.
Figure 4:
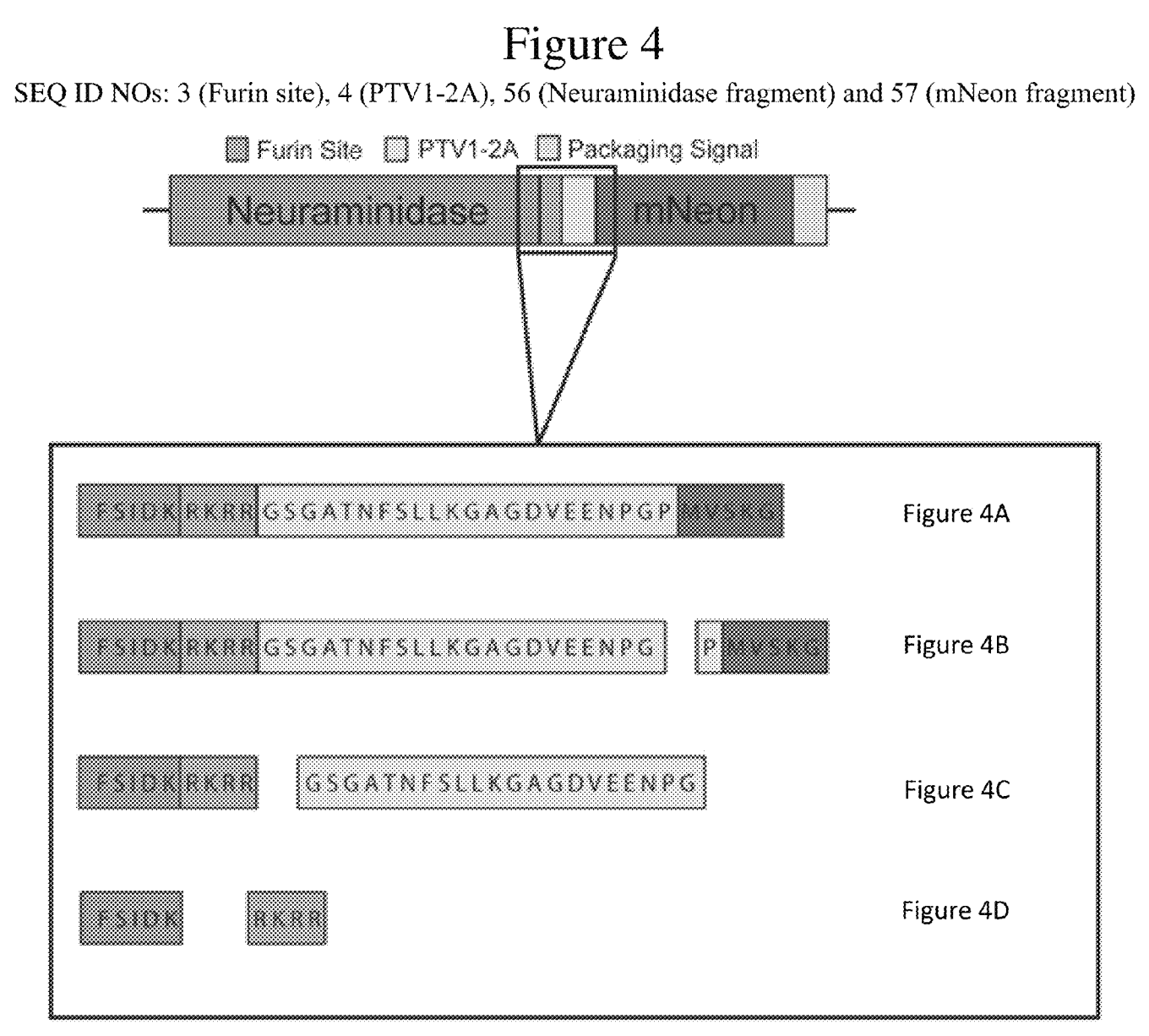
Figures 5A, 5B:
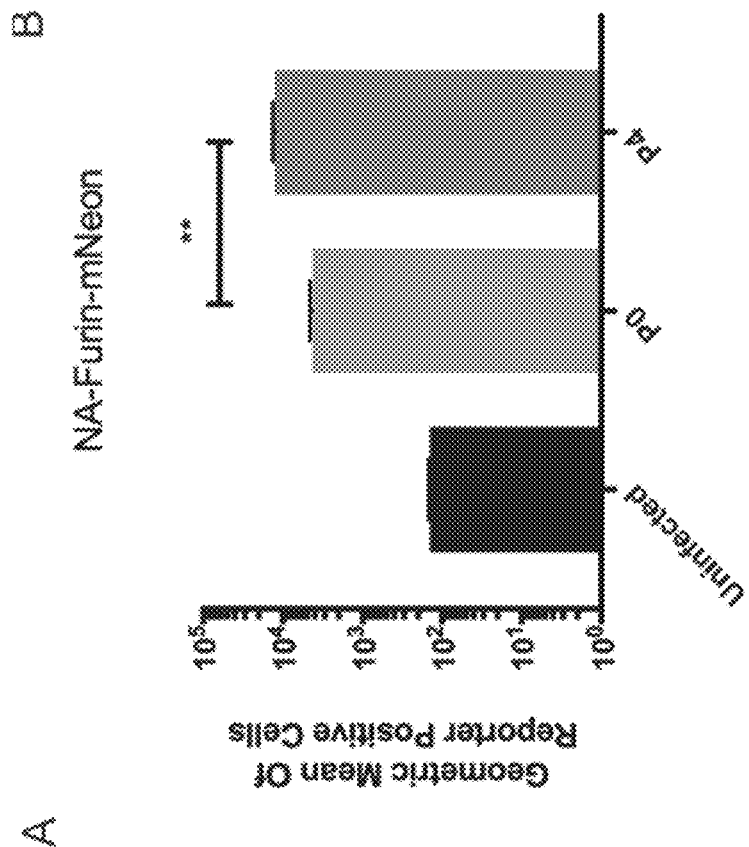
(FIG. 5A) Quantification of the brightness of passage 0 and passage 4 NA-Furin-mNeon infected cells via flow cytometry.
(FIG. 5B) A table comparing the number of reporter positive plaques out of total plaques between passage 0 and passage 4 of the NA-Furin-mNeon virus. Identified plaques were confirmed via staining for flu proteins as described in Methods & Materials.
Figure 5C:
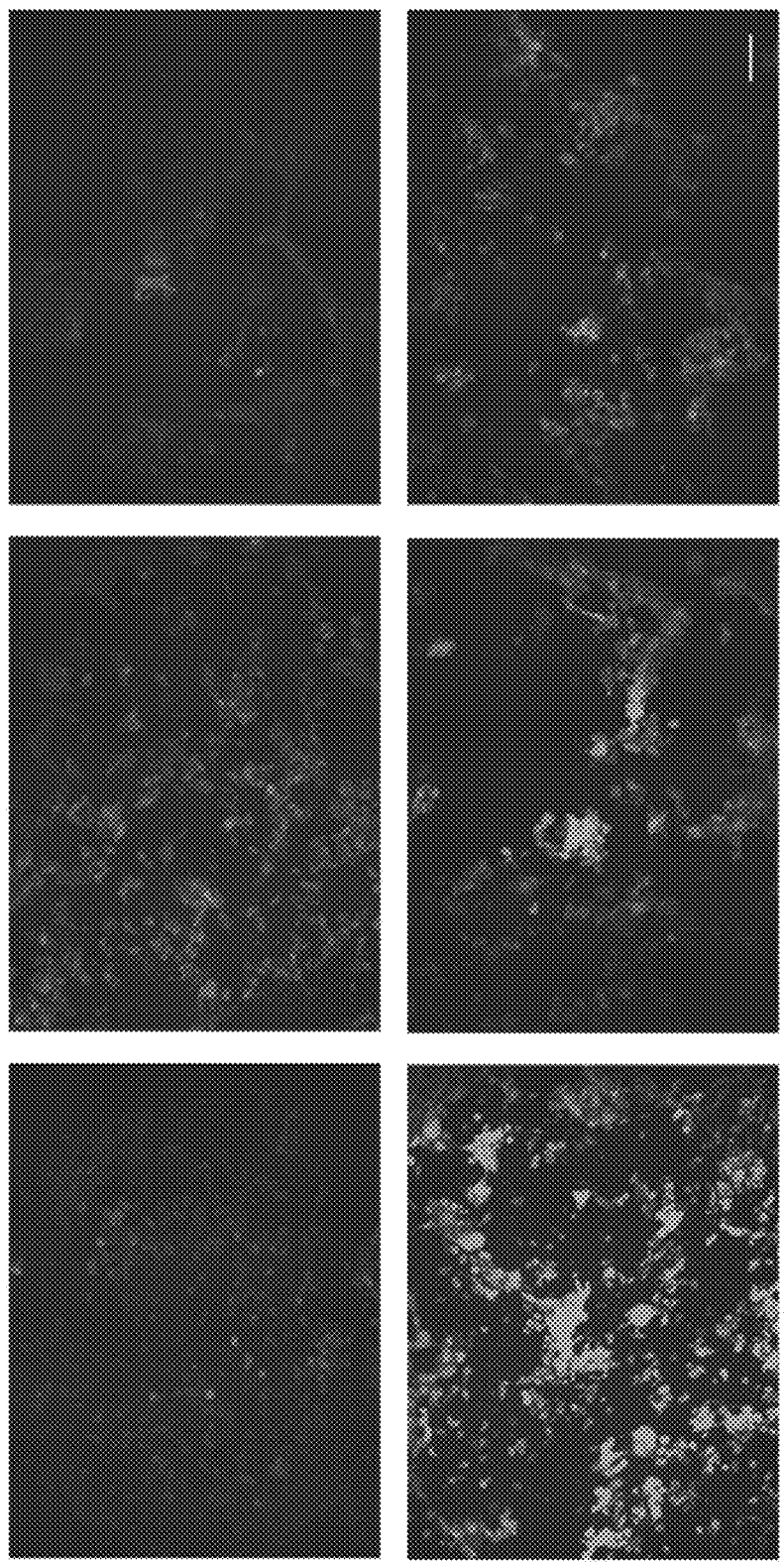
(FIG. 5C) Representative images of the plaques that were counted, demonstrating similar brightness and morphology between passages.

Rescue and characterization of this virus showed that the virus grew to high titers and replicated with similar kinetics to the parental PR8 virus (FIGS. 3B,C). Infected cells were readily detected and the brightness was quantified via flow cytometry (FIGS. 3D,E). To assess the activity of NA-FurinmNeon vs WT NA, we rescued viruses with FLAG-tagged versions of both neuraminidases (29), then purified NA and performed a sialidase assay (FIG. 3F). The slight reduction in activity likely indicates not all of the NA is fully processed by the furin protease as intended, potentially leaving some amino acids on the N-terminus (diagrammed in FIG. 4). Finally, we assessed the stability of our NA-furin-mNeon virus over 4 serial passages. We again observed no loss of the reporter gene or decrease in brightness (FIGS. 3G-H, FIGS. 5A-C). Thus, we have developed two ways to express foreign proteins, one in segment 4 and one in segment 6, which leave little to no residual modification on the viral proteins and are well tolerated by the virus.

Figure 6A:
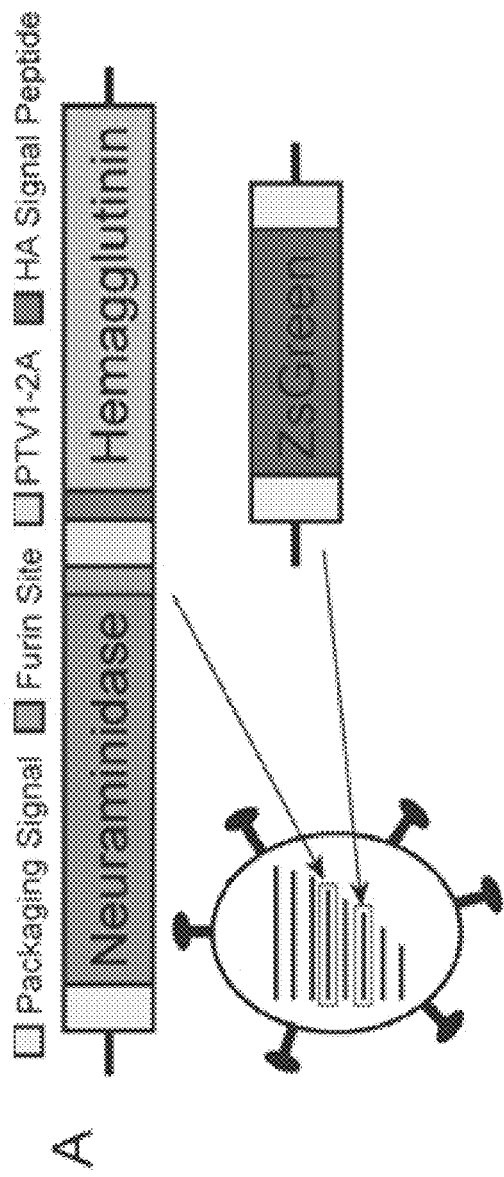
(FIG. 6A) Diagram of the virus expressing both HA and NA glycoproteins in the genomic segment 4 and ZsGreen in the genomic segment 6.
Figure 6B:
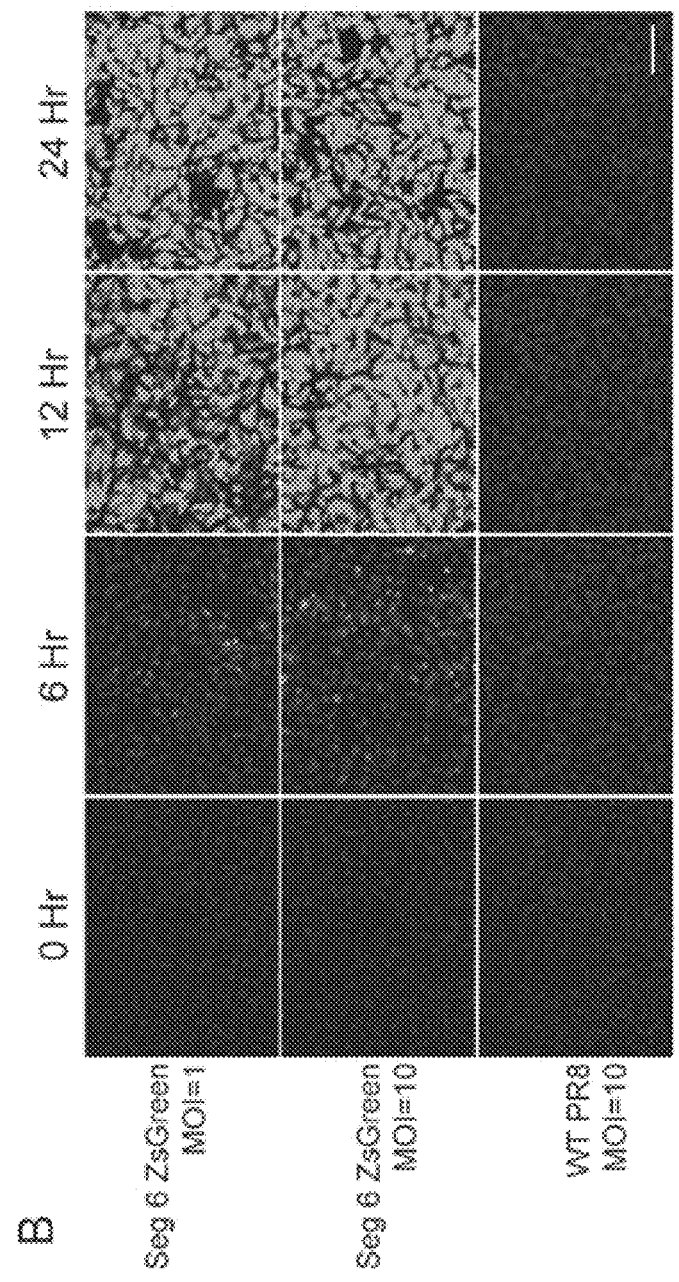
(FIG. 6B) Fluorescent microscopy time course of a single cycle infection on MDCK cells comparing green fluorescence between wild-type and segment 4 NA/HA, segment 6 ZsGreen viruses.

We theorized that by combining these strategies we could express both the HA and the NA glycoprotein from a single viral segment. We therefore encoded the NA protein, followed by a furin cleavage site, then PTV1-2A, and finally the HA protein, in segment 4 (FIG. 6A). Since seven segment influenza viruses are known to grow poorly (30), we encoded the fluorescent protein ZsGreen in segment 6, where NA is normally encoded, as a "place holder" (FIG. 6A). We successfully rescued this virus and observed that the virus expressed the reporter protein and grew to high titers (FIGS. 6B,C) despite the reorganization of the glycoproteins. We also observed extremely high expression of the ZsGreen reporter protein (FIGS. 6D,E), likely due to the addition of an artificial consensus Kozak signal in front of the reporter protein.

Figure 6J:
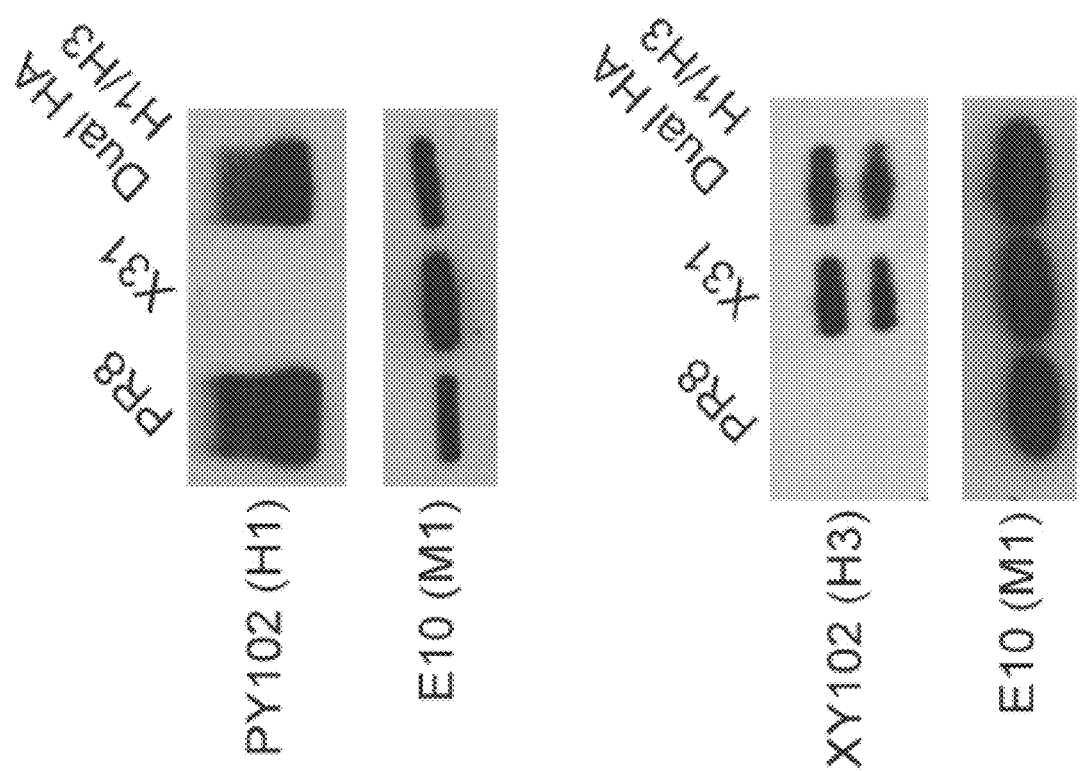
(FIG. 6J) Western blot of concentrated virus for the subtype 1 and 3 hemagglutinins.
Figure 7:
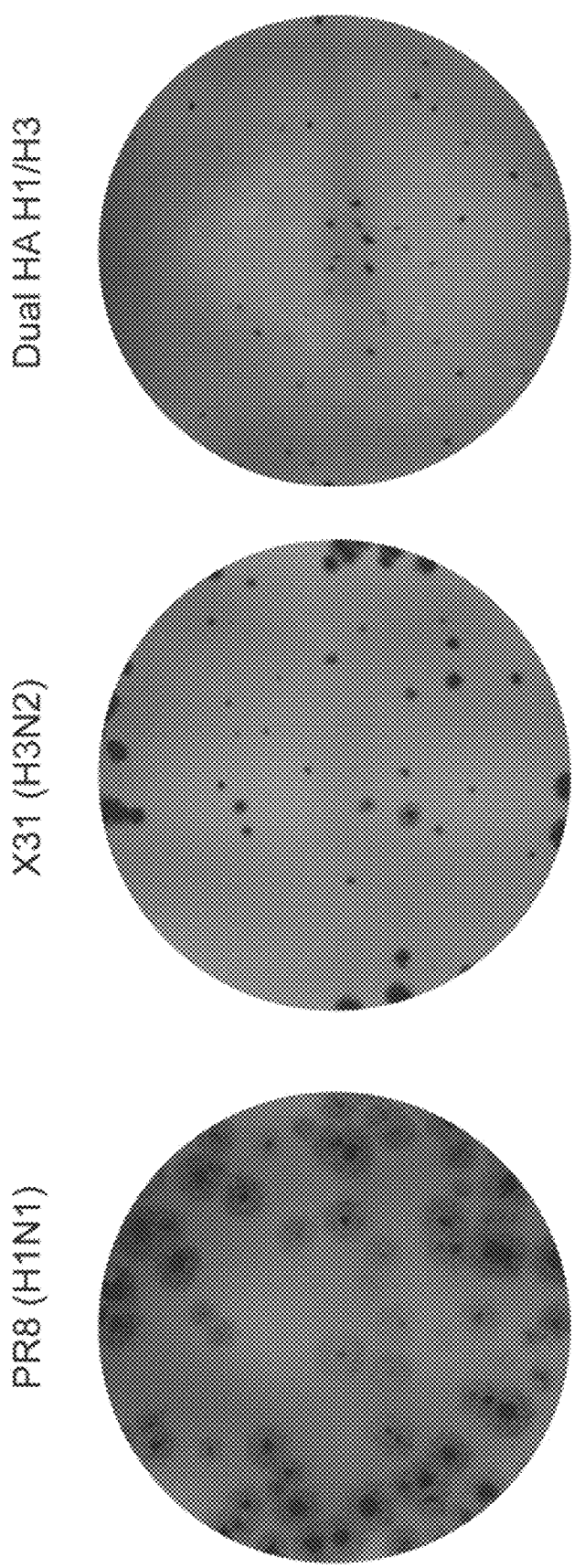
FIG. 7 shows plaque morphology of the parental PR8 (H1N1), X31 (H3N2) viruses as compared to the Dual HA H1/H3 virus in a plaque assay on MDCK cells.

Since expressing HA and NA in a single segment was well-tolerated by the virus, we returned to our original goal of a dual HA IAV virus and designed a virus to express both a subtype 1 and a subtype 3 HA simultaneously (FIG. 6F). We encoded the original PR8 H1 protein in segment 4 (along with the NA protein), and encoded an additional H3 protein (from A/Hong Kong/1968) in segment 6 (where NA is normally located). We chose H1 and H3 HAs because these two IAV subtypes are currently circulating in humans, and we wanted to assay the ability of this technology to allow the incorporation of both subtype H1 and H3 HA proteins on the same virion. We were able to rescue this virus and found that it grew to high titers, with no statistical difference in endpoint titer relative to the parental PR8 strain, but with a delay in the kinetics of viral growth (FIG. 6G, H). We were also able to detect viral plaques with antibodies specific for either subtype 1 or subtype 3 HAs in after infection with the H1/H3 dual HA virus (FIG. 6I). Plaque size of the dual HA virus was reduced compaired to the parental PR8 strain, but similar to the A/Hong Kong/1968-PR8 reassortant strain X31 (FIG. 7). We also determined the levels of the HA proteins in the dual HA background relative to the H1 parent PR8 or the H3 parent X31 via Western blot. Using purified virions we observed that the H1/H3 virions packaged similar levels of both the H1 and H3 glycoprotein to the single HA parent strains (FIG. 6J).

Figure 6K:
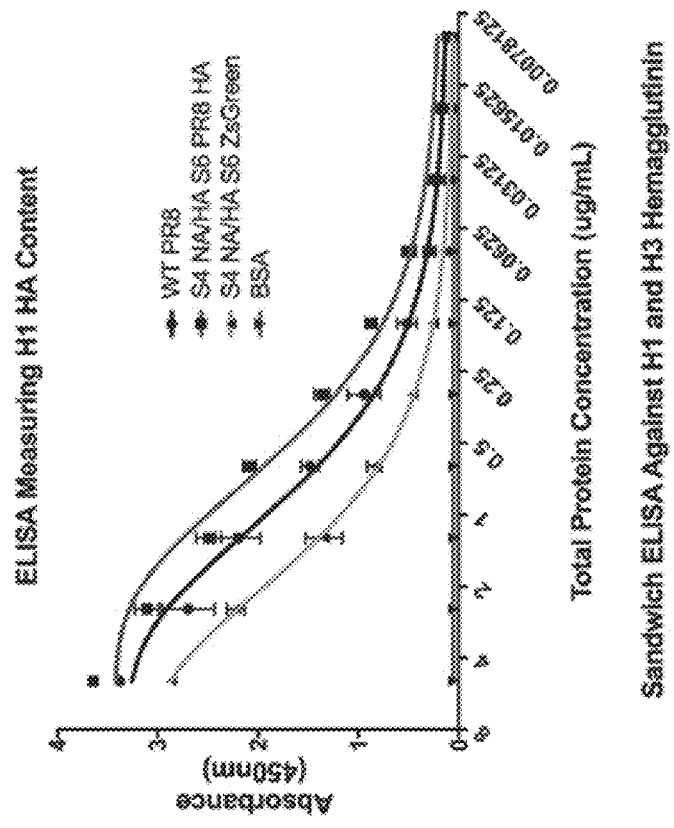
(FIG. 6K) ELISA measuring subtype 1 HA content utilizing a virus expressing two subtype 1 HAs from segment 4 and segment 6.
Figure 6L:
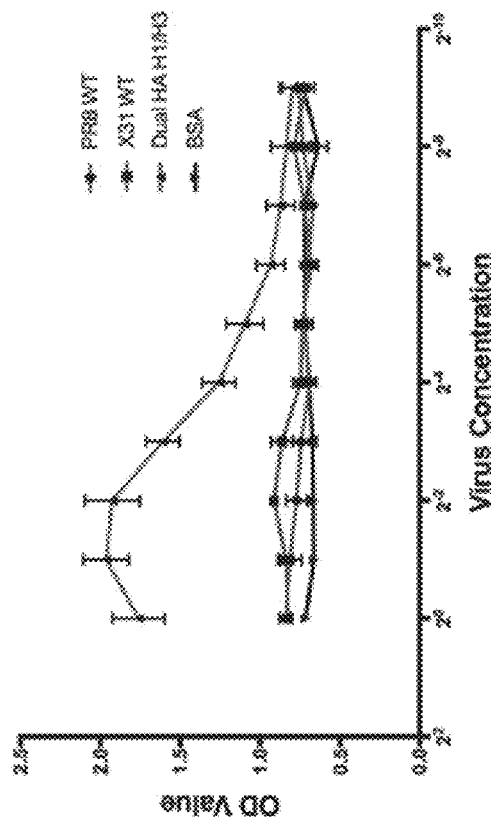
(FIG. 6L) Sandwich ELISA of PR8, X31, and H1/H3 virus measuring content of H1 and H3 subtype HAs on the same virion.
Figure 8:
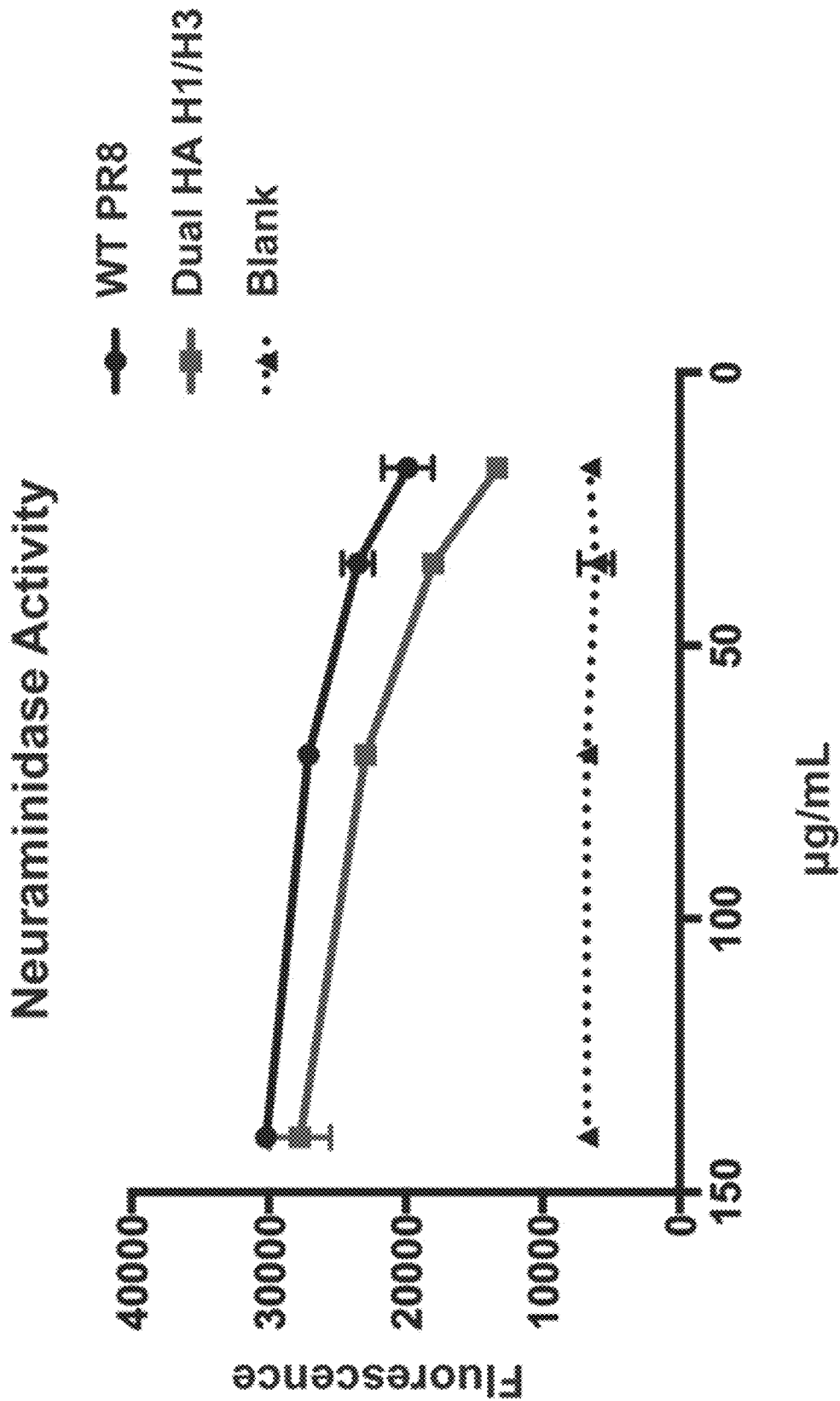
FIG. 8 shows bivalent viruses have lower neuraminidase activity relative to WT PR8. Both WT PR8 and the Dual HA H1/H3 virus samples were concentrated and normalized to total protein. A sialidase activity assay was then performed, following the standard procedures of the Sigma-Aldrich Neuraminidase Activity Kit (MAK121), to evaluate NA content of each sample.

To quantify the total amount of HA on the surface of the virion, we rescued a double PR8 H1/H1 dual HA virus and performed an ELISA assay on the purified virions with an H1 specific antibody. We observed that the double HA virus packaged more HA protein than the single HA parent, as expected from our Western blot analysis (FIG. 6K). NA activity levels were slightly reduced relative to parental PR8, likely indicating a slight reduction in the amount of the NA protein packaged (FIG. 8). We also performed a sandwich ELISA with monoclonal antibodies specific for the PR8 or HK68 HA to demonstrate that both HA proteins were being packaged onto the same virion (FIG. 6L). In order to assay the stability of the second HA protein, we injected 20 embryonated chicken eggs with the dual H1/H3 virus. After 72 hours of viral growth, a plaque assay was performed with each of the 20 viral populations. Plaques visible to the eye were stained with an H3 specific monoclonal antibody; we observed that every plaque was positive for the HK68 HA protein (Table 2).

TABLE 2

Dual HA A/Hong Kong/1/68-PR8 virus stably expresses second HA in twenty independent parallel passages. Plaques that stained positive for A/Hong Kong/1/68 HA are shown out of the total plaques counted for each passage.

| Dual HA H1/H3 | Counted Plaques | H3 Positive Plaques | Cumulative Positive Plaques |
|---|---|---|---|
| Passage A | 6 | 6 | 6/6 |
| Passage B | 7 | 7 | 13/13 |
| Passage C | 7 | 7 | 20/20 |
| Passage D | 4 | 4 | 24/24 |
| Passage E | 5 | 5 | 29/29 |
| Passage F | 5 | 5 | 34/34 |
| Passage G | 3 | 3 | 37/37 |
| Passage H | 5 | 5 | 42/42 |
| Passage I | 3 | 3 | 45/45 |
| Passage J | 2 | 2 | 47/47 |
| Passage K | 3 | 3 | 50/50 |
| Passage L | 3 | 3 | 53/53 |
| Passage M | 5 | 5 | 58/58 |
| Passage N | 5 | 5 | 63/63 |
| Passage O | 5 | 5 | 68/68 |
| Passage P | 5 | 5 | 73/73 |
| Passage Q | 4 | 4 | 77/77 |
| Passage R | 4 | 4 | 81/81 |
| Passage S | 5 | 5 | 86/86 |
| Passage T | 9 | 9 | 95/95 |

Figure 6M:
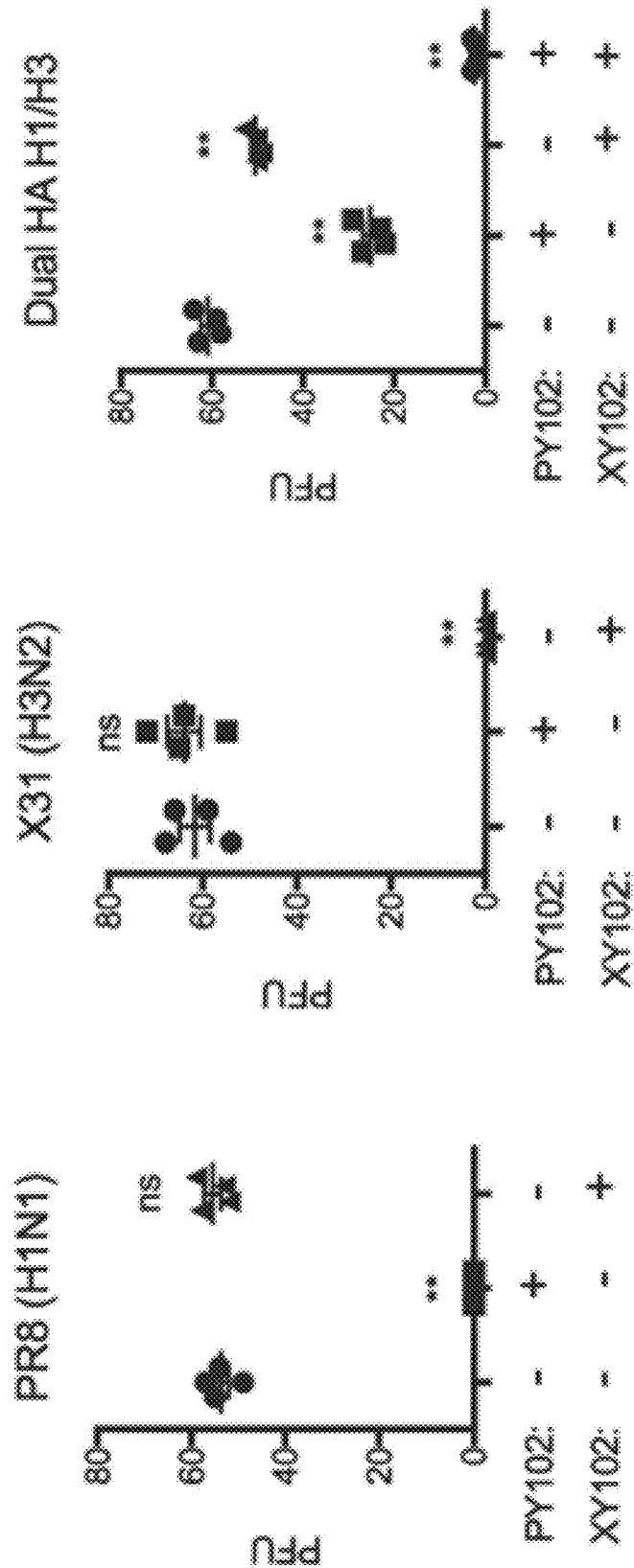
(FIG. 6M) Plaque reduction assays with subtype specific H1 (0.1 µg/mL) and H3 monoclonal antibodies (1 µg/mL).
Figure 6N:
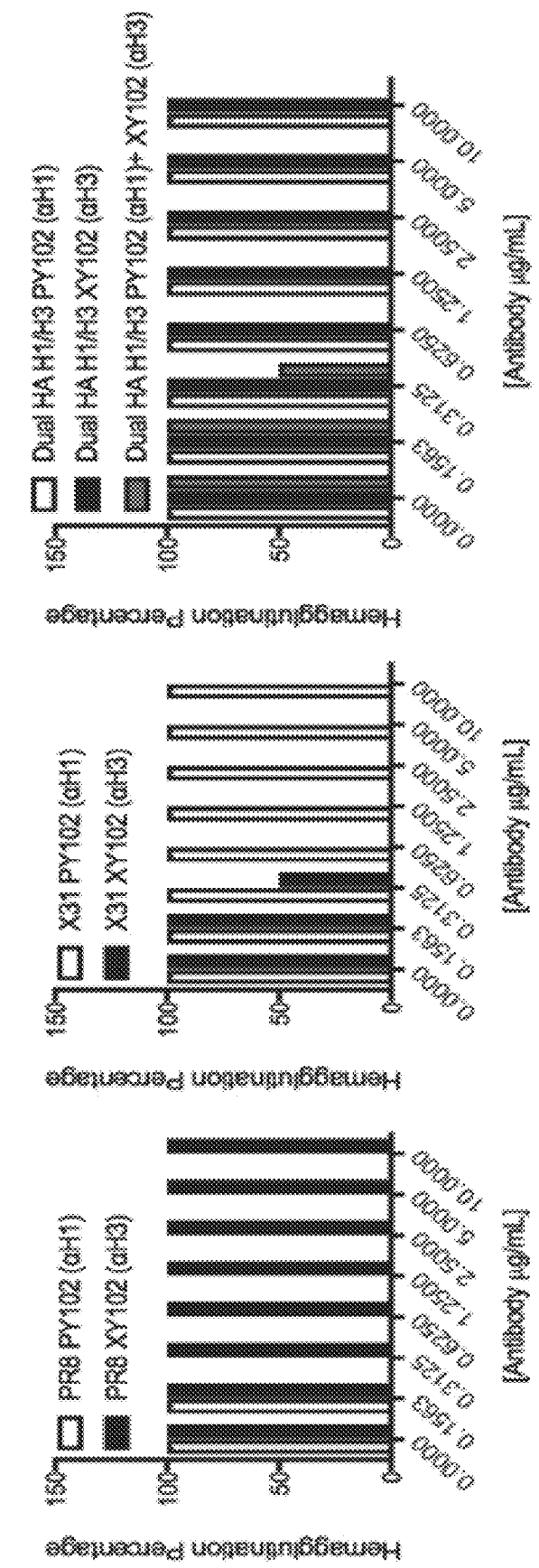
(FIG. 6N) Hemagglutination Inhibition assays (HAIs) utilizing antibodies against both subtype 1 and 3 hemagglutinins. For all panels *p≤0.05, **p≤0.001, and scale bars=100 µm.
Figures 9A, 9B, 9C, 9D:
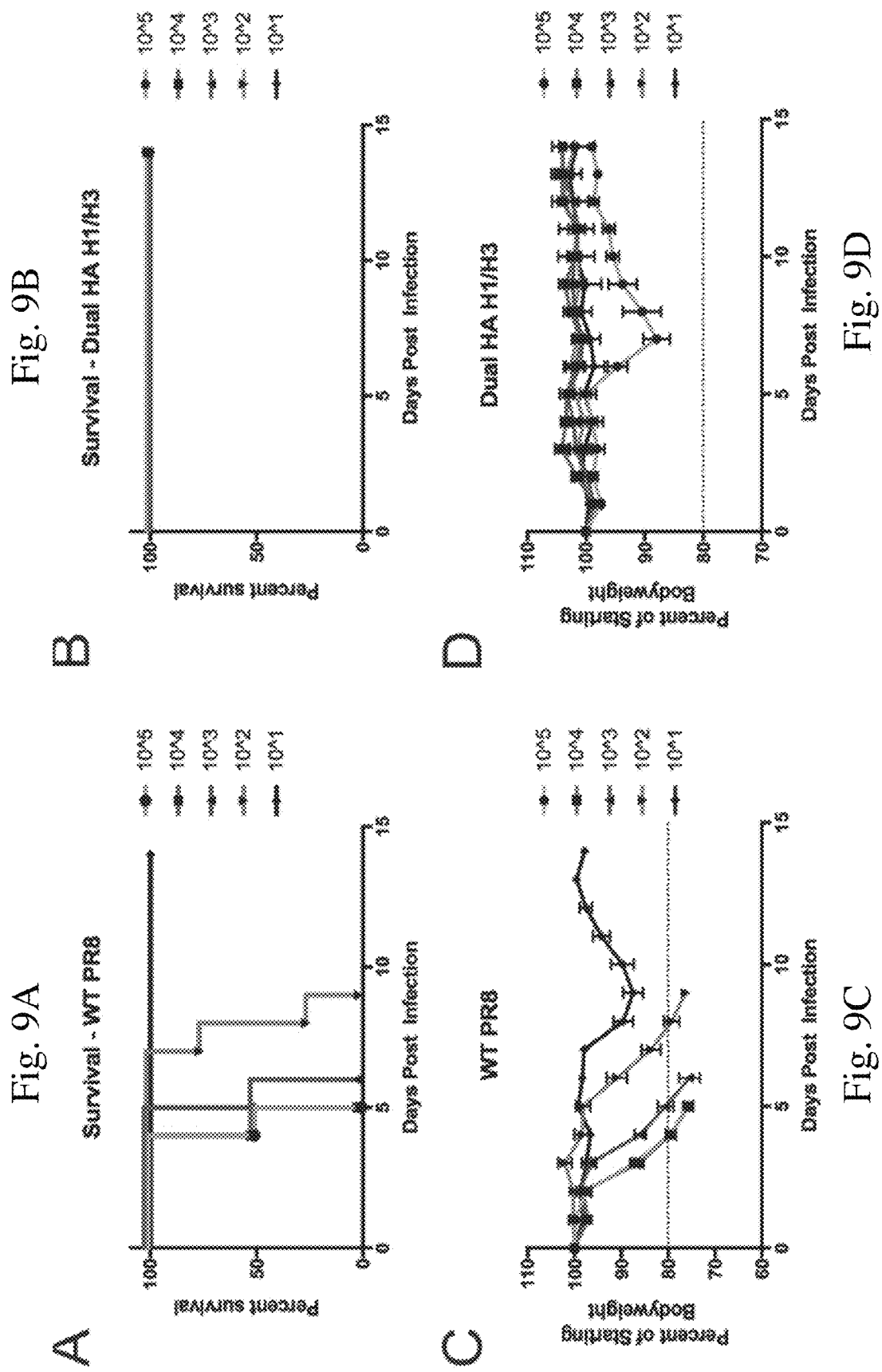
(FIGS. 9A-B) Weight-loss curves from infections with the indicated doses of wild-type PR8 (FIG. 9A) or the H1/H3 dual HA virus (FIG. 9B).
(FIGS. 9C-D) Survival curves from infections with the indicated doses of wild-type PR8 (FIG. 9C) or the H1/H3 virus (FIG. 9D).

We next tested the functionality of both the H1 and H3 HAs in our dual HA virus. We incubated our dual HA virus with neutralizing monoclonal antibodies specific for either the H1 or H3 HA. We observed that only when we mixed both antibodies together were we able to completely neutralize the dual H1/H3 virus (FIG. 6M, N). We reasoned that the delay in viral replication kinetics due to increased genome size would significantly attenuate the virus. We therefore tested the ability of the H1/H3 virus to act as a live attenuated vaccine without additional mutations. C57BL/6 mice were infected with a range of doses of either the parental PR8 strain or the H1/H3 strain. Despite high morbidity and mortality of the parental PR8 strain, our H1/H3 virus caused no mortality at the tested doses (FIG. 9A-D). Despite the difference in disease, high levels of antibodies were elicited by the H1/H3 virus infection in surviving animals (FIGS. 9E,F). Furthermore, these antibodies were found to neutralize virus at similar levels of those elicited from the parental PR8 infection, as determined by HA inhibition (HAI) and plaque reduction assays (FIGS. 9G-J). Sera used for both HAI and plaque reduction assays were treated with sialic acid receptor-destroying enzyme (RDE) to eliminate non-specific inhibition of viral binding mediated by serum components other than antibodies (31, 32).

Since most IAV vaccines are inactivated, we also wanted to evaluate the dual HA virus in this context. To inactivate the virus for administration, we formalin treated either the H1N1 (PR8), H3N2 (X31), or H1/H3 dual HA virus and intra-muscularly vaccinated mice. After vaccination and a single boost, we found that mice vaccinated with either PR8 or X31 produced high levels of the corresponding HA antibodies (FIGS. 10A,B). Mice vaccinated with PR8 and X31 however, elicited no detectable antibody response to the reciprocal HA, while the dual HA H1/H3 virus vaccination led to equal or higher levels of antibodies to both of the HAs relative to the single HA vaccines.

Figures 10C, 10D:
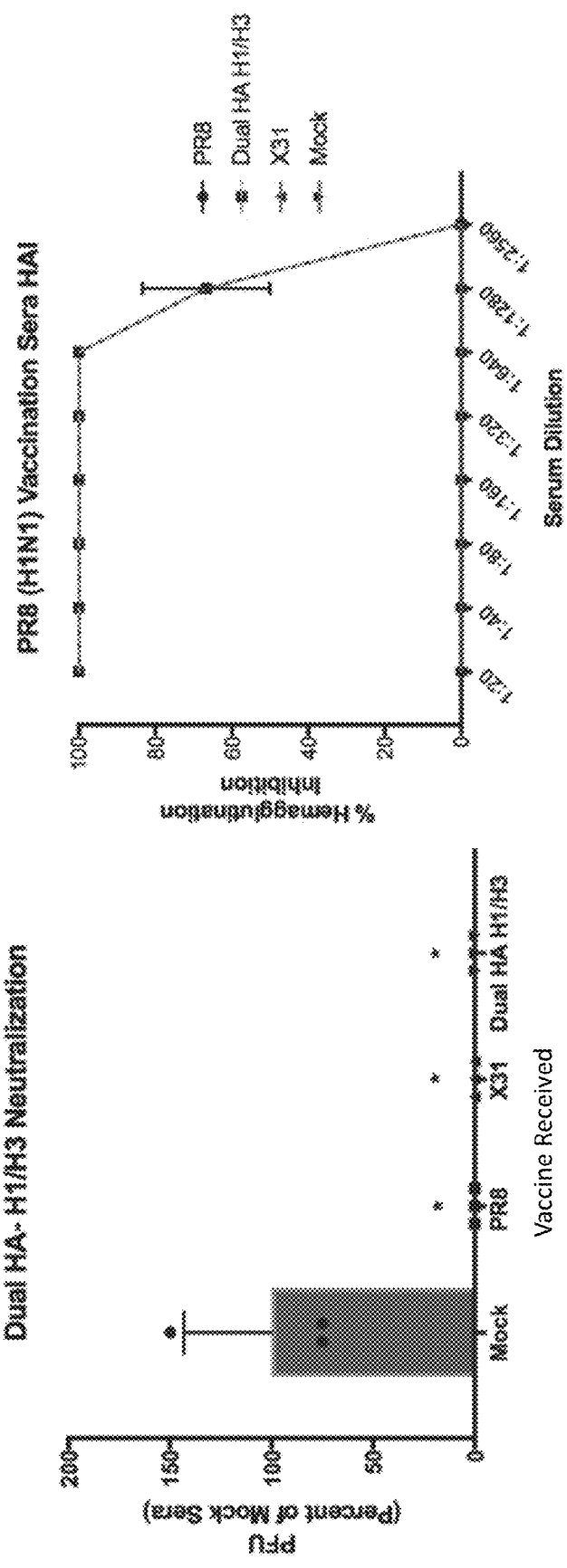
Figure 10I:
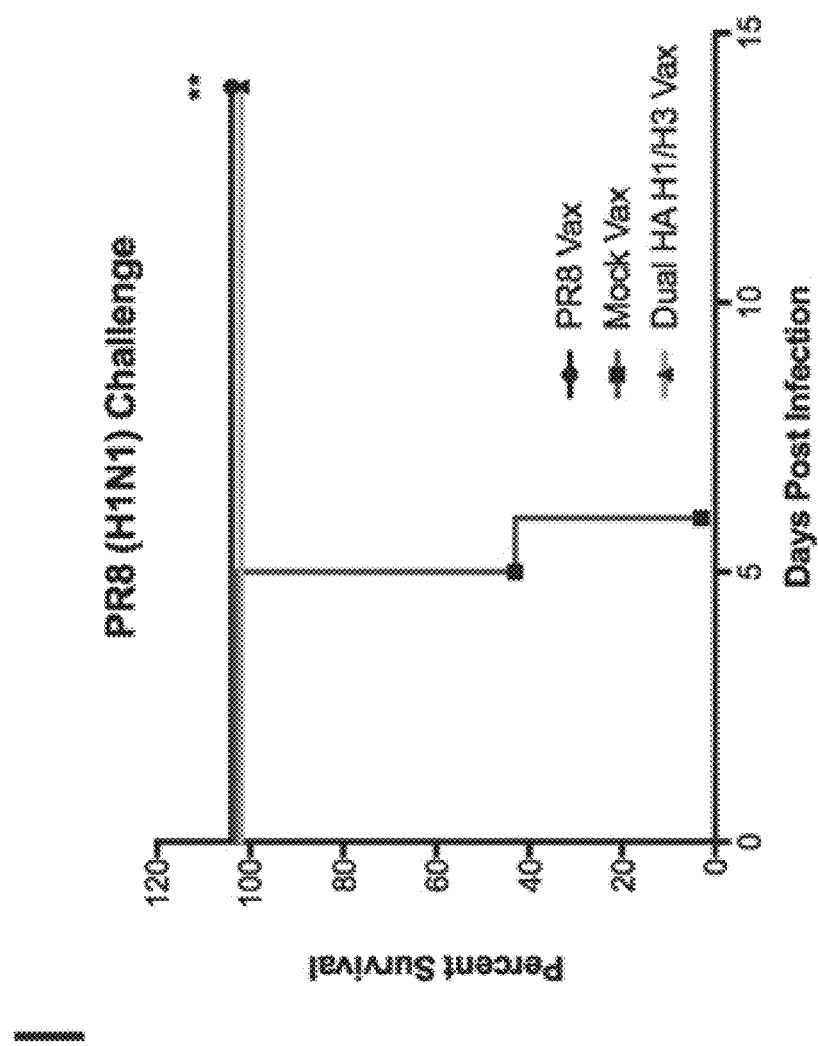

We next wanted to characterize the safety profile of our dual HA virus in more detail. We therefore incubated the H1/H3 virus with polyclonal sera reactive against either PR8 or X31. Both of these sera were able to completely neutralize the dual HA virus, showing that preexisting immunity from vaccination to one of the HA subtypes is sufficient to neutralize a "bivalent" virus (FIG. 10C). HAI and plaque reduction assays with RDE-treated sera raised against the H1/H3 virus revealed functional inhibition of PR8 and X31 receptor binding and virus infection, respectively, with the same efficacy as sera derived from vaccination with either of the single HA parents alone (FIGS. 10D-G, FIG. 11). Finally, we performed challenge experiments to show protection after vaccination in vivo. While vaccination with PR8 was able to protect from PR8 challenge, it was unable to protect from X31 challenge (FIG. 10H, FIGS. 12A & B). Similarly, vaccination with the monovalent X31 virus was able to protect against X31 challenge, but it was not able to protect against PR8 challenge (FIGS. 12C-F). Vaccination with the H1/H3 dual HA virus, however, fully protected mice from challenge with either PR8 or X31 (FIGS. 10H,I and FIGS. 12A & B), indicating that the antibodies generated after H1/H3 virus vaccination are protective.

Figure 13A:
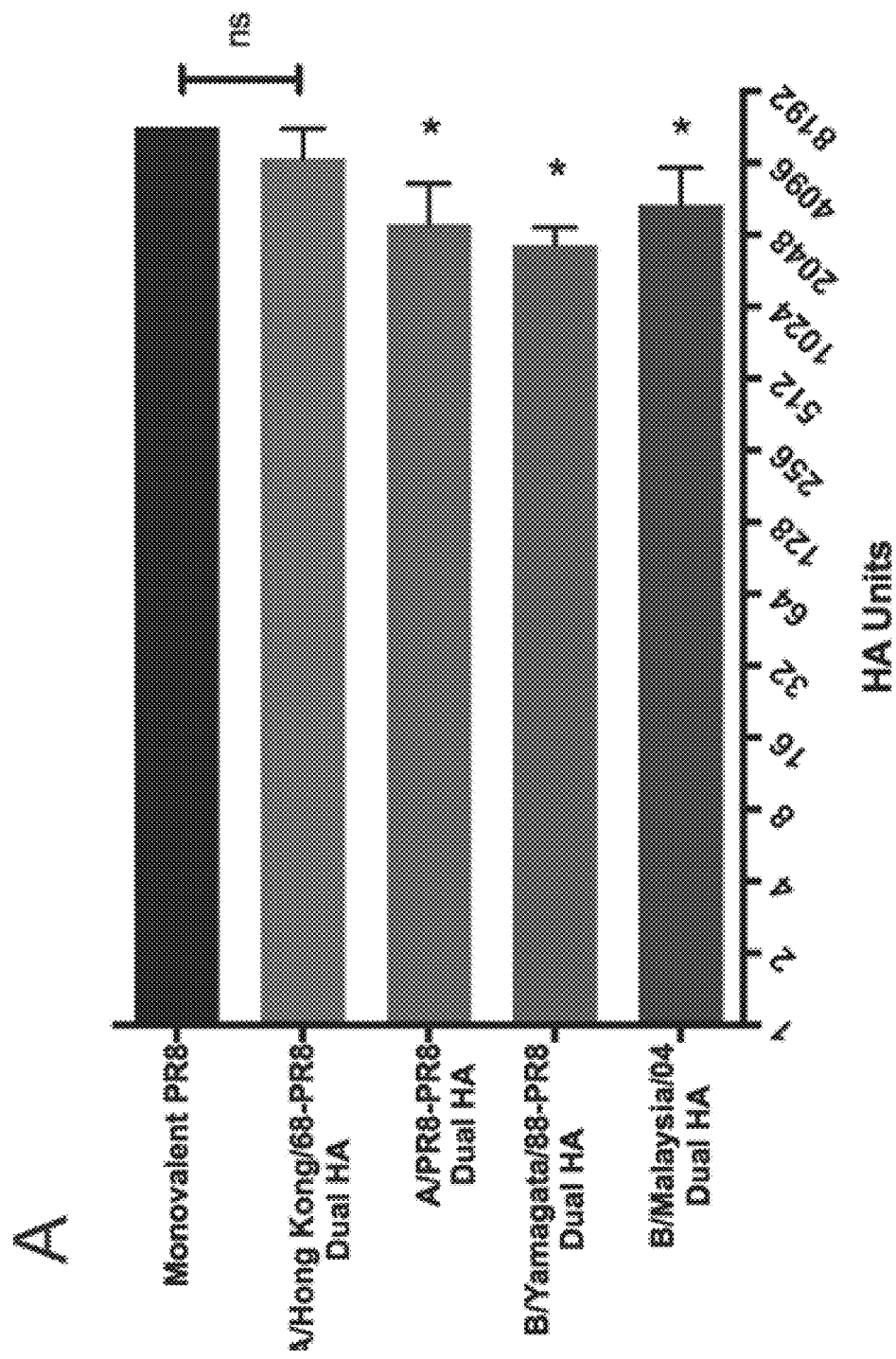
(FIG. 13A) Hemagglutination units of the indicated Dual HA viruses from various IAV and IBV strains (H3: A/Hong Kong/1968, H1: A/Puerto Rico/8/1934, B Yamagata Lineage: B/Yamagata/1988, and B Victoria Lineage: B/Malaysia/2004) relative to the parental PR8 strain.
Figure 13B:
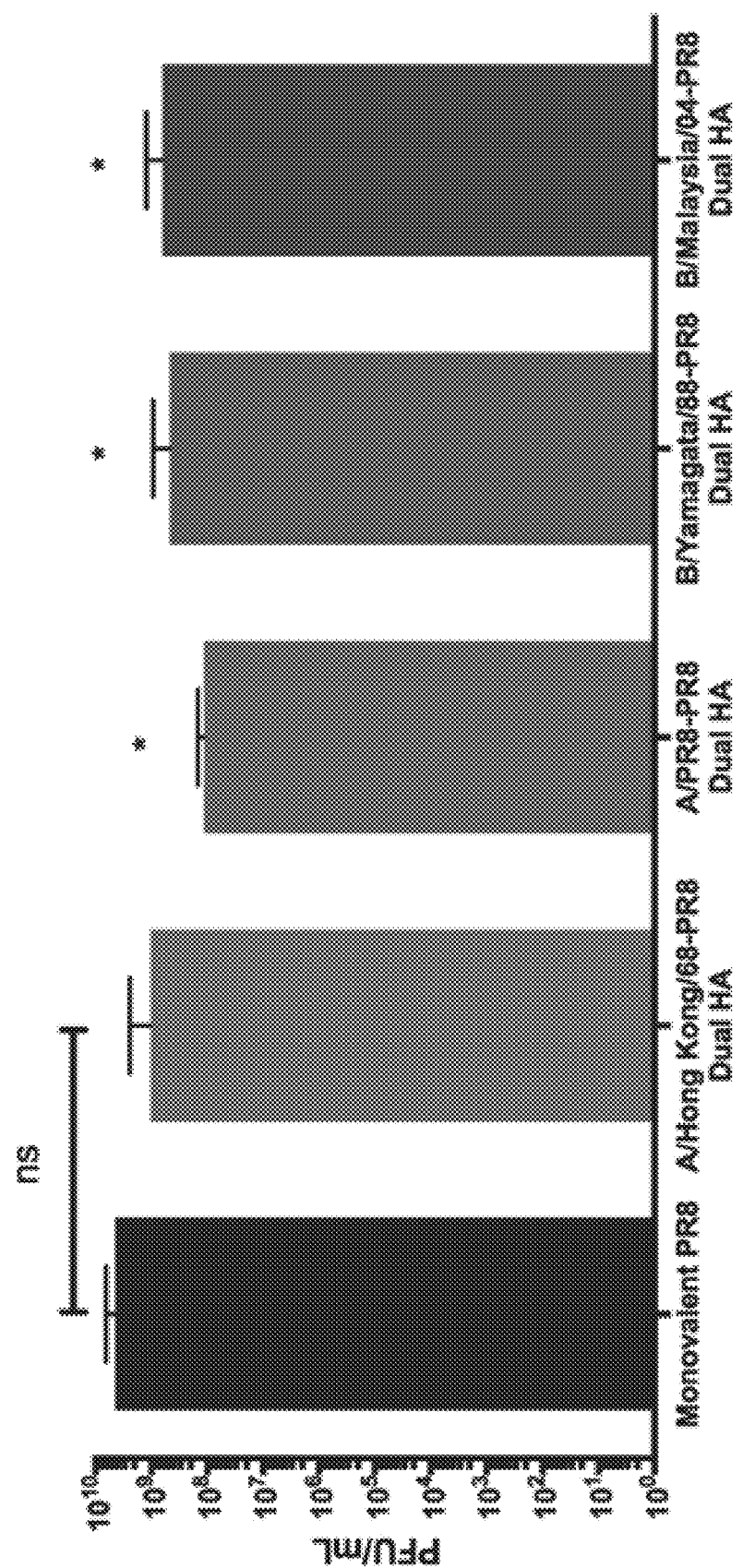
(FIG. 13B) Titer of the viruses from FIG. 13A.

We next evaluated the breadth of HA proteins that could be expressed in the context of a double HA virus. Current quadrivalent IAV vaccines are a mixture of IAVs with a subtype 1 and subtype 3 HA, as well as Influenza B viruses from both the Victoria and Yamagata lineages. We therefore rescued double HA viruses with the PR8 HA and a representative HA from each of these strains. We observed robust growth (without any HA mutations) for all of the recombinant viruses (FIGS. 13A,B), indicating that there was no functional interference between the two HA proteins. To test our approach with current and clinically relevant H3 strain, we rescued a dual HA virus expressing the HA from the A/Victoria/210/2009 strain, which was included in the Fluarix® quadrivalent vaccine produced by GlaxoSmithKline for 2017/2018. As expected, this virus grew to levels similar to that of our other bivalent viruses and, upon sequencing after several rounds of growth in eggs, detected no mutations in the entire ORF of the A/Victoria/210/2009 HA (FIG. 14).

Figure 13C:
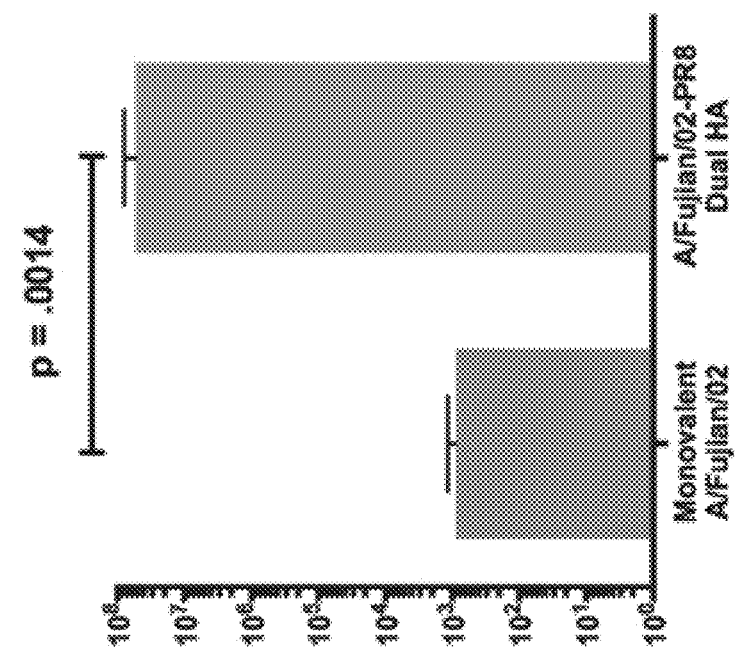
(FIG. 13C) Hemagglutinination units of a dual HA virus expressing the A/Fujian/411/2002 HA relative to the mono-HA A/Fujian/411/2002 WT.
Figure 13D:
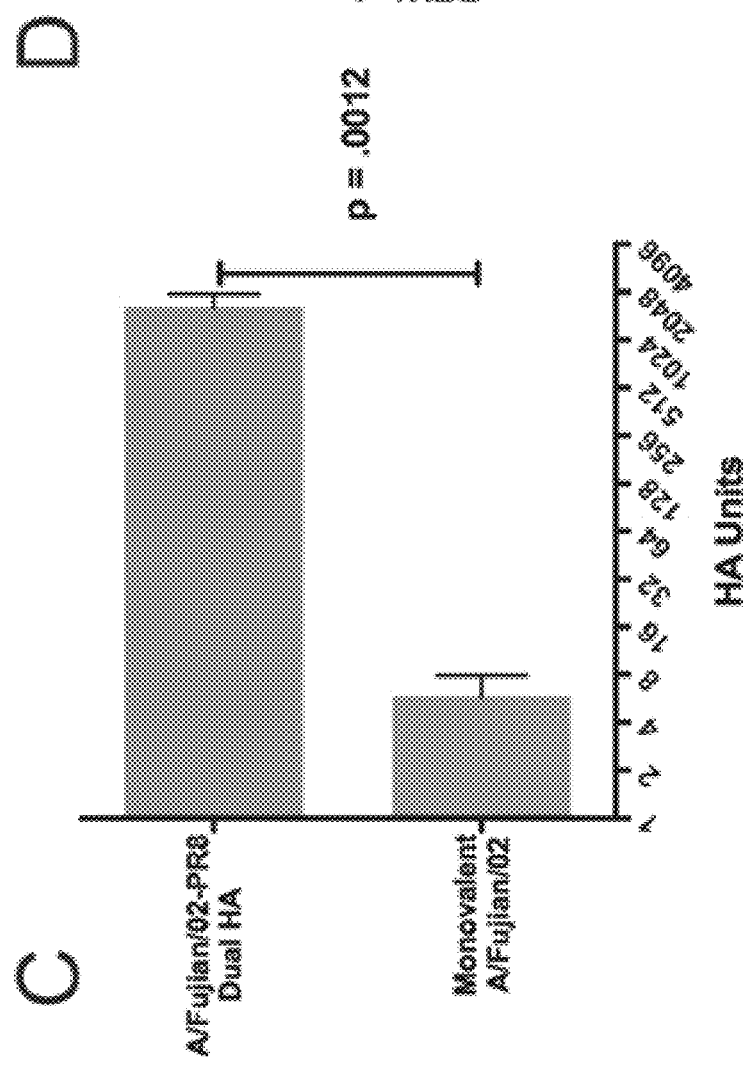
(FIG. 13D) Endpoint titer of the viruses from FIG. 13C.
Figure 13E:
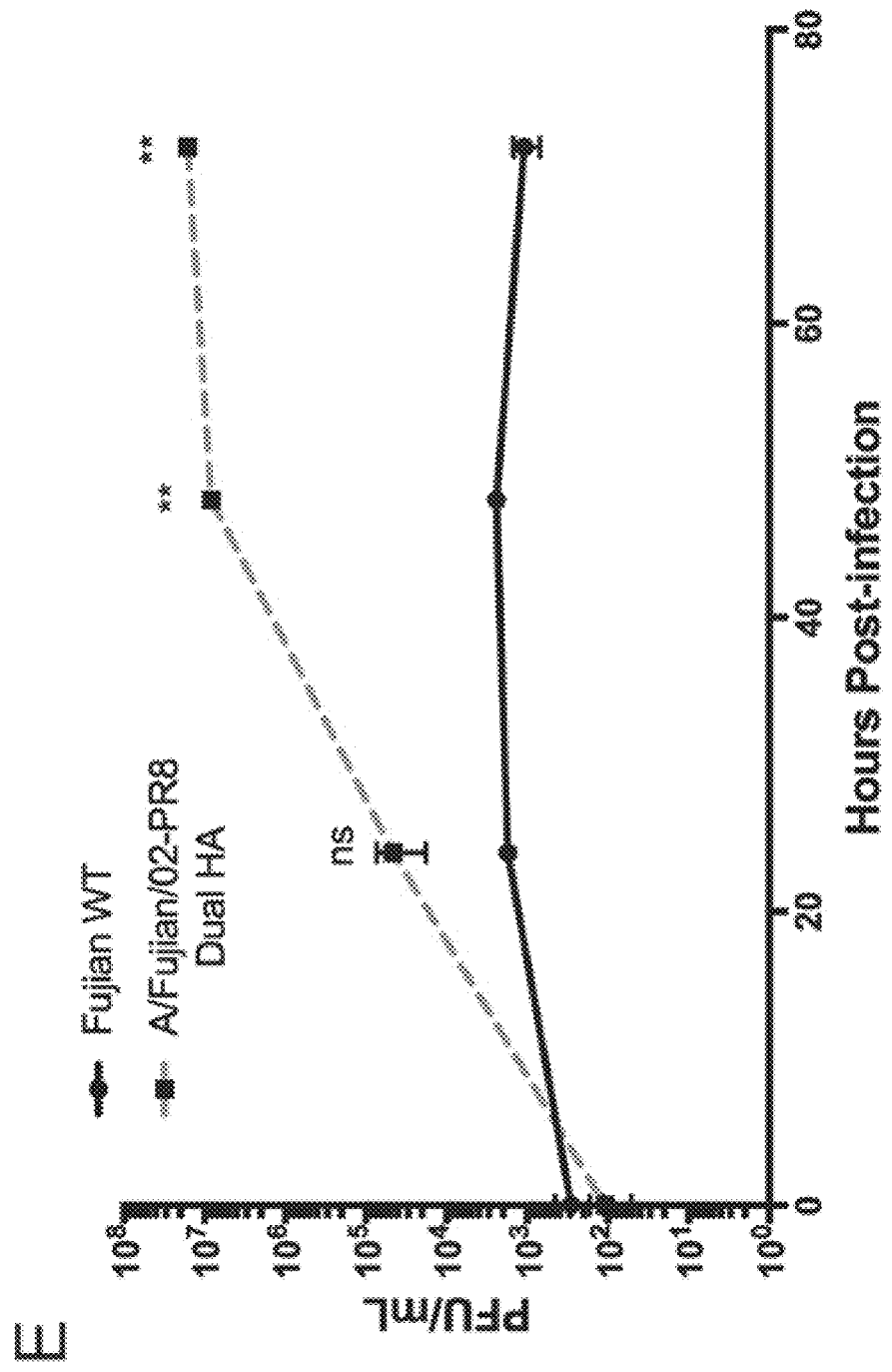
(FIG. 13E) Multicycle growth comparing the 6+2 reassortant in the PR8 background with A/Fujian/411/2002 glycoproteins and the Dual HA A/Fujian/411/2002-PR8 viruses.
Figure 13G:
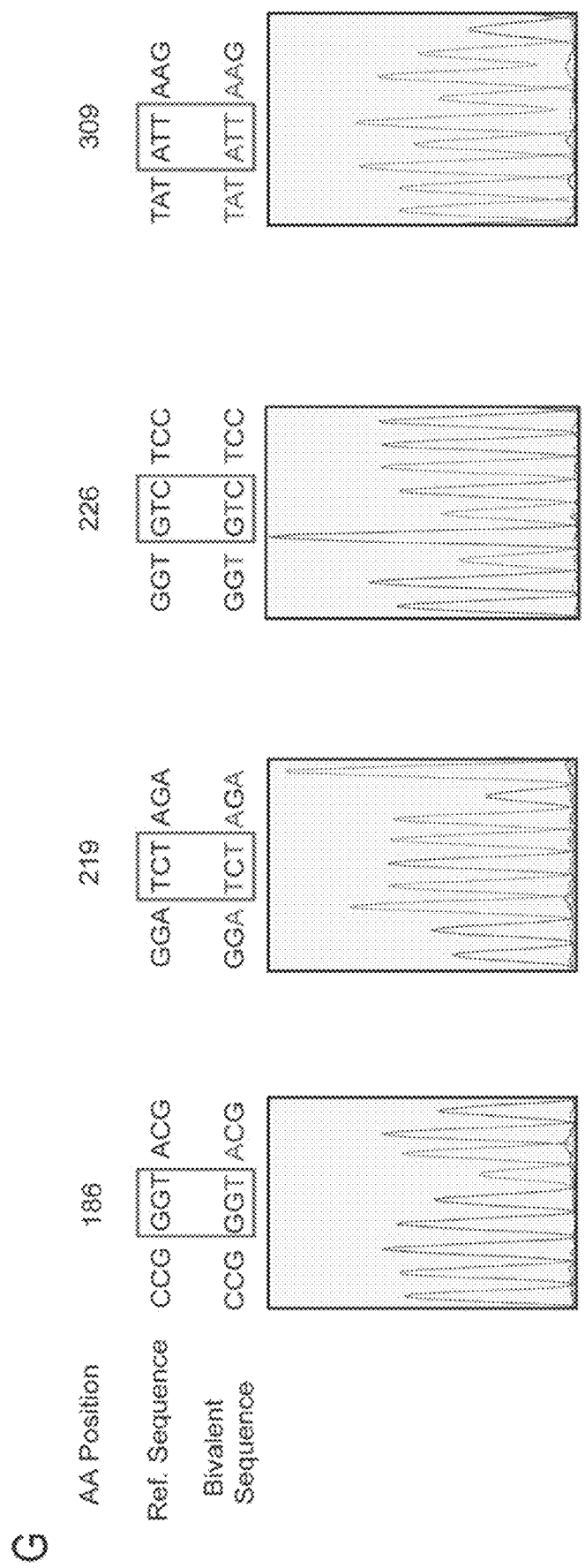
(FIG. 13G) Sequencing chromatograms of the A/Fujian/411/2002 HA in the bivalent background after egg growth. Red boxes indicate positions that have been previously published to mutate upon egg adaptation. For all panels *p≤0.05, **p≤0.001.

Finally, we wanted to evaluate the antigenic stability of an HA protein that is normally unstable during growth in embryonated chicken eggs. We selected the HA from A/Fujian/411/2002 (Fujian02), which is a well-characterized H3N2 strain that is known to grow extremely poorly in eggs and rapidly acquires adaptive HA mutations to facilitate growth (9, 10, 33). After rescuing a dual PR8/Fujian02 HA virus and growing a purified stock (which represents several rounds of growth) we observed high-titer growth in embryonated chicken eggs that was significantly increased (~4 orders of magnitude) compared to the standard 6+2 reassortant in the PR8 background (FIGS. 13C-E). Previous work has shown that robust growth A/Fujian/411/2002 requires the acquisition of several characteristic mutations to the HA protein (9, 10, 33). We therefore extracted RNA from our egg-grown dual PR8/Fujian02 population and sequenced the A/Fujian/411/2002 HA encoded in segment 6. Sequence analysis confirmed that the HA sequence of our dual HA virus did not contain any of the previously identified adaptive mutations (FIGS. 13F,G). In fact, there was not a single adaptive mutation in the entire ORF of the A/Fujian/411/2002 HA.

Discussion

We began this study with the goal of developing a viral genetic system that would allow antigenically stable, high titer growth of influenza viruses for vaccine production regardless of the intrinsic properties of a specific HA protein. We accomplished this task by expressing two functional HA proteins on a single, replication competent virus. We first developed new methods to express untagged proteins from IAV segments 4 and 6, and subsequently combined both the HA and NA proteins into segment 4. The final step was to add an additional HA into segment 6. Previous attempts to make bivalent influenza viruses have had limited success; the viruses required extensive genome alterations which resulted in a major decrease in fitness; greater than a three $\log_{10}$ reductions in titer (34, 35). Our dual HA viruses grew to high titers (~$10^8$ PFU/mL), and in some cases grew to titers indistinguishable from the parental PR8 strain (~$10^9$ PFU/mL). Our approach only required modifications to segments 4 and 6. Thus, this technology is fully compatible with current vaccine production methods which insert segments 4 and 6 from a circulating strain into a standardized genetic background (36). Importantly, our dual HA viruses displayed fundamentally reduced virulence, almost certainly due to the drastically increased genome size and the resulting effects on viral replication kinetics. The virus is also completely neutralized by polyclonal sera raised against either of the hemagglutinins, further highlighting the safety of this design.

Our dual HA virus approach was designed to promote recombinant virus growth irrespective of the nature of the specific HA used and fully preserve the viral antigenic epitopes. Some human strains of influenza virus (especially H3N2 strains) initially grow poorly as reassortants in embryonated chicken eggs (11, 37), which delays vaccine production. Recently, in 2009, poor growth of pandemic A/California/07/2009 H1N1 swine flu vaccine candidates delayed vaccine production by months (7, 8). And in 2002, the H3N2 A/Fujian/411/2002 strain grew so poorly that although it was the major circulating strain at the time, it could not be included in the seasonal vaccine (9, 10). This led to vaccine/circulating strain mismatch and poor vaccine efficacy in 2003/2004 (38). We have directly demonstrated the utility of our approach by generating a dual HA version of the A/Fujian/411/2002 strain. We observed immediate, robust virus growth in chicken eggs, that was substantially higher than a standard reassortant of A/Fujian/411/2002, and there was no requirement for adaptive mutations. The implication of our data is that, had this technology been available in 2002, A/Fujian/411/2002 could have been grown and included in the seasonal vaccine and human influenza disease that season likely would have been significantly reduced.

The other major goal of this study was to preserve the antigenicity of a human HA protein during growth in embryonated chicken eggs, where variants with altered antigenicity frequently arise due to differences in virus receptor structure between mammals and birds (39-41). Studies have shown that even in years where the strain selected for vaccine production matches the circulating strain, mutations acquired during amplification of the vaccine strain can lead to poor protection after vaccination (16, 42). Our results showed that by pairing an HA that allows high titer growth under the growth conditions of interest (such as from PR8), with a clinically relevant HA that is known to mutate easily (such as from A/Fujian/411/2002), the selective pressure to fix adaptive mutations in the second HA can be entirely eliminated. While difficult to grow strains can eventually be adapted to grow to high titers in eggs, this requires the serial passage of the relevant IAV reassortant in eggs resulting in the acquisition of adaptive mutations in the viral glycoproteins, which must then be carefully screened for effects on antigenicity (37). Our dual HA genetic approach completely eliminated the need for this time consuming step.

We also observed increased HA density on the surface of the dual HA virion, which by definition increases the amount of HA antigen relative to other viral proteins. Thus, a dual HA virus has the potential to deliver the same amount of HA antigen in lower amount of total protein, which may increase vaccine tolerance and decrease side effects. Finally, this technology is not restricted to expressing solely influenza virus proteins. It can theoretically also be used as a platform to produce vaccines with a combination of influenza and non-influenza antigens, while nevertheless still utilizing the current influenza vaccine production infrastructure.

In conclusion, we have developed two independent ways to express foreign proteins in IAV and combined those approaches to generate a replication competent, dual HA "bivalent" virus. We have shown that our viruses require no adaptation step and allow high titer, antigenically stable growth of essentially any clinically relevant influenza A or B virus HA protein. This technology is fully compatible with current vaccine production practices and can be immediately utilized to facilitate rapid and cost effective production, as well as potentially increase protective efficacy, of influenza virus vaccines.

Materials and Methods

Cells and Antibodies

Madin-Darby canine kidney (MDCK) cells were grown in minimal essential medium (MEM) supplemented with 10% fetal bovine serum, HEPES, NaHCO$_3$, Gluta-max and penicillin-streptomycin. 293T cells were grown in Dulbecco's modified eagle medium (DMEM) supplemented with 10% fetal bovine serum, Gluta-max and penicillin-streptomycin. Monoclonal antibodies specific for PR8 H1 (PY102), HK68 H3 (XY102), and influenza virus M1 (E10) were provided by Tom Moran at the Experimental Therapeutics Institute at the Icahn School of Medicine at Mount Sinai.

Cloning and Rescue of Recombinant Viruses

Recombinant viruses were generated as previously described (43) by use of the bicystronic pDZ rescue plasmid system. Viral protein sequences were generated from rescue plasmids from the A/Puerto Rico/8/1934 H1N1 background. Fluorescent proteins and linker sequences were synthesized using influenza A virus codon usage preferences (IDT) and viral packaging signals were used as previously described (44). Primer sequences are listed in Table 3. The PR8 NA flag virus has been previously described (29). InfusionHD (Clontech) or NEBuilder HiFI DNA Assembly Kit (NEB) were used to assemble DNA fragments before transformation into Clontech Stellar™ Competent Cells, as per manufacturer's instructions. Insert size was then confirmed by colony PCR and sequenced via Sanger sequencing before use in viral rescue. The plasmid (kindly provided by Dr. Richard Webby) for the rescue of the WT A/Fujian/411/2002 reassortant virus is of the same sequence as deposited under the GenBank accession number: CY112933.1 with three nonsynonomous nucleotide changes, a T to A at position 610, and an A to G at 736, and 987. The following viral HA genes were synthesized (IDT) with silent mutations to eliminate the normal packaging signals. The sequence used for the A/Fujian/411/2002 dual HA virus is the same as deposited under the GenBank accession number: CY112933.1 with one nonsynonomous nucleotide change, a G to T at position 769. The sequence used for the A/Victoria/210/2009 dual HA virus is the same as deposited under the GenBank accession number: HM459583.1. The sequence used for the B/Malaysia/2004 dual HA virus is the same as deposited under the GenBank accession number: CY119706.1 with two nonsynonomous nucleotide changes: a A to G at position 42, and a C to T at position 638. The sequence used for the B/Yamagata/1988 dual HA virus is the same as deposited under the GenBank accession number: CY018765.1 with three nonsynonomous nucleotide changes, a G to A at positions 484 and 645, and a C to A at position 652. Virus rescue plasmids were transfected into 293T cells using the Mirus Transit LT-1 reagent along with the remaining viral RNA segments from WT PR8. Rescued virus was then propagated in 10-day-old chicken eggs (Charles Rivers) at 37° C. for 72 hrs.

TABLE 3

Primers used in this study-all sequences 5' to 3'

| Construct | Forward Primer | Reverse Primer |
|---|---|---|
| mRub2-2A-HA Fragment 1 | CTCCGAAGTTGGGGGGAGCAA AAGCAGG (SEQ ID NO: 6) | TTATAGAGTTCATCCATTCCT CCTC (SEQ ID NO: 7) |
| mRub2-2A-HA Fragment 2 | ATGGATGAACTCTATAAAGGAT CTGGGGCTACCAACTTCAGTCT (SEQ ID NO: 8) | TGGGCCGCCGGGTTATTAGTA GAAACAAGG (SEQ ID NO: 9) |
| mNeon-2A-HA Fragment 1 | CTCCGAAGTTGGGGGGAGCAA AAGCAGG (SEQ ID NO: 10) | ATATTGTGTCTGCCGCGGCCG CC (SEQ ID NO: 11) |
| mNeon-2A-HA Fragment 2 | CGGACGCAGACACAATATGTAT AGGCTACCATGCGAACAATTCA (SEQ ID NO: 12) | TGGGCCGCCGGGTTATTAGTA GAAACAAGG (SEQ ID NO: 13) |
| NA-Furin-2A- mNeon Fragment 1 | CTCCGAAGTTGGGGGGAGCGA AAGCAGG (SEQ ID NO: 14) | CTCCAGTCTACGGTGTCACTA TTCACGCCAAAAGAAATGCT (SEQ ID NO: 15) |
| NA-Furin-2A- mNeon Fragment 2 | TGACACCGTAGACTGGAGCTGG CCGG (SEQ ID NO: 16) | TGGGCCGCCGGGTTATTAGTA GAAACAAGG (SEQ ID NO: 17) |

TABLE 3-continued

Primers used in this study-all sequences 5' to 3'

| Construct | Forward Primer | Reverse Primer |
| --- | --- | --- |
| S4 H1N1 NA/HA Fragment 1 | CTCCGAAGTTGGGGGGAGCAA AAGCAGG (SEQ ID NO: 18) | CCTGCATTCCAAGTGAGAAC ATGAAA (SEQ ID NO: 19) |
| S4 H1N1 NA/HA Fragment 2 | TCTCACTTGGAATGCAGGACCTT TTTTCTGACCCAAGGTGCCTT (SEQ ID NO: 20) | GTTGGTAGCCCCAGATGGGG TTCTCTTTCTTTTATCGATAGA AA (SEQ ID NO: 21) |
| S4 H1N1 NA/HA Fragment 3 | GGATCTGGGGCTACCAACTTCA GTCT (SEQ ID NO: 22) | TGGGCCGCCGGGTTATTAGTA GAAACAAGG (SEQ ID NO: 23) |
| NA-Flag-Furin-2A-mNeon Fragment 1 | CTCCGAAGTTGGGGGGAGCGA (SEQ ID NO: 24) | GTCATCGTCATCTTTATAATC TACCCAGGTGCTATTTTTATA GGTAA (SEQ ID NO: 25) |
| NA-Flag-Furin-2A-mNeon Fragment 1 | TATAAAGATGATGATGACAAGG ACACAACTTCAGTGATATTAAC (SEQ ID NO: 26) | TGGGCCGCCGGGTTATTAGTA GAAACAAGG (SEQ ID NO: 27) |
| ZsGreen Seg 6 | CTCCGAAGTTGGGGGGAGCGA AAGCAGG (SEQ ID NO: 28) | TGGGCCGCCGGGTTATTAGTA GAAACAAGG (SEQ ID NO: 29) |
| HK 68 HA Seg 6 | CTCCGAAGTTGGGGGGAGCGA AAGCAGG (SEQ ID NO: 30) | TGGGCCGCCGGGTTATTAGTA GAAACAAGG (SEQ ID NO: 31) |
| PR8 HA Seg 6 | CTCCGAAGTTGGGGGGAGCGA AAGCAGG (SEQ ID NO: 32) | TGGGCCGCCGGGTTATTAGTA GAAACAAGG (SEQ ID NO: 33) |
| Yamagata 88 HA Seg 6 | ACTGGAATTTGCAACCAAGATA TCGCCACCATGAAGGCAATAAT TGTACTACTCAT (SEQ ID NO: 34) | TCTAGCCCTGTTAGCTCAGTT TAAACTTATAGACAGATGGA GCAAGAAACAT (SEQ ID NO: 35) |
| Malaysia 04 HA Seg 6 | ACTGGAATTTGCAACCAAGATA TCGCCACCATGAAGGCAATAAT TGTACTACTCAT (SEQ ID NO: 36) | TCTAGCCCTGTTAGCTCAGTT TAAACTTATAGACAGATGGA GCAAGAAACAT (SEQ ID NO: 37) |
| Fujian 2002 HA Seg 6 | ACTGGAATTTGCAACCAAGATA TCGCCACCATGAAGACCATCAT AGCACTGTCAT (SEQ ID NO: 38) | ACAGTCTAGCCCTGTTAGCTC AGTTTAAACTCAGATGCAAAT ATTACACCGTATA (SEQ ID NO: 39) |
| Victoria 2009 HA Seg 6 | ACTGGAATTTGCAACCAAGATA TCGCCACCATGAAAACAATTAT CGCTC (SEQ ID NO: 40) | ACAGTCTAGCCCTGTTAGCTC AGTTTAAACTCAAATACAGAT GTTGCAT (SEQ ID NO: 41) |

Viral Titer

Prior to titering, 30-50 pfu of each dilution-purified stock of virus was injected into eggs and incubated at 37 C for 72 hrs. Then the allantoic fluid was collected, and viral titer was determined via standard plaque assay procedures on MDCK cells. Cells were incubated for one hour in 333 μL of diluted virus suspension at 37° C., before removing the virus and applying the agar overlay. Cells were then incubated at 37° C. for 72 hours before being fixed in 4% paraformaldehyde in PBS for at least 4 hours. The 4% PFA was then aspirated and the agar layer removed before washing cells in PBS and incubating at 4° C. overnight in mouse serum from PR8 infected mice. Mouse serum was diluted 1:2000 in antibody dilution buffer, which was made using 5% w/v non-fat dried milk and 0.05% Tween-20 in PBS. After the overnight incubation in primary antibody, plaque assays were washed with PBS three times and then incubated for one hour in anti-mouse IgG HRP conjugated sheep antibody (GE Healthcare) diluted 1:4000 in antibody dilution buffer. Assays were then washed three additional times with PBS and incubated in 0.5 mL of True Blue reagent for 30 minutes to allow for the staining of plaques. Once plaques were visible, plates were washed with water and allowed to dry before counting (only wells with greater than 5 plaques were used for the calculation of endpoint titer).

Microscopy Timecourse

Microscopy images were taken using MDCK cells infected with varying MOIs of either the reporter virus or WT virus. Cells were infected in 300 μl of virus for 1 hr at 37 C, after this incubation period the infection media was removed and cells were placed in complete media. At the indicated time after infection MDCK media was removed and replaced with 1 mL of warm PBS. Cells were then incubated with Hoechst stain (0.5 μl/mL of PBS) to allow for the staining of nuclei and imaging was performed on the ZOE Fluorescent Cell Imager (BioRad). Images were then processed with ImageJ (NIH).

Flow Cytometry

MDCK cells were infected for approximately 24 hr before being trypsinized and collected for flow cytometry. Raw data was collected on a FACSCanto II (BD) machine and data was processed with FlowJo software.

Viral Passaging & RT-PCR

Virus was passaged in 10-day-old eggs purchased from Charles River Laboratories. 30-50 pfu of each virus was injected into two eggs for each passage. Eggs were incubated for 72 hrs at 37 C in a humidified egg incubator before collection of the allantoic fluid. Virus was confirmed in the sample by hemagglutination assay before being injected into a new set of eggs. The passage 0 and 4 samples were subjected to Trizol RNA extraction. RT-PCR was performed using the Superscript III One-Step RT-PCR Kit according to manufacturer's instruction with segment specific primers. Samples were run on a 1% Agarose gel and imaged. Microscopy was taken 24 hr post infection and performed in the same manner as described previously for timecourses.

Western Blotting

Virions were concentrated using a 30% sucrose cushion for 1 hr at 25,700 RPM on the Sorvall TH-641 swinging bucket rotor. Equal amounts of protein were loaded into 4-20% acrylamide gels and transferred to a nitrocellulose membrane. 5% non-fat dry milk in PBS+0.1% tween 20 was used to block for 1 hour and a 1:1000 dilution of primary antibodies PY102, XY102 or E10 was incubated overnight. An anti-mouse-HRP secondary antibody was incubated for 1 hour and the blot was exposed to film. The membrane was then stripped for re-probing with the E10 M1 antibody.

Hemagglutination Inhibition Assay

Hemagglutination Inhibition assays (HAIs) were performed using $10^7$ pfu of virus per well, diluted in cold PBS. These samples were then mixed with a range of dilutions of monoclonal antibodies or sera collected from vaccinated mice. All data shown containing sera is from pooled, Receptor Destroying Enzyme (RDE) treated samples. All samples were treated according to Denka Seiken Co.'s protocol with RDE (II) Seiken (370013). Once virus and antibody were mixed together, an equal amount of chicken blood diluted 1:40 in cold PBS was mixed with each sample and incubated at 4 C for approximately 30 minutes.

Plaque Reduction Assay

All plaque reduction assays were performed on MDCK cells. Virus was diluted to 50 plaque-forming units (PFU) and mixed with antibody before being incubated at room temperature for 30 minutes. The virus/antibody mixture was then applied to the cells and incubated for an additional 30 minutes at 37 C, shaking the samples every 10-15 minutes to ensure cells are evenly covered by the mixture. After the incubation, the solution was aspirated and an agar overlay was applied. Plaque assays were then performed as described above, and plaques were counted. All data shown containing sera is from pooled, Receptor Destroying Enzyme (RDE) treated samples. All samples were treated according to Denka Seiken Co.'s protocol with RDE (II) Seiken (370013).

Sandwich ELISA Assays

For the sandwich enzyme-linked immunosorbent assay (ELISA), 96-well plates were coated with 100 μL of 5 μg/mL of mouse anti-H3 XY102 (IgG2) by overnight incubation at 4 C in a carbonate buffer. Plates were then washed 2× with 150 μL of PBS and blocked with 1% BSA in PBS for 1-2 hours at room temperature. A two-fold serial dilution in the blocking buffer was then added to the plate and incubated overnight at 4 C (a starting concentration of 5% BSA was used for the BSA control). After this incubation, plates were washed 2× with PBS and then incubated with 100 μL of 1 μg/mL of the subtype H1 specific antibody PY102 (IgG1) for 3 hours at 37 C and detected by goat anti-mouse IgG1 conjugated with HRP (Thermo Fischer Scientific) (1:2000).

ELISA Assays

Virions were concentrated using a 30% sucrose cushion for 1 hr at 25,700 RPM on the Sorvall TH-641 swinging bucket rotor. Samples were then resuspended in 1 mL of PBS and protein concentration was determined via Bradford. 96-well plates were then coated at 4 C with a range of protein concentrations using a carbonate buffer overnight. All samples were diluted to the same starting concentration (5% BSA was used as the starting concentration for the BSA control). Plates were then washed 2× with 150 μl of PBS and blocked with 1% BSA in PBS for 1-2 hours at room temperature. After this incubation, plates were washed 2× with PBS and then incubated overnight at 4 C in 100 μl of a mixture of 1:2000 PY102 (an H1 specific mouse antibody) and 1:1000 XY102 (an H3 specific mouse antibody) diluted in 1% BSA/PBS. Plates were then washed 2× with PBS and incubated for 1-2 hours at room temp in 100 μl of 1% BSA/PBS containing 1:5000 Goat anti-mouse HRP conjugated Ab. Plates were then washed 2× with PBS and incubated in TMB HRP substrate for approximately 20 minutes. At this time, or when the lowest dilution began to saturate with color, 100 μl of 1M sulfuric acid was added to each well to stop the reaction and absorbance was measured at 450 nm on a plate reader.

Animal Infections

Eight to ten-week-old C57BL/6 mice were used for all experiments, with a sample size of at least 4 mice per dose of virus. Prior to infection mice were anesthetized with a 100 μl injection of Ketamine/Xylazine mixture. Mice were weighed and marked and 40 μl of virus diluted in pharmaceutical grade PBS was administered intranasally. Mice were weighed daily, and euthanized once their body weight reached 80% of the starting weight measured prior to infection as a humane endpoint. Euthanasia was performed via $CO_2$ as the primary method, and a bilateral thoracotomy was performed as the secondary method. Viral challenge of vaccinated mice was performed using this procedure as well. All procedures were approved by the Duke University IACUC.

Vaccination of Mice

Mice were vaccinated with inactivated virus in order to examine the potential efficacy of our virus as a vaccine. Virus was concentrated and inactivated with PFA. Prior to injection, PFA was removed via Thermo-Scientific Slide-a-Lyzer Dialysis Cassettes according to manufacturer instructions. Protein samples were then diluted to 70 μg/mL in pharmaceutical grade PBS. Mice were sedated as previously mentioned and a 100 μl vaccination was administered intramuscularly into the right leg of each mouse. After two weeks, mice were vaccinated once more in the same fashion and given another two-week period before challenging or collecting serum.

Cell-Based ELISA 293T cells were trypsinized and resuspended in 293T media at a concentration of $1\times10^5$ cells/mL and plated on 96-well plates that were poly-1-lysine treated. A transfection mixture was made with 900 μl of optimem, 30 μl of Transit LT-1 and 10 μg of DNA (either PR8 (H1) Hemagglutinin in the pDZ plasmid, or HK 68 (H3) Hemagglutinin in the pDZ plasmid). This mixture was incubated for 5 minutes, before being added to the 293T cells in suspension. Plates were incubated at 37 C for two days before fixing in 100 μl of 4%

PFA for 5 minutes. Plates were then put through the same ELISA procedure listed above.

Neuraminidase Activity Assay

Flag-Tagged Neuraminidase from both WT-PR8 and the NA-Furin-mNeon virus was concentrated and purified from virions using Sigma-Aldrich Anti-Flag M2 Magnetic Beads (M8823) according to manufacturerer's protocol. A Bradford assay was then performed to measure protein concentration and standardize the samples. Once this was done, the Sigma-Aldrich Neuraminidase Activity Assay kit (MAK121) was used according to manufacturerer's protocol to evaluate the activity of the respective Neuraminidase proteins.

Statistical Analysis

Comparison between datasets was performed using an unpaired, two-tailed Student's t-test unless otherwise stated. * or ** indicate p≤0.05 and 0.001, respectively. Analysis was performed using Prism 7 (Graphpad) software.

Example 2

Packaging and Delivery of Heterologous Polypeptides in Engineered Influenza Viruses To investigate whether other heterologous polypeptides besides hemagglutinin (HA) could be packaged and expressed in influenza viruses, we introduced separately a TmZsGreen polypeptide including the ZsGreen protein with a transmembrane from the influenza NA protein and the full-length E protein from Zika virus into pDZ plasmids. The TmZsGreen polypeptide was introduced into a pDZ plasmid encoding segment 4 of an influenza virus. See FIG. 15A. The TmZsGreen polypeptide could also have been introduced into a pDZ plasmid encoding segment 6 of an influenza virus and cotransfected with a pDZ plasmid encoding HA and NA in segment 4. See FIG. 15B. The E protein from Zika virus was introduced into a pDZ plasmid encoding segment 6 of an influenza virus and was cotransfected with a pDZ plasmid encoding HA and NA in segment 4. These pDZ plasmids were transfected into 293T cells along with pDZ plasmids encoding the remaining segments of influenza virus.

Figure 16C:
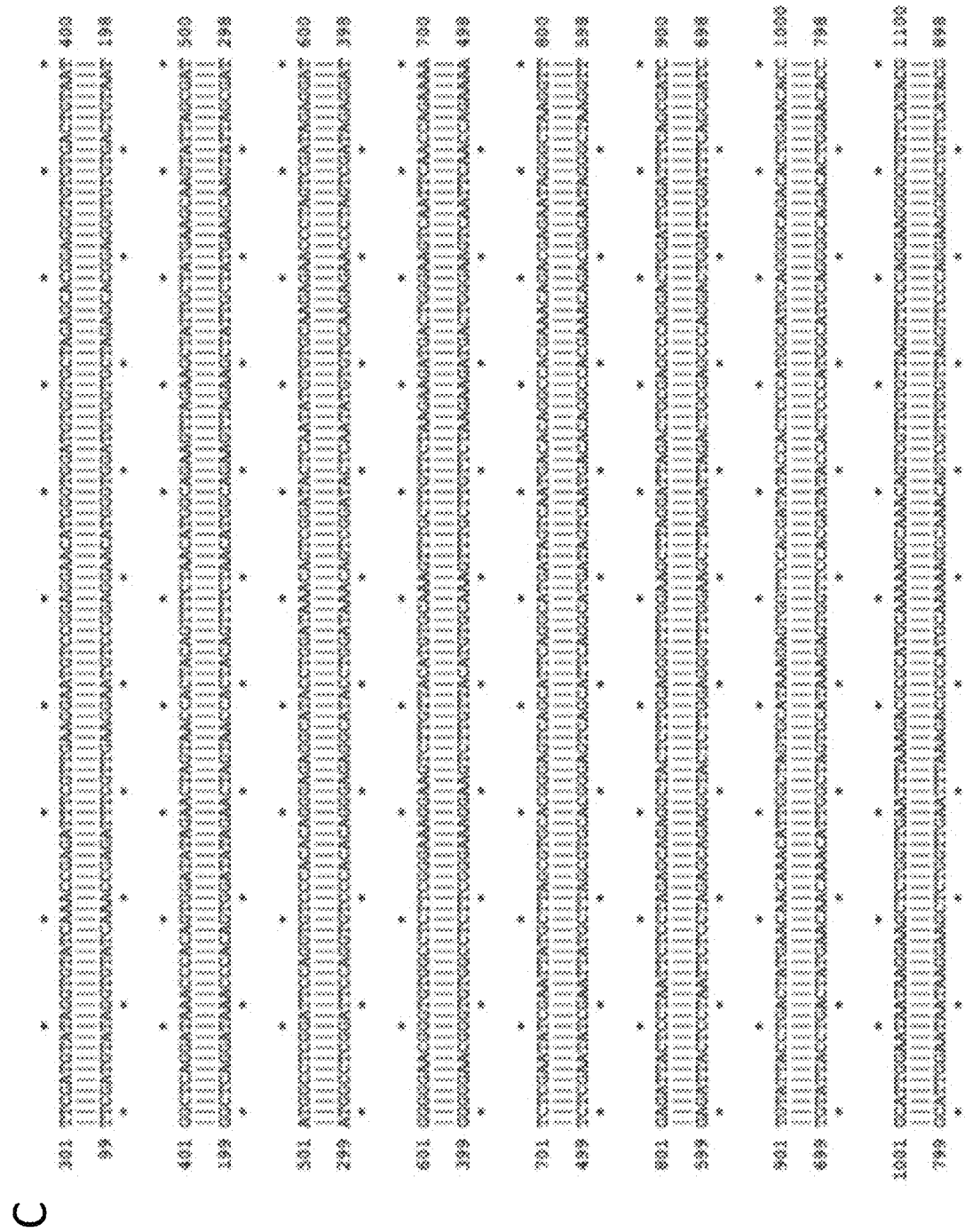
(FIG. 16C) Representative sequence alignment of the Full-Length E protein from the Zika virus in segment 6 construct (SEQ ID NO: 55), and the RT-PCR amplification of segment 6 from a rescued virus harboring that construct.

The presence of the TmZsGreen polypeptide in rescued viruses was detected using fluorescence microscopy. See FIGS. 15D and 16A-16B. The presence of the Zika virus E protein was detected by RT-PCR and sequencing from rescued virus. See FIGS. 16C-16D.

REFERENCES

1. Shaw M L, Palese P. 2013. Orthomyxoviruses, p 1151-1185. In Knipe D M, Howley P M (ed), Fields Virology. Lippincott Williams and Wilkins, Philadelphia.

2. WHO. 2014. Influenza (Seasonal): Fact Sheet No. 211.

3. Pica N, Palese P. 2013. Toward a universal influenza virus vaccine: prospects and challenges. Annu Rev Med 64:189-202.

4. Gerdil C. 2003. The annual production cycle for influenza vaccine. Vaccine 21:1776-1779.

5. Cox M M, Izikson R, Post P, Dunkle L. 2015. Safety, efficacy, and immunogenicity of Flublok in the prevention of seasonal influenza in adults. Ther Adv Vaccines 3:97-108.

6. Soema P C, Kompier R, Amorij J P, Kersten G F. 2015. Current and next generation influenza vaccines: Formulation and production strategies. Eur J Pharm Biopharm 94:251-263.

7. Robertson J S, Nicolson C, Harvey R, Johnson R, Major D, Guilfoyle K, Roseby S, Newman R, Collin R, Wallis C, Engelhardt O G, Wood J M, Le J, Manojkumar R, Pokorny B A, Silverman J, Devis R, Bucher D, Verity E, Agius C, Camuglia S, Ong C, Rockman S, Curtis A, Schoofs P, Zoueva O, Xie H, Li X, Lin Z, Ye Z, Chen L M, O'Neill E, Balish A, Lipatov A S, Guo Z, Isakova I, Davis C T, Rivailler P, Gustin K M, Belser J A, Maines T R, Tumpey T M, Xu X, Katz J M, Klimov A, Cox N J, Donis R O. 2011. The development of vaccine viruses against pandemic A(H1N1) influenza. Vaccine 29:1836-1843.

8. Jin H, Chen Z. 2014. Production of live attenuated influenza vaccines against seasonal and potential pandemic influenza viruses. Curr Opin Virol 6:34-39.

9. Lu B, Zhou H, Ye D, Kemble G, Jin H. 2005. Improvement of influenza A/Fujian/411/02 (H3N2) virus growth in embryonated chicken eggs by balancing the hemagglutinin and neuraminidase activities, using reverse genetics. J Virol 79:6763-6771.

10. Widjaja L, Ilyushina N, Webster R G, Webby R J. 2006. Molecular changes associated with adaptation of human influenza A virus in embryonated chicken eggs. Virology 350:137-145.

11. Lu B, Zhou H, Chan W, Kemble G, Jin H. 2006. Single amino acid substitutions in the hemagglutinin of influenza A/Singapore/21/04 (H3N2) increase virus growth in embryonated chicken eggs. Vaccine 24:6691-6693.

12. Medeiros R, Escriou N, Naffakh N, Manuguerra J C, van der Werf S. 2001. Hemagglutinin residues of recent human A(H3N2) influenza viruses that contribute to the inability to agglutinate chicken erythrocytes. Virology 289:74-85.

13. Mochalova L, Gambaryan A, Romanova J, Tuzikov A, Chinarev A, Katinger D, Katinger H, Egorov A, Bovin N. 2003. Receptor-binding properties of modern human influenza viruses primarily isolated in Vero and MDCK cells and chicken embryonated eggs. Virology 313:473-480.

14. Tricco A C, Chit A, Soobiah C, Hallett D, Meier G, Chen M H, Tashkandi M, Bauch C T, Loeb M. 2013. Comparing influenza vaccine efficacy against mismatched and matched strains: a systematic review and meta-analysis. BMC Med 11:153.

15. Belongia E A, Kieke B A, Donahue J G, Greenlee R T, Balish A, Foust A, Lindstrom S, Shay D K, Marshfield Influenza Study G. 2009. Effectiveness of inactivated influenza vaccines varied substantially with antigenic match from the 2004-2005 season to the 2006-2007 season. J Infect Dis 199:159-167.

16. Skowronski D M, Janjua N Z, De Serres G, Sabaiduc S, Eshaghi A, Dickinson J A, Fonseca K, Winter A L, Gubbay J B, Krajden M, Petric M, Charest H, Bastien N, Kwindt T L, Mahmud S M, Van Caeseele P, Li Y. 2014. Low 2012-13 influenza vaccine effectiveness associated with mutation in the egg-adapted H3N2 vaccine strain not antigenic drift in circulating viruses. PLoS One 9:e92153.

17. Raymond D D, Stewart S M, Lee J, Ferdman J, Bajic G, Do K T, Ernandes M J, Suphaphiphat P, Settembre E C, Dormitzer P R, Del Giudice G, Finco O, Kang T H, Ippolito G C, Georgiou G, Kepler T B, Haynes B F, Moody M A, Liao H X, Schmidt A G, Harrison S C. 2016. Influenza immunization elicits antibodies specific for an egg-adapted vaccine strain. Nat Med 22:1465-1469.

18. Fiege J K, Langlois R A. 2015. Investigating influenza A virus infection: tools to track infection and limit tropism. J Virol 89:6167-6170.

19. Breen M, Nogales A, Baker S F, Martinez-Sobrido L. 2016. Replication-Competent Influenza A Viruses Expressing Reporter Genes. Viruses 8.

20. Sekikawa K, Lai C J. 1983. Defects in functional expression of an influenza virus hemagglutinin lacking the signal peptide sequences. Proc Natl Acad Sci USA 80:3563-3567.

21. Spitzer N, Sammons G S, Price E M. 2011. Autofluorescent cells in rat brain can be convincing impostors in green fluorescent reporter studies. Journal of Neuroscience Methods 197:48-55.

22. Davis A S, Richter A, Becker S, Moyer J E, Sandouk A, Skinner J, Taubenberger J K. 2014. Characterizing and Diminishing Autofluorescence in Formalin-fixed Paraffin-embedded Human Respiratory Tissue. Journal of Histochemistry & Cytochemistry 62:405-423.

23. Chudakov D M, Matz M V, Lukyanov S, Lukyanov K A. 2010. Fluorescent Proteins and Their Applications in Imaging Living Cells and Tissues. Physiological Reviews 90:1103-1163.

24. Pandelieva A T, Baran M J, Calderini G F, McCann J L, Tremblay V, Sarvan S, Davey J A, Couture J F, Chica R A. 2016. Brighter Red Fluorescent Proteins by Rational Design of Triple-Decker Motif. Acs Chemical Biology 11:508-517.

25. Shaner N C, Lambert G G, Chammas A, Ni Y H, Cranfill P J, Baird M A, Sell B R, Allen J R, Day R N, Israelsson M, Davidson M W, Wang J. 2013. A bright monomeric green fluorescent protein derived from Branchiostoma lanceolatum. Nature Methods 10:407-+.

26. Li F, Feng L, Pan W, Dong Z, Li C, Sun C, Chen L. 2010. Generation of replication-competent recombinant influenza A viruses carrying a reporter gene harbored in the neuraminidase segment. J Virol 84:12075-12081.

27. Pan W, Dong Z, Li F, Meng W, Feng L, Niu X, Li C, Luo Q, Li Z, Sun C, Chen L. 2013. Visualizing influenza virus infection in living mice. Nat Commun 4:2369.

28. Fang J, Yi S, Simmons A, Tu G H, Nguyen M, Harding T C, VanRoey M, Jooss K. 2007. An antibody delivery system for regulated expression of therapeutic levels of monoclonal antibodies in vivo. Mol Ther 15:1153-1159.

29. Heaton N S, Moshkina N, Fenouil R, Gardner T J, Aguirre S, Shah P S, Zhao N, Manganaro L, Hultquist J F, Noel J, Sachs D, Hamilton J, Leon P E, Chawdury A, Tripathi S, Melegari C, Campisi L, Hai R, Metreveli G, Gamarnik A V, Garcia-Sastre A, Greenbaum B, Simon V, Fernandez-Sesma A, Krogan N J, Mulder L C, van Bakel H, Tortorella D, Taunton J, Palese P, Marazzi I. 2016. Targeting Viral Proteostasis Limits Influenza Virus, HIV, and Dengue Virus Infection. Immunity 44:46-58

30. Gao Q, Brydon E W, Palese P. 2008. A seven-segmented influenza A virus expressing the influenza C virus glycoprotein HEF. J Virol 82:6419-6426.

31. Cwach K T, Sandbulte H R, Klonoski J M, Huber V C. 2012. Contribution of murine innate serum inhibitors toward interference within influenza virus immune assays. Influenza and Other Respiratory Viruses 6:127-135.

32. Kim H R, Lee K K, Kwon Y K, Kang M S, Moon O K, Park C K. 2012. Comparison of serum treatments to remove nonspecific inhibitors from chicken sera for the hemagglutination inhibition test with inactivated H5N1 and H9N2 avian Influenza A virus subtypes. Journal of Veterinary Diagnostic Investigation 24:954-958.

33. Nicolson C, Major D, Wood J M, Robertson J S. 2005. Generation of influenza vaccine viruses on Vero cells by reverse genetics: an H5N1 candidate vaccine strain produced under a quality system. Vaccine 23:2943-2952.

34. Gao Q, Lowen A C, Wang T T, Palese P. 2010. A nine-segment influenza a virus carrying subtype H1 and H3 hemagglutinins. J Virol 84:8062-8071.

35. Pena L, Sutton T, Chockalingam A, Kumar S, Angel M, Shao H, Chen H, Li W, Perez D R. 2013. Influenza viruses with rearranged genomes as live-attenuated vaccines. J Virol 87:5118-5127.

36. Wong S S, Webby R J. 2013. Traditional and new influenza vaccines. Clin Microbiol Rev 26:476-492.

37. Barman S, Franks J, Turner J C, Yoon S W, Webster R G, Webby R J. 2015. Egg-adaptive mutations in H3N2v vaccine virus enhance egg-based production without loss of antigenicity or immunogenicity. Vaccine 33:3186-3192.

38. Ritzwoller D P, Bridges C B, Shetterly S, Yamasaki K, Kolczak M, France E K. 2005. Effectiveness of the 2003-2004 influenza vaccine among children 6 months to 8 years of age, with 1 vs 2 doses. Pediatrics 116:153-159.

39. Burnet F M. 1936. Influenza virus on the developing egg: I. Changes associated with the development of an egg-passage strain of virus. British Journal of Experimental Pathology 17:282-293.

40. Rocha E P, Xu X, Hall H E, Allen J R, Regnery H L, Cox N J. 1993. Comparison of 10 influenza A (H1N1 and H3N2) haemagglutinin sequences obtained directly from clinical specimens to those of MDCK cell- and egg-grown viruses. J Gen Virol 74 (Pt 11):2513-2518.

41. Gambaryan A S, Marinina V P, Tuzikov A B, Bovin N V, Rudneva I A, Sinitsyn B V, Shilov A A, Matrosovich M N. 1998. Effects of host-dependent glycosylation of hemagglutinin on receptor-binding properties on H1N1 human influenza A virus grown in MDCK cells and in embryonated eggs. Virology 247:170-177.

42. Chen Z, Zhou H, Jin H. 2010. The impact of key amino acid substitutions in the hemagglutinin of influenza A (H3N2) viruses on vaccine production and antibody response. Vaccine 28:4079-4085.

43. Heaton N S, Leyva-Grado V H, Tan G S, Eggink D, Hai R, Palese P. 2013. In vivo bioluminescent imaging of influenza a virus infection and characterization of novel cross-protective monoclonal antibodies. J Virol 87:8272-8281.

44. Gao Q, Chou Y Y, Doganay S, Vafabakhsh R, Ha T, Palese P. 2012. The influenza A virus PB2, PA, NP, and M segments play a pivotal role during genome packaging. J Virol 86:7043-7051.

We claim:

1. An engineered influenza virus segment 4 polynucleotide encoding a polypeptide comprising from N-terminus to C-terminus: a neuraminidase (NA) polypeptide, a furin site, a self-cleaving 2A polypeptide, and a first hemagglutinin (HA) polypeptide, wherein both the NA polypeptide and the first HA polypeptide that are expressed from the segment 4 polynucleotide are free of residual amino acids from the furin site and the self-cleaving 2A polypeptide.

2. The polynucleotide of claim 1, further comprising a polynucleotide encoding an influenza virus packaging signal.

3. The polynucleotide of claim 1, wherein the polynucleotide is DNA or single-stranded negative RNA.

4. A plasmid comprising the polynucleotide of claim 3.

5. A plasmid composition comprising the plasmid of claim 4 and plasmids encoding influenza virus segments 1, 2, 3, 5, 6, 7, and 8.

6. An engineered influenza virus comprising (a) the engineered influenza virus segment 4 polynucleotide of claim 1 and (b) an engineered influenza virus segment 6 polynucleotide encoding a second HA polypeptide, wherein the engineered influenza virus is replication-competent.

7. An engineered influenza virus comprising the engineered virus segment 4 of claim 1, comprising the first polynucleotide encoding a first hemagglutinin (HA) polypeptide and a second polynucleotide encoding a second HA polypeptide, wherein the virus comprises eight segments, an unmodified PB1 protein, and is replication-competent.

8. The engineered influenza virus of claim 6, wherein the first HA polypeptide and the second HA polypeptide each comprise an HA subtype 1 (HA1) polypeptide or an HA subtype 3 (HA3) polypeptide.

9. The engineered influenza virus of claim 6, wherein the first HA polypeptide comprises an HA subtype 1 (HA1) polypeptide and the second HA polypeptide comprises an HA subtype 3 (HA3) polypeptide.

10. The engineered influenza virus of claim 6, wherein the virus comprises unmodified viral proteins PB2, PB1, PA, NP, NA, M, and NS, and the first and second HA polypeptides are unmodified.

11. An engineered influenza virus comprising engineered influenza virus segment 4 polynucleotide of claim 1, wherein the virus comprises eight segments, unmodified viral proteins PB2, PB1, PA, HA, NP, NA, M, and NS, and is replication-competent.

12. A method for preventing or reducing the symptoms of influenza in a subject comprising administering a therapeutically effective amount of the engineered influenza virus of claim 6 to the subject to prevent or reduce the symptoms of influenza in the subject.

13. A method for producing an influenza virus comprising introducing the engineered influenza virus of claim 6 into a cell.

14. A method for detecting the presence of a rescued influenza virus in a cell in a culture comprising introducing the plasmid composition of claim 5 into the cell.

15. An engineered influenza virus comprising (a) the engineered influenza virus segment 4 polynucleotide of claim 1, wherein the engineered influenza virus is replication-competent.

* * * * *

SEQUENCE LISTING

```
<160> NUMBER OF SEQ ID NOS: 55

<210> SEQ ID NO 1
<211> LENGTH: 99
<212> TYPE: DNA
<213> ORGANISM: Influenza virus
<220> FEATURE:
<221> NAME/KEY: misc_feature
```

```
<222> LOCATION: (1)..(99)
<223> OTHER INFORMATION: Segment 4 Packaging signal, 5' portion

<400> SEQUENCE: 1
agcaaaagca ggggaaaata aaaacaacca aattgaaggc aaacctactg gtcctgttaa    60
gtgcacttgc agctgcagtt gcagacacaa tttgtatag                           99

<210> SEQ ID NO 2
<211> LENGTH: 150
<212> TYPE: DNA
<213> ORGANISM: Influenza virus
<220> FEATURE:
<221> NAME/KEY: misc_feature
<222> LOCATION: (1)..(150)
<223> OTHER INFORMATION: Segment 4 Packaging signal, 3' portion

<400> SEQUENCE: 2
atctactcaa ctgtcgccag ttcactggtg cttttggtct ccctgggggc aatcagtttc    60
tggatgtgtt ctaatggatc tttgcagtgc agaatatgca tctgagatta gaatttcaga  120
aatatgagga aaaacaccct tgtttctact                                    150

<210> SEQ ID NO 3
<211> LENGTH: 4
<212> TYPE: PRT
<213> ORGANISM: Homo sapiens
<220> FEATURE:
<221> NAME/KEY: misc_feature
<222> LOCATION: (1)..(4)
<223> OTHER INFORMATION: Furin Site

<400> SEQUENCE: 3

Arg Lys Arg Arg
1

<210> SEQ ID NO 4
<211> LENGTH: 22
<212> TYPE: PRT
<213> ORGANISM: Porcine teschovirus 2A
<220> FEATURE:
<221> NAME/KEY: misc_feature
<222> LOCATION: (1)..(22)
<223> OTHER INFORMATION: PTV1-2A motif

<400> SEQUENCE: 4

Gly Ser Gly Ala Thr Asn Phe Ser Leu Leu Lys Gly Ala Gly Asp Val
1               5                  10                  15

Glu Glu Asn Pro Gly Pro
            20

<210> SEQ ID NO 5
<211> LENGTH: 17
<212> TYPE: PRT
<213> ORGANISM: Influenza virus
<220> FEATURE:
<221> NAME/KEY: misc_feature
<222> LOCATION: (1)..(17)
<223> OTHER INFORMATION: HA signal polypeptide sequence
      (hemagglutinin = HA from Influenza virus); Not altered from
      native sequence (and variable for different HA proteins); for
      PR8 in our Seg4 HA/NA construct

<400> SEQUENCE: 5

Met Lys Ala Asn Leu Leu Val Leu Leu Ser Ala Leu Ala Ala Ala Asp
1               5                  10                  15

Ala
```

<210> SEQ ID NO 6
<211> LENGTH: 29
<212> TYPE: DNA
<213> ORGANISM: Artificial Sequence
<220> FEATURE:
<223> OTHER INFORMATION: Synthetic: mRub2-2A-HA Fragment 1, Forward
      primer

<400> SEQUENCE: 6
ctccgaagtt ggggggagc aaaagcagg                                29

<210> SEQ ID NO 7
<211> LENGTH: 25
<212> TYPE: DNA
<213> ORGANISM: Artificial Sequence
<220> FEATURE:
<223> OTHER INFORMATION: Synthetic: mRub2-2A-HA Fragment 1, Reverse
      primer

<400> SEQUENCE: 7
ttatagagtt catccattcc tcctc                                   25

<210> SEQ ID NO 8
<211> LENGTH: 44
<212> TYPE: DNA
<213> ORGANISM: Artificial Sequence
<220> FEATURE:
<223> OTHER INFORMATION: Synthetic: mRub2-2A-HA Fragment 2, Forward
      primer

<400> SEQUENCE: 8
atggatgaac tctataagg atctggggct accaacttca gtct               44

<210> SEQ ID NO 9
<211> LENGTH: 30
<212> TYPE: DNA
<213> ORGANISM: Artificial Sequence
<220> FEATURE:
<223> OTHER INFORMATION: Synthetic: mRub2-2A-HA Fragment 2, Reverse
      primer

<400> SEQUENCE: 9
tgggccgccg ggttattagt agaaacaagg                              30

<210> SEQ ID NO 10
<211> LENGTH: 29
<212> TYPE: DNA
<213> ORGANISM: Artificial Sequence
<220> FEATURE:
<223> OTHER INFORMATION: Synthetic: mNeon-2A-HA Fragment 1, Forward
      primer

<400> SEQUENCE: 10
ctccgaagtt ggggggagc aaaagcagg                                29

<210> SEQ ID NO 11
<211> LENGTH: 23
<212> TYPE: DNA
<213> ORGANISM: Artificial Sequence
<220> FEATURE:
<223> OTHER INFORMATION: Synthetic: mNeon-2A-HA Fragment 1, Reverse
      primer

<400> SEQUENCE: 11
atattgtgtc tgccgcggcc gcc                                     23

<210> SEQ ID NO 12
<211> LENGTH: 44
<212> TYPE: DNA
<213> ORGANISM: Artificial Sequence
<220> FEATURE:
<223> OTHER INFORMATION: Synthetic: mNeon-2A-HA Fragment 2, Forward primer

<400> SEQUENCE: 12
cggacgcaga cacaatatgt ataggctacc atgcgaacaa ttca                44

<210> SEQ ID NO 13
<211> LENGTH: 30
<212> TYPE: DNA
<213> ORGANISM: Artificial Sequence
<220> FEATURE:
<223> OTHER INFORMATION: Synthetic: mNeon-2A-HA Fragment 2, Reverse primer

<400> SEQUENCE: 13
tgggccgccg ggttattagt agaaacaagg                                30

<210> SEQ ID NO 14
<211> LENGTH: 29
<212> TYPE: DNA
<213> ORGANISM: Artificial Sequence
<220> FEATURE:
<223> OTHER INFORMATION: Synthetic: NA-Furin-2A-mNeon Fragment 1, Forward primer

<400> SEQUENCE: 14
ctccgaagtt gggggggagc gaaagcagg                                 29

<210> SEQ ID NO 15
<211> LENGTH: 41
<212> TYPE: DNA
<213> ORGANISM: Artificial Sequence
<220> FEATURE:
<223> OTHER INFORMATION: Synthetic: NA-Furin-2A-mNeon Fragment 1, Reverse primer

<400> SEQUENCE: 15
ctccagtcta cggtgtcact attcacgcca aaagaaatgc t                   41

<210> SEQ ID NO 16
<211> LENGTH: 26
<212> TYPE: DNA
<213> ORGANISM: Artificial Sequence
<220> FEATURE:
<223> OTHER INFORMATION: Synthetic: NA-Furin-2A-mNeon Fragment 2, Forward primer

<400> SEQUENCE: 16
tgacaccgta gactggagct ggccgg                                    26

<210> SEQ ID NO 17
<211> LENGTH: 30
<212> TYPE: DNA
<213> ORGANISM: Artificial Sequence
<220> FEATURE:
<223> OTHER INFORMATION: Synthetic: NA-Furin-2A-mNeon Fragment 2, Reverse primer

<400> SEQUENCE: 17
tgggccgccg ggttattagt agaaacaagg                                30

<210> SEQ ID NO 18
<211> LENGTH: 29
<212> TYPE: DNA
<213> ORGANISM: Artificial Sequence
<220> FEATURE:
<223> OTHER INFORMATION: Synthetic: S4 H1N1 NA/HA Fragment 1, Forward
      primer

<400> SEQUENCE: 18
ctccgaagtt gggggggagc aaaagcagg                                           29

<210> SEQ ID NO 19
<211> LENGTH: 26
<212> TYPE: DNA
<213> ORGANISM: Artificial Sequence
<220> FEATURE:
<223> OTHER INFORMATION: Synthetic: S4 H1N1 NA/HA Fragment 1, Reverse
      primer

<400> SEQUENCE: 19
cctgcattcc aagtgagaac atgaaa                                              26

<210> SEQ ID NO 20
<211> LENGTH: 44
<212> TYPE: DNA
<213> ORGANISM: Artificial Sequence
<220> FEATURE:
<223> OTHER INFORMATION: Synthetic: S4 H1N1 NA/HA Fragment 2, Forward
      primer

<400> SEQUENCE: 20
tctcacttgg aatgcaggac cttttttctg acccaaggtg cctt                          44

<210> SEQ ID NO 21
<211> LENGTH: 44
<212> TYPE: DNA
<213> ORGANISM: Artificial Sequence
<220> FEATURE:
<223> OTHER INFORMATION: Synthetic: S4 H1N1 NA/HA Fragment 2, Reverse
      primer

<400> SEQUENCE: 21
gttggtagcc ccagatgggg ttctctttct tttatcgata gaaa                          44

<210> SEQ ID NO 22
<211> LENGTH: 26
<212> TYPE: DNA
<213> ORGANISM: Artificial Sequence
<220> FEATURE:
<223> OTHER INFORMATION: Synthetic: S4 H1N1 NA/HA Fragment 3, Forward
      primer

<400> SEQUENCE: 22
ggatctgggg ctaccaactt cagtct                                              26

<210> SEQ ID NO 23
<211> LENGTH: 30
<212> TYPE: DNA
<213> ORGANISM: Artificial Sequence
<220> FEATURE:
<223> OTHER INFORMATION: Synthetic: S4 H1N1 NA/HA Fragment 3, Reverse
      primer

<400> SEQUENCE: 23
tgggccgccg ggttattagt agaaacaagg                                          30

<210> SEQ ID NO 24

-continued

```
<211> LENGTH: 29
<212> TYPE: DNA
<213> ORGANISM: Artificial Sequence
<220> FEATURE:
<223> OTHER INFORMATION: Synthetic: NA-Flag-Furin-2A-mNeon Fragment 1,
      Forward primer

<400> SEQUENCE: 24
ctccgaagtt gggggggagc gaaagcagg                                          29

<210> SEQ ID NO 25
<211> LENGTH: 47
<212> TYPE: DNA
<213> ORGANISM: Artificial Sequence
<220> FEATURE:
<223> OTHER INFORMATION: Synthetic: NA-Flag-Furin-2A-mNeon Fragment 1,
      Reverse primer

<400> SEQUENCE: 25
gtcatcgtca tctttataat ctacccaggt gctattttta taggtaa                      47

<210> SEQ ID NO 26
<211> LENGTH: 44
<212> TYPE: DNA
<213> ORGANISM: Artificial Sequence
<220> FEATURE:
<223> OTHER INFORMATION: Synthetic: NA-Flag-Furin-2A-mNeon Fragment 1,
      Forward primer

<400> SEQUENCE: 26
tataaagatg atgatgacaa ggacacaact tcagtgatat taac                         44

<210> SEQ ID NO 27
<211> LENGTH: 30
<212> TYPE: DNA
<213> ORGANISM: Artificial Sequence
<220> FEATURE:
<223> OTHER INFORMATION: Synthetic: NA-Flag-Furin-2A-mNeon Fragment 1,
      Reverse primer

<400> SEQUENCE: 27
tgggccgccg ggttattagt agaaacaagg                                         30

<210> SEQ ID NO 28
<211> LENGTH: 29
<212> TYPE: DNA
<213> ORGANISM: Artificial Sequence
<220> FEATURE:
<223> OTHER INFORMATION: Synthetic: ZsGreen Seg 6, Forward primer

<400> SEQUENCE: 28
ctccgaagtt gggggggagc gaaagcagg                                          29

<210> SEQ ID NO 29
<211> LENGTH: 30
<212> TYPE: DNA
<213> ORGANISM: Artificial Sequence
<220> FEATURE:
<223> OTHER INFORMATION: Synthetic: ZsGreen Seg 6, Reverse primer

<400> SEQUENCE: 29
tgggccgccg ggttattagt agaaacaagg                                         30

<210> SEQ ID NO 30
<211> LENGTH: 29
<212> TYPE: DNA
<213> ORGANISM: Artificial Sequence
```

```
<220> FEATURE:
<223> OTHER INFORMATION: Synthetic: HK 68 HA Seg 6, Forward primer

<400> SEQUENCE: 30
ctccgaagtt gggggggagc gaaagcagg                                       29

<210> SEQ ID NO 31
<211> LENGTH: 30
<212> TYPE: DNA
<213> ORGANISM: Artificial Sequence
<220> FEATURE:
<223> OTHER INFORMATION: Synthetic: HK 68 HA Seg 6, Reverse primer

<400> SEQUENCE: 31
tgggccgccg ggttattagt agaaacaagg                                      30

<210> SEQ ID NO 32
<211> LENGTH: 29
<212> TYPE: DNA
<213> ORGANISM: Artificial Sequence
<220> FEATURE:
<223> OTHER INFORMATION: Synthetic: PR8 HA Seg 6, Forward primer

<400> SEQUENCE: 32
ctccgaagtt gggggggagc gaaagcagg                                       29

<210> SEQ ID NO 33
<211> LENGTH: 30
<212> TYPE: DNA
<213> ORGANISM: Artificial Sequence
<220> FEATURE:
<223> OTHER INFORMATION: Synthetic: PR8 HA Seg 6, Reverse primer

<400> SEQUENCE: 33
tgggccgccg ggttattagt agaaacaagg                                      30

<210> SEQ ID NO 34
<211> LENGTH: 56
<212> TYPE: DNA
<213> ORGANISM: Artificial Sequence
<220> FEATURE:
<223> OTHER INFORMATION: Synthetic: Yamagata 88 HA Seg 6, Forward primer

<400> SEQUENCE: 34
actggaattt gcaaccaaga tatcgccacc atgaaggcaa taattgtact actcat         56

<210> SEQ ID NO 35
<211> LENGTH: 52
<212> TYPE: DNA
<213> ORGANISM: Artificial Sequence
<220> FEATURE:
<223> OTHER INFORMATION: Synthetic: Yamagata 88 HA Seg 6, Reverse primer

<400> SEQUENCE: 35
tctagccctg ttagctcagt ttaaacttat agacagatgg agcaagaaac at             52

<210> SEQ ID NO 36
<211> LENGTH: 56
<212> TYPE: DNA
<213> ORGANISM: Artificial Sequence
<220> FEATURE:
<223> OTHER INFORMATION: Synthetic: Malaysia 04 HA Seg 6, Forward primer

<400> SEQUENCE: 36
actggaattt gcaaccaaga tatcgccacc atgaaggcaa taattgtact actcat         56
```

<210> SEQ ID NO 37
<211> LENGTH: 52
<212> TYPE: DNA
<213> ORGANISM: Artificial Sequence
<220> FEATURE:
<223> OTHER INFORMATION: Synthetic: Malaysia 04 HA Seg 6, Reverse primer

<400> SEQUENCE: 37
tctagccctg ttagctcagt ttaaacttat agacagatgg agcaagaaac at         52

<210> SEQ ID NO 38
<211> LENGTH: 55
<212> TYPE: DNA
<213> ORGANISM: Artificial Sequence
<220> FEATURE:
<223> OTHER INFORMATION: Synthetic: Fujian 2002 HA Seg 6, Forward primer

<400> SEQUENCE: 38
actggaattt gcaaccaaga tatcgccacc atgaagacca tcatagcact gtcat       55

<210> SEQ ID NO 39
<211> LENGTH: 55
<212> TYPE: DNA
<213> ORGANISM: Artificial Sequence
<220> FEATURE:
<223> OTHER INFORMATION: Synthetic: Fujian 2002 HA Seg 6, Reverse primer

<400> SEQUENCE: 39
acagtctagc cctgttagct cagtttaaac tcagatgcaa atattacacc gtata 55

<210> SEQ ID NO 40
<211> LENGTH: 49
<212> TYPE: DNA
<213> ORGANISM: Artificial Sequence
<220> FEATURE:
<223> OTHER INFORMATION: Synthetic: Victoria 2009 HA Seg 6, Forward primer

<400> SEQUENCE: 40
actggaattt gcaaccaaga tatcgccacc atgaaaacaa ttatcgctc 49

<210> SEQ ID NO 41
<211> LENGTH: 49
<212> TYPE: DNA
<213> ORGANISM: Artificial Sequence
<220> FEATURE:
<223> OTHER INFORMATION: Synthetic: Victoria 2009 HA Seg 6, Reverse primer

<400> SEQUENCE: 41
acagtctagc cctgttagct cagtttaaac tcaaatacag atgttgcat 49

<210> SEQ ID NO 42
<211> LENGTH: 173
<212> TYPE: DNA
<213> ORGANISM: Influenza virus
<220> FEATURE:
<221> NAME/KEY: misc_feature
<222> LOCATION: (1)..(173)
<223> OTHER INFORMATION: Segment 6 Packaging signal, 5' portion

<400> SEQUENCE: 42
agcgaaagca ggggtttaaa ttgaatccaa atcagaaaat aacaaccatt ggatcaatct 60
gtctggtagt cggactaatt agcctaatat tgcaaatagg gaatataatc tcaatttgga 120
ttagccattc aattcaaact ggaagtcaaa accatactgg aatttgcaac caa 173

<210> SEQ ID NO 43
<211> LENGTH: 209
<212> TYPE: DNA
<213> ORGANISM: Influenza virus
<220> FEATURE:
<221> NAME/KEY: misc_feature
<222> LOCATION: (1)..(209)
<223> OTHER INFORMATION: Segment 6 Packaging signal, 3' portion

<400> SEQUENCE: 43

```
tgagctaaca gggctagact gtatgaggcc gtgcttctgg gttgaattaa tcaggggacg    60
acctaaagaa aaacaatct ggactagtgc gagcagcatt tcttttttgtg gcgtgaatag   120
tgatactgta gattggtctt ggccagacgg tgctgagttg ccattcagca ttgacaagta   180
gtctgttcaa aaaactcctt gtttctact                                     209
```

<210> SEQ ID NO 44
<211> LENGTH: 2364
<212> TYPE: DNA
<213> ORGANISM: Artificial Sequence
<220> FEATURE:
<223> OTHER INFORMATION: Synthetic: NA-Furin-2A-mNeon Sequence in
      Segment 6

<400> SEQUENCE: 44

```
agcgaaagca ggggtttaaa atgaatccaa atcagaaaat aacaaccatt ggatcaatct     60
gtctggtagt cggactaatt agcctaatat tgcaaatagg gaatataatc tcaatatgga   120
ttagccattc aattcaaact ggaagtcaaa accatactgg aatatgcaac caaaacatca   180
ttacctataa aaatagcacc tgggtaaagg acacaacttc agtgatatta accggcaatt   240
catctctttg tcccatccgt gggtgggcta tatacagcaa agacaatagc ataagaattg   300
gttccaaagg agacgttttt gtcataagag agccctttat ttcatgttct cacttggaat   360
gcaggacctt ttttctgacc caaggtgcct tactgaatga caagcattca aatgggactg   420
ttaaggacag aagcccttat agggccttaa tgagctgccc tgtcggtgaa gctccgtccc   480
cgtacaattc aagatttgaa tcggttgctt ggtcagcaag tgcatgtcat gatggcatgg   540
gctggctaac aatcggaatt tcaggtccag ataatggagc agtggctgta ttaaaataca   600
acggcataat aactgaaacc ataaaaagt ggaggaagaa atattgagg acacaagagt   660
ctgaatgtgc ctgtgtaaat ggttcatgtt ttactataat gactgatggc ccgagtgatg   720
ggctggcctc gtacaaaatt tccaagatcg aaaaggggaa ggttactaaa tcaatagagt   780
tgaatgcacc taattctcac tatgaggaat gttcctgtta ccctgatacc ggcaaagtga   840
tgtgtgtgtg cagagacaac tggcatggtt cgaaccggcc atgggtgtct ttcgatcaaa   900
acctggatta tcaaatagga tacatctgca gtgggggttt cggtgacaac ccgcgtcccg   960
aagatggaac aggcagctgt ggtccagtgt atgttgatgg agcaaacgga gtaaagggat  1020
tttcatatag gtatggtaat ggtgtttgga taggaaggac caaaagtcac agttccagac  1080
atgggtttga gatgatttgg gatcctaatg gatggacaga gactgatagt aagttctctg  1140
ttaggcaaga tgttgtggca atgactgatt ggtcagggta tagcggaagt ttcgttcaac  1200
atcctgagct aacagggcta gactgtatga ggccgtgctt ctgggttgaa ttaatcaggg  1260
gacgaccta agaaaaaaca atctggacta gtgcgagcag catttctttt tgtggcgtga  1320
atagtgacac cgtagactgg agctggccgg atggcgccga actaccgttt tctatcgata  1380
aaagaaagag aaggggaagc ggagcaacaa atttcagcct tcttaaacaa gcaggagatg  1440
```

-continued

```
tggaagaaaa tccaggacca atggtcagca aggagagga ggacaacatg gctagcctac    1500
ctgccactca tgagcttcat atattcggtt ctattaacgg agtagatttc gatatggtcg    1560
gacaagggac gggcaatcca aatgatggat atgaggagct taatctaaag tcaacaaaag    1620
gagacctcca attttctccc tggatcttgg tcccacacat tggatacgga tttcatcaat    1680
acctacctta ccctgatgga atgtcaccgt ttcaagcagc aatggtggac gggagtggat    1740
accaagttca tagaacaatg cagtttgagg atggtgcctc cctaaccgtc aattataggt    1800
atacctacga gggctcccat attaagggcg aagcacaagt gaaaggaaca gggttcccag    1860
cagacgggcc tgtgatgacc aattcgctaa cggcagctga ctggtgcagg agtaaaagga    1920
cgtatccaaa tgacaaaaca attatttcca ctttcaagtg gagttacaca actggtaatg    1980
ggaagagata taggtctaca gcaaggacta catacacttt cgcaaagcca atggctgcaa    2040
actatctcaa gaatcaacca atgtatgtat tcagaaaaac agagcttaaa cattctaaaa    2100
ccgagttaaa ttttaaggaa tggcaaaagg catttacgga tgtgatggga atggatgaac    2160
tgtataaaaa agacgaactg tagccgtgct tctgggttga attaatcagg ggacgaccta    2220
aagaaaaaac aatctggact agtgcgagca gcatttcttt ttgtggcgtg aatagtgata    2280
ctgtagattg gtcttggcca gacggtgctg agttgccatt cagcattgac aagtagtctg    2340
ttcaaaaaac tccttgtttc tact                                          2364
```

<210> SEQ ID NO 45
<211> LENGTH: 2625
<212> TYPE: DNA
<213> ORGANISM: Artificial Sequence
<220> FEATURE:
<223> OTHER INFORMATION: Synthetic: mRuby2-2A-HA In Segment 4

<400> SEQUENCE: 45

```
agcaaaagca ggggaaaata aaaacaacca aattgaaggc aaacctactg gtcctgttaa      60
gtgcacttgc agctgcagtt gcagacacaa tttgtatagg ccaccatggt atccaagggc     120
gaggaactta ttaaagaaaa tatgcgcatg aaagtggtca tggaggggtc tgttaatggt     180
catcagttta atgcacagg cgaagggaa ggaaacccct atatgggaac acaaacaatg     240
agaataaaag tgattgaagg gggcccactg ccccttcgcat tcgacatcct tgcgacatcc     300
tttatgtatg gatcgaggac atttattaaa tacccgaaag gaataccaga cttcttcaaa     360 cagtctcttcc ccgagggatt cacctgggag agagtaacta gatacgagga tgggggtgtg     420
gtcacagtga tgcaagacac tagcctcgaa gatggctgtc tggtatatca tgtccaagtg     480 agggggggtca atttccctc taatggtcct gtgatgcaga agaaaactaa aggatgggaa     540
cccaatactg aaatgatgta ccccgctgat ggaggtttaa ggggctacac tcatatggct     600
cttaaagtag atggaggagg acacctgtca tgctccttcg tcacaacata tagatctaaa     660 aaacagttg aaatatcaa atgccaggg atccatgccg ttgatcacag gctagaaaga     720
ttggaagaga gcgacaacga atgtttgta gtgcagcggg aacatgccgt agccaagttt     780
gctggattgg gaggaggaat ggatgaactc tataaaggat ctgggcgtac caacttcagt     840
ctcctcaaac aggccggaga cgtggaagaa atcctgggc ctatgaaagc gaatttgtta     900
gttttactgt ccgcgttggc ggccgcggac gcagacacaa tatgtatagg ctaccatgcg     960
aacaattcaa ccgacactgt tgacacagta ctcgagaaga atgtgacagt gacacactct    1020
gttaacctgc tcgaagacag ccacaacgga aaactatgta gattaaaagg aatagcccca    1080
```

```
ctacaattgg ggaaatgtaa catcgccgga tggctcttgg gaaacccaga atgcgaccca      1140
ctgcttccag tgagatcatg gtcctacatt gtagaaacac caaactctga gaatggaata     1200
tgttatccag gagatttcat cgactatgag gagctgaggg agcaattgag ctcagtgtca     1260
tcattcgaaa gattcgaaat atttcccaaa gaaagctcat ggcccaacca caacacaaac     1320
ggagtaacgg cagcatgctc ccatgagggg aaaagcagtt tttacagaaa tttgctatgg     1380
ctgacgagaa aggagggctc atacccaaag ctgaaaaatt cttatgtgaa caaaaagggg     1440
aaagaagtcc ttgtactgtg gggtattcat cacccgccta acagtaagga caacagaat     1500 ctctatcaga tgaaaatgc ttatgtctct gtagtgactt caaattataa caggagattt     1560
accccggaaa tagcagaaag acccaaagta agagatcaag ctgggaggat gaactattac     1620
tggaccttgc taaacccgg agacacaata tatttgagg caaatggaaa tctaatagca     1680
ccaatgtatg ctttcgcact gagtagaggc tttgggtccg gcatcatcac ctcaaacgca     1740
tcaatgcatg agtgtaacac gaagtgtcaa acaccctgg gagctataaa cagcagtctc     1800
ccttaccaga atatacaccc agtcacaata ggagagtgcc caaaatacgt caggagtgcc     1860
aaattgagga tggttacagg actaaggaac actccgtcca ttcaatccag aggtctattt     1920
ggagccattg ccggttttat tgaaggggga tggactggaa tgatagatgg atggtatggt     1980
tatcatcatc agaatgaaca gggatcaggc tatgcagcgg atcaaaaaag cacacaaaat     2040
gccattaacg gattacaaa caaggtgaac actgttatcg agaaaatgaa cattcaattc     2100
acagctgtgg gtaaagaatt caacaaatta gaaaaaagga tggaaaattt aaataaaaaa     2160
gttgatgatg gatttctgga catttggaca tataatgcag aattgttagt tctactggaa     2220
aatgaaagga ctctggattt ccatgactca aatgtgaaga tctgtatga gaaagtaaaa     2280 agccaattaa agaataatgc caagaaaatc ggaaatggat gttttgagtt ctaccacaag     2340
tgtgacaatg aatgcatgga aagtgtaaga aatgggactt atgattatcc caaatattca     2400
gaagagtcaa agttgaacag ggaaaaggta gatggagtga aattggaatc aatgggatc     2460 tatcagattc tggcgatcta ctcaactgtc gccagttcac tggtgctttt ggtctccctg     2520
ggggcaatca gtttctggat gtgttctaat ggatctttgc agtgcagaat atgcatctga     2580
gattagaatt tcagaaatat gaggaaaaac accctgtttt ctact                    2625
```

<210> SEQ ID NO 46
<211> LENGTH: 3288
<212> TYPE: DNA
<213> ORGANISM: Artificial Sequence
<220> FEATURE:
<223> OTHER INFORMATION: Synthetic: NA-Furin-2A-HA in Segment 4

<400> SEQUENCE: 46

```
agcaaaagca ggggaaaata aaaacaacca aattgaaggc aaacctactg gtcctgttaa      60
gtgcacttgc agctgcagtt gcagacacaa tttgtatagg ccaccatgaa cccgaaccaa     120
aagatcacga ctatcgggag catttgctta gtggttgggt tgatcagcct aatattgcaa     180
atagggaata taatctcaat atggattagc cattcaattc aaactggaag tcaaaaccat     240
actggaatat gcaaccaaaa catcattacc tataaaaata gcacctgggt aaaggacaca     300
acttcagtga tattaaccgg caattcatct ctttgtccca tccgtgggtg gctatatac     360 agcaaagaca atagcataag aattggttcc aaaggagacg ttttttgtcat aagagagccc     420 tttatttcat gttctcactt ggaatgcagg acctttttc tgacccaagg tgccttactg     480
aatgacaagc attcaaatgg gactgttaag gacagaagcc cttataggc cttaatgagc     540
```

```
tgccctgtcg gtgaagctcc gtccccgtac aattcaagat ttgaatcggt tgcttggtca    600
gcaagtgcat gtcatgatgg catgggctgg ctaacaatcg gaatttcagg tccagataat    660
ggagcagtgg ctgtattaaa atacaacggc ataataactg aaaccataaa aagttggagg    720
aagaaaatat tgaggacaca agagtctgaa tgtgcctgtg taaatggttc atgttttact    780
ataatgactg atggcccgag tgatgggctg gcctcgtaca aaattttcaa gatcgaaaag    840
gggaaggtta ctaaatcaat agagttgaat gcacctaatt ctcactatga ggaatgttcc    900
tgttaccctg ataccggcaa agtgatgtgt gtgtgcagag acaactggca tggttcgaac    960
cggccatggg tgtctttcga tcaaaacctg gattatcaaa taggatacat ctgcagtggg   1020
gttttcggtg acaacccgcg tcccgaagat ggaacaggca gctgtggtcc agtgtatgtt   1080
gatggagcaa acggagtaaa gggattttca tataggtatg gtaatggtgt ttggatagga   1140
aggaccaaaa gtcacagttc cagacatggg tttgagatga tttgggatcc taatggatgg   1200
acagagacta atagtaagtt ctctgttagg caagatgttg tggcaatgac tgattggtca   1260
gggtatagcg gaagtttcgt tcaacatcct gagctaacag ggctagactg tatgaggccg   1320
tgcttctggg ttgaattaat caggggacga cctaaagaaa aaacaatctg gactagtgcg   1380
agcagcattt cttttttgtgg cgtgaatagt gacaccgtag actggagctg gccggatggc   1440
gccgaactac cgttttctat cgataaaaga aagagaaggg gatctggggc taccaacttc   1500
agtctcctca aacaggccgg agacgtggaa gaaaatcctg ggcctatgaa agcgaatttg   1560
ttagttttac tgtccgcgtt ggcggccgcg gacgcagaca caatatgtat aggctaccat   1620
gcgaacaatt caaccgacac tgttgacaca gtactcgaga agaatgtgac agtgacacac   1680
tctgttaacc tgctcgaaga cagccacaac ggaaaactat gtagattaaa aggaatagcc   1740
ccactacaat tggggaaatg taacatcgcc ggatggctct tgggaaaccc agaatgcgac   1800
ccactgcttc cagtgagatc atggtcctac attgtagaaa caccaaactc tgagaatgga   1860
atatgttatc caggagattt catcgactat gaggagctga gggagcaatt gagctcagtg   1920
tcatcattcg aaagattcga aatatttccc aaagaaagct catggcccaa ccacaacaca   1980
aacggagtaa cggcagcatg ctcccatgag ggaaaagca gttttacag aaatttgcta   2040 tggctgacgg agaaggaggg ctcataccca aagctgaaaa attcttatgt gaacaaaaaa   2100
gggaaagaag tccttgtact gtggggtatt catcacccgc ctaacagtaa ggaacaacag   2160
aatctctatc agaatgaaaa tgcttatgtc tctgtagtga cttcaaatta taacaggaga   2220 tttacccegg aaatagcaga aagacccaaa gtaagagatc aagctgggag gatgaactat   2280
tactggacct tgctaaaacc cggagacaca ataatatttg aggcaaatgg aaatctaata   2340
gcaccaatgt atgctttcgc actgagtaga ggctttgggt ccggcatcat cacctcaaac   2400
gcatcaatgc atgagtgtaa cacgaagtgt caaacacccc tgggagctat aaacagcagt   2460
ctcccttacc agaatataca cccagtcaca ataggagagt gcccaaaata cgtcaggagt   2520
gccaaattga ggatggttac aggactaagg aacactccgt ccattcaatc cagaggtcta   2580
tttggagcca ttgccggttt tattgaaggg ggatggactg gaatgataga tggatggtat   2640
ggttatcatc atcagaatga acagggatca ggctatgcag cggatcaaaa aagcacacaa   2700
aatgccatta acgggattac aaacaaggtg aacactgtta tcgagaaaat gaacattcaa   2760
ttcacagctg tgggtaaaga attcaacaaa ttagaaaaaa ggatgaaaaa tttaaataaa   2820
aaagttgatg atggatttct ggacatttgg acatataatg cagaattgtt agttctactg   2880
```

| | |
|---|---|
| gaaaatgaaa ggactctgga tttccatgac tcaaatgtga agaatctgta tgagaaagta | 2940 |
| aaaagccaat taaagaataa tgccaaagaa atcggaaatg gatgttttga gttctaccac | 3000 |
| aagtgtgaca atgaatgcat ggaaagtgta agaaatggga cttatgatta tcccaaatat | 3060 |
| tcagaagagt caaagttgaa cagggaaaag gtagatggag tgaaattgga atcaatgggg | 3120 |
| atctatcaga ttctggcgat ctactcaact gtcgccagtt cactggtgct tttggtctcc | 3180 |
| ctggggggcaa tcagtttctg gatgtgttct aatggatctt tgcagtgcag aatatgcatc | 3240 |
| tgagattaga atttcagaaa tatgaggaaa acacccttg tttctact | 3288 |

<210> SEQ ID NO 47
<211> LENGTH: 1098
<212> TYPE: DNA
<213> ORGANISM: Artificial Sequence
<220> FEATURE:
<223> OTHER INFORMATION: Synthetic: ZsGreen in Segment 6

<400> SEQUENCE: 47

| | |
|---|---|
| agcgaaagca ggggtttaaa ttgaatccaa atcagaaaat aacaaccatt ggatcaatct | 60 |
| gtctggtagt cggactaatt agcctaatat tgcaaatagg gaatataatc tcaatttgga | 120 |
| ttagccattc aattcaaact ggaagtcaaa accatactgg aatttgcaac caagatatcg | 180 |
| ccaccatggc acagagcaaa catggactca ccaaggaaat gacaatgaag tatagaatgg | 240 |
| agggatgcgt cgacggtcat aaattcgtaa tcactgggga aggaatcggt tacccgttca | 300 |
| aaggaaaaca ggccattaac ctgtgtgtcg tcgagggggg tcctcttcct ttcgcagagg | 360 |
| atattctaag cgcagccttt atgtatgaaa tagggtgtt taccgaatat cctcaagaca | 420 |
| tcgtagatta tttcaaaaac agttgccccg ccgggtacac ttgggataga tcttttctgt | 480 |
| tcgaggacag agcagtgtgc atatgtaacg cagacattac agtgagcgtt gaagagaact | 540 |
| gcatgtatca cgaatctaaa ttctatggcg taaacttccc tgccgatggc ccggttatga | 600 |
| agaagatgac tgacaactgg gagccctcgt gcgaaaagat aattccagtt cctaaacaag | 660 |
| gcattttgaa gggagacgtc tcaatgtatc tacttcttaa ggatggcgga agattgcgat | 720 |
| gccagttcga tacagtatat aaagcaaaga gcgtgcctcg aaagatgcca gattggcatt | 780 |
| tcatccagca taaactgacc cgagaagatc ggtctgatgc aaagaaccaa aaatggcacc | 840 |
| tgactgagca tgccatagcc tctggttccg ccctcccatg agtttaaact gagctaacag | 900 |
| ggctagactg tatgaggccg tgcttctggg ttgaattaat caggggacga cctaaagaaa | 960 |
| aaacaatctg gactagtgcg agcagcattt ctttttgtgg cgtgaatagt gatactgtag | 1020 |
| attggtcttg gccagacggt gctgagttgc cattcagcat tgacaagtag tctgttcaaa | 1080 |
| aaactccttg tttctact | 1098 |

<210> SEQ ID NO 48
<211> LENGTH: 2103
<212> TYPE: DNA
<213> ORGANISM: Artificial Sequence
<220> FEATURE:
<223> OTHER INFORMATION: Synthetic: Hong Kong 68 HA in Segment 6

<400> SEQUENCE: 48

| | |
|---|---|
| agcgaaagca ggggtttaaa ttgaatccaa atcagaaaat aacaaccatt ggatcaatct | 60 |
| gtctggtagt cggactaatt agcctaatat tgcaaatagg gaatataatc tcaatttgga | 120 |
| ttagccattc aattcaaact ggaagtcaaa accatactgg aatttgcaac caagatatcg | 180 |
| ccaccatgaa acaataata gctcttagct acatcttctg cctagctctc gggcaggacc | 240 |

```
ttccaggaaa tgacaacagc acagcaacgc tgtgcctggg acatcatgcg gtgccaaacg      300
gaacactagt gaaaacaatc acagatgatc agattgaagt gactaatgct actgagctag      360
ttcagagctc ctcaacgggg aaaatatgca acaatcctca tcgaatcctt gatggaatag      420
actgcacact gatagatgct ctattggggg accctcattg tgatgttttt caaaatgaga      480
catgggacct tttcgttgaa cgcagcaaag ctttcagcaa ctgttaccct tatgatgtgc      540
cagattatgc ctcccttagg tcactagttg cctcgtcagg cactctggag tttatcactg      600
agggtttcac ttggactggg gtcactcaga atggggaag caatgcttgc aaaaggggac       660
ctggtagcgt ttttttcagt agactgaact ggttgaccaa atcaggaagc acatatccag      720
tgctgaacgt gactatgcca aacaatgaca attttgacaa actatacatt tgggggttc       780 accacccgag cacagaaccaa gaacaaacca gcctgtatgt tcaagcatca gggagagtca      840
cagtctctac caggagaagc cagcaaacta taatcccgaa tatcgagtcc agaccctggg      900 taagggtct gtctagtaga ataagcatct attggacaat agttaatccg ggagacgtac        960
tggtaattaa tagtaatggg aacctaatcg ctcctcgggg ttatttcaaa atgcgcactg      1020
ggaaaagctc aataatgagg tcagatgcac ctattgatac ctgtatttct gaatgcatca      1080
ctccaaatgg aagcattccc aatgacaagc cctttcaaaa cgtaaacaag atcacatatg      1140
gagcatgccc caagtatgtt aagcaaaaca ccctgaagtt ggcaacaggg atgcggaatg      1200
taccagagaa acaaactaga ggcctattcg gcgcaaaagc aggtttcata gaaaatggtt      1260
gggagggaat gatagacggt tggtacggtt tcaggcatca aaattctgag gcacaggac       1320 aagcagcaga tcttaaaagc actcaagcag ccatcgacca aatcaatggg aaattgaaca      1380
gggtaatcga aagacgaac gagaaattcc atcaaatcga aaaggaattc tcagaagtag       1440
aagggagaat tcaggacctc gagaaatacg ttgaagacac taaaatagat ctctggtctt      1500
acaatgcgga gcttcttgtc gctctggaga tcaacatac aattgacctg actgactcgg       1560
aaatgaacaa gctgtttgaa aaaacaagga ggcaactgag ggaaaatgct gaagacatgg      1620
gcaatggttg cttcaaaata taccacaaat gtgacaacgc ttgcatagag tcaatcagaa      1680
atgggactta tgaccatgat gtatacagag acgaagcatt aaacaaccgg tttcagatca      1740
aaggtgttga actgaagtct ggatacaaag actggatcct gtggatttcc tttgccattt      1800
cttgcttcct tctgtgcgtg gtcttgcttg gttttataat gtgggcttgt caaaggggaa      1860
acataagatg caacatatgt atatgagttt aaactgagct aacagggcta gactgtatga      1920
ggccgtgctt ctgggttgaa ttaatcaggg acgacctaa agaaaaaaca atctggacta       1980
gtgcgagcag catttctttt tgtggcgtga atagtgatac tgtagattgg tcttggccag      2040
acggtgctga gttgccattc agcattgaca agtagtctgt tcaaaaaact ccttgtttct      2100
act                                                                    2103
```

<210> SEQ ID NO 49
<211> LENGTH: 2100
<212> TYPE: DNA
<213> ORGANISM: Artificial Sequence
<220> FEATURE:
<223> OTHER INFORMATION: Synthetic: Puerto Rico 8 HA in Segment 6

<400> SEQUENCE: 49

```
agcgaaagca ggggtttaaa ttgaatccaa atcagaaaat aacaaccatt ggatcaatct       60
gtctggtagt cggactaatt agcctaatat tgcaaatagg gaatataatc tcaatttgga      120
```

```
ttagccattc aattcaaact ggaagtcaaa accatactgg aatttgcaac caagatatcg    180
ccaccatgaa agcgaatttg ttagttttac tgtccgcgtt ggcggccgcg gacgcagaca    240
caatatgtat aggctaccat gcgaacaatt caaccgacac tgttgacaca gtactcgaga    300
agaatgtgac agtgacacac tctgttaacc tgctcgaaga cagccacaac ggaaaactat    360
gtagattaaa aggaatagcc ccactacaat ggggaaatg taacatcgcc ggatggctct    420
tgggaaaccc agaatgcgac ccactgcttc cagtgagatc atggtcctac attgtagaaa    480
caccaaactc tgagaatgga atatgttatc caggagattt catcgactat gaggagctga    540
gggagcaatt gagctcagtg tcatcattcg aaagattcga atatttccc aaagaaagct    600
catggcccaa ccacaacaca acggagtaa cggcagcatg ctcccatgag ggaaaagca    660
gttttacag aaatttgcta tggctgacgg agaaggaggg ctcatacca agctgaaaa     720
attcttatgt gaacaaaaaa gggaaagaag tccttgtact gtggggtatt catcacccgc    780
ctaacagtaa ggaacaacag aatatctatc agaatgaaaa tgcttatgtc tctgtagtga    840
cttcaaatta taacaggaga tttaccccgg aaatagcaga aagacccaaa gtaagagatc    900
aagctgggag gatgaactat tactggacct tgctaaaacc cggagacaca ataatatttg    960
aggcaaatgg aaatctaata gcaccaatgt atgctttcgc actgagtaga ggctttgggt   1020
ccggcatcat cacctcaaac gcatcaatgc atgagtgtaa cacgaagtgt caaacacccc   1080
tgggagctat aaacagcagt ctcccttacc agaatataca cccagtcaca ataggagagt   1140
gcccaaaata cgtcaggagt gccaaattga ggatggttac aggactaagg aacactccgt   1200
ccattcaatc cagaggtcta tttggagcca ttgccggttt tattgaaggg ggatggactg   1260
gaatgataga tggatggtat ggttatcatc atcagaatga acagggatca ggctatgcag   1320
cggatcaaaa aagcacacaa aatgccatta acgggattac aaacaaggtg aacactgtta   1380
tcgagaaaat gaacattcaa ttcacagctg tgggtaaaga attcaacaaa ttagaaaaaa   1440
ggatggaaaa tttaaataaa aaagttgatg atggatttct ggacatttgg acatataatg   1500
cagaattgtt agttctactg gaaaatgaaa ggactctgga tttccatgac tcaaatgtga   1560
agaatctgta tgagaaagta aaaagccaat taaagaataa tgccaaagaa atcggaaatg   1620
gatgttttga gttctaccac aagtgtgaca atgaatgcat ggaaagtgta agaaatggga   1680
cttatgatta tcccaaatat tcagaagagt caaagttgaa cagggaaaag gtagatggag   1740
tgaaattgga atcaatgggg atctatcaga ttctggcgat ctactcaact gtcgcttcca   1800
gcttagtatt gctagttagt ttaggagcga tttccttttg gatgtgcagc aacgggagcc   1860
tacaatgtcg gatttgtatt tgagtttaaa ctgagctaac agggctagac tgtatgaggc   1920
cgtgcttctg ggttgaatta atcagggac gacctaaaga aaaacaatc tggactagtg    1980
cgagcagcat ttcttttgt ggcgtgaata tgatactgt agattggtct tggccagacg    2040
gtgctgagtt gccattcagc attgacaagt agtctgttca aaaaactcct tgtttctact   2100
```

<210> SEQ ID NO 50
<211> LENGTH: 2160
<212> TYPE: DNA
<213> ORGANISM: Artificial Sequence
<220> FEATURE:
<223> OTHER INFORMATION: Synthetic: Malaysia 04 HA in Segment 6

<400> SEQUENCE: 50

```
agcgaaagca ggggtttaaa ttgaatccaa atcagaaaat aacaaccatt ggatcaatct     60
gtctggtagt cggactaatt agcctaatat tgcaaatagg gaatataatc tcaatttgga    120
```

```
ttagccattc aattcaaact ggaagtcaaa accatactgg aatttgcaac caagatatcg    180
ccaccatgaa ggcaataatt gtactactca tggtagtaac atctaatgca gatcgaatct    240
gcactgggat aacatcgtca aactcaccac atgttgtcaa aactgctact caaggggagg    300
tcaatgtgac tggtgtaata ccactgacaa caacacccac caaatctcat tttgcaaatc    360
tcaaaggaac agaaaccaga gggaaactat gcccaaaatg cctcaactgc acagatctgg    420
acgtggcctt gggcagacca aaatgcacgg ggaacatacc ctcggcaaga gtttcaatac    480
tccatgaagt cagacctgtt acatctgggt gctttcctat aatgcacgac agaacaaaaa    540
ttagacagct gcctaacctt ctcagaggat acgaacatat caggttatca actcataacg    600
ttatcaatgc agaaaatgca ccaggaggac cctacaaaat ggaacctcag ggtcttgcc     660 ctaacgttac caatggaaac ggattttttcg caacaatggc ttgggccgtc caaaaaacg     720 acaacaacaa aacagcaaca aattcattaa caatagaagt accatacatt tgtacagaag    780
gagaagacca aattaccgtt tgggggttcc actctgatag cgaaacccaa atggcaaagc    840
tctatgggga ctcaaagccc cagaagttca cctcatctgc aacggagtg accacacatt     900 acgtttcaca gattggtggc ttcccaaatc aaacagaaga cggaggacta ccacaaagtg    960
gtagaattgt tgttgattac atggtgcaaa atctgggaa acaggaaca attacctatc      1020 aaagaggtat tttattgcct caaaaagtgt ggtgcgcaag tggcaggagc aaggtaataa    1080
aaggatcctt gcctttaatt ggagaagcag attgcctcca cgaaaaatac ggtggattaa    1140
acaaaagcaa gccttactac acaggggaac atgcaaaggc cataggaaat tgcccaatat    1200
gggtgaaaac acccttgaag ctggccaatg gaaccaaata tagacctcct gcaaaactat    1260
taaaggaaag gggtttcttc ggagctattg ctggtttctt agaaggagga tgggaaggaa    1320
tgattgcagg ttggcacgga tacacatccc atggggcaca tggagtagcg gtggcagcag    1380
accttaagag cactcaagag gccataaaca agataacaaa aaatctcaac tctttgagtg    1440
agctggaagt aaagaatctt caaagactaa gcggtgccat ggatgaactc cacaacgaaa    1500
tactagaact agacgagaaa gtggatgatc tcagagctga taataagc tcacaaatag       1560 aactcgcagt cctgctttcc aatgaaggaa taataaacag tgaagatgag catctcttgg    1620
cgcttgaaag aaagctgaag aaaatgctgg gcccctctgc tgtagagata gggaatggat    1680
gctttgaaac caaacacaag tgcaaccaga cctgtctcga cagaatagct gctggtacct    1740
ttgatgcagg agaattttct ctccccactt tgattcact gaatattact gctgcatctt      1800
taaatgacga tggattggat aatcatacta tactgctta ctactcaact gctgcctcca     1860
gtttggctgt aacattgatg atagctatct tgttgttta tatggtctcc agagacaatg     1920
tttcttgctc catctgtcta taagtttaaa ctgagctaac agggctagac tgtatgaggc     1980
cgtgcttctg ggttgaatta atcaggggac gacctaaaga aaaacaatc tggactagtg      2040 cgagcagcat ttcttttttgt ggcgtgaata gtgatactgt agattggtct tggccagacg    2100
gtgctgagtt gccattcagc attgacaagt agtctgttca aaaaactcct tgtttctact    2160
```

<210> SEQ ID NO 51
<211> LENGTH: 2154
<212> TYPE: DNA
<213> ORGANISM: Artificial Sequence
<220> FEATURE:
<223> OTHER INFORMATION: Synthetic: Yamagata 88 HA in Segment 6

<400> SEQUENCE: 51

```
agcgaaagca ggggtttaaa ttgaatccaa atcagaaaat aacaaccatt ggatcaatct    60
gtctggtagt cggactaatt agcctaatat tgcaaatagg gaatataatc tcaatttgga   120
ttagccattc aattcaaact ggaagtcaaa accatactgg aatttgcaac caagatatcg   180
ccaccatgaa ggcaataatt gtactactca tggtagtaac atccaacgca gatcgaatct   240
gcactgggat aacatcttca aactcacctc atgtggtcaa acagctact caaggggaag   300
ttaatgtgac tggtgtgata ccactgacaa caacaccaac aaaatctcat tttgcaaatc   360
tcaaaggaac aaagaccaga gggaaactat gcccaaactg tctcaactgc acagatctgg   420
atgtggcctt gggcagacca atgtgtatgg ggaccatacc ttcggcaaaa gcttcaatac   480
tccacgaagt cagacctgtt acatccgggt gctttcctat aatgcacgac agaacaaaaa   540
tcagacagct acccaatctt ctcagaggat atgaaaatat cagattatca acccataacg   600
ttatcaacgc agaaagggca ccaggaggac cctacagact tggaacctca gaatcttgcc   660
ctaacgttac cagtagaaac ggattcttcg caacaatggc ttgggctgtc caagggaca   720
acaaaacagc aacgaatcca ctaacagtag aagtaccata catttgcaca aaggagaag   780
accaaattac tgtttggggg ttccattctg ataacaaaaa ccaaatgaaa aacctctatg   840
gagactcaaa tcctcaaaag ttcacctcat ctgccaatgg agtaaccaca cattatgttt   900
ctcagattgg tgacttccca aatcaaacag aagacggagg gctaccacaa gcggcagaa    960
ttgttgttga ttacatggtg caaaaacctg gaaaacagg aacaattgtc tatcaaagag  1020
gtgttttgtt gcctcaaaag gtgtggtgcg caagtggcag gagcaaggta taaaagggt  1080
ccttgccttt aattggtgaa gcagattgcc ttcacgaaaa atacggtgga ttaaacaaaa  1140
gcaagcctta ctacacagga gaacatgcaa agccatagg aaattgccca atatgggtga  1200
aaacaccttt gaagcttgcc aatggaacca aatatagacc tcctgcaaaa ctattaaagg  1260
aaaggggttt cttcggagct attgctggtt tcttagaggg aggatgggaa ggaatgattg  1320
caggttggca cggatacaca tctcatggag cacatggagt ggcagtggca gcagaccta  1380
agagcacgca agaagccata aacaagataa caaaaatct caattctttg agtgagctag  1440
aagtaaagaa tcttcaaaga ctaagtggtg ccatggatga actccacaac gaaatactcg  1500
agctggatga gaaagtggat gatctcagag ctgacacaat aagctcgcaa atagagcttg  1560
cagtcttgct ttccaacgaa ggaataataa acagtgaaga tgagcatcta ttggcacttg  1620
agagaaaact aaagaaaatg ctgggtccct ctgctgtaga cataggaat ggatgcttcg  1680
aaaccaaaca caagtgcaac cagacctgct tagacaggat agctgctggc acctttaatg  1740
caggagaatt ttctcttccc acttttgatt cactgaatat tactgctgca tctttaaatg  1800
atgatggatt ggataatcat actatactgc tctactactc aactgctgct tctagtttgg  1860
ccgtaacatt gatgatagct attttttattg tttatatggt ctccagagac aatgtttctt  1920
gctccatctg tctataagtt taaactgagc taacagggct agactgtatg aggccgtgct  1980
tctgggttga attaatcagg ggacgaccta agaaaaaac aatctggact agtgcgagca  2040
gcatttcttt ttgtggcgtg aatagtgata ctgtagattg gtcttggcca gacggtgctg  2100
agttgccatt cagcattgac aagtagtctg ttcaaaaaac tccttgtttc tact         2154
```

<210> SEQ ID NO 52
<211> LENGTH: 2103
<212> TYPE: DNA
<213> ORGANISM: Artificial Sequence
<220> FEATURE:
<223> OTHER INFORMATION: Synthetic: Fujian 2002 HA in Segment 6

<400> SEQUENCE: 52

```
agcgaaagca ggggtttaaa ttgaatccaa atcagaaaat aacaaccatt ggatcaatct      60
gtctggtagt cggactaatt agcctaatat tgcaaatagg gaatataatc tcaatttgga     120
ttagccattc aattcaaact ggaagtcaaa accatactgg aatttgcaac caagatatcg     180
ccaccatgaa gaccatcata gcactgtcat atatactttg cctcgtgttc gcccagaaac     240
ttcccggaaa tgacaacagc acggcaacgc tgtgccttgg caccatgca gtaccaaacg      300
gaacgatagt gaaaacaatc acgaatgacc aaattgaagt tactaatgct actgagctgg     360
ttcagagttc ctcaacaggt ggaatatgcg acagtcctca tcagatcctt gatggagaaa     420
actgcacact aatagatgct ctattgggag accctcagtg tgatggcttc caaaataaga     480
aatgggacct ttttgttgaa cgcagcaaag cctacagcaa ctgttaccct tatgatgtgc     540
cggattatgc ctcccttagg tcactagttg cctcatccgg tacactggag tttaacaatg     600
aaagcttcaa ttggactgga gtcactcaga atggaacaag ctctgcttgc aaaaggagat     660
ctaataaaag tttctttagt agattgaatt ggttgaccca tttaaaatac aaatacccag     720
cattgaacgt gactatgcca aacaatgaaa aatttgacaa attgtacatt tgggggttc      780
tccacccggg tacggacagt gaccaaatca gcctatatgc tcaagcatca ggaagaatca     840
cagtctctac caaagaagc caacaaactg taatcccgaa tatcggatct agacccaggg      900
taagggtgt ctccagcaga ataagcatct attggacaat agtaaaaccg ggagacatac       960
ttttgattaa cagcacaggg aatctaattg ctcctagggg ttacttcaaa atacgaagtg    1020
ggaaaagctc aataatgaga tcagatgcac ccattggcaa atgcaattct gaatgcatca    1080
ctccaaatgg aagcattccc aatgacaaac catttcaaaa tgtaaacagg atcacatatg    1140
gggcctgtcc cagatatatt aagcaaaaca ctctgaaatt ggcaacaggg atgcgaaatg    1200
taccagagaa acaaactaga ggcatatttg gcgcaatcgc gggtttcata gaaaatggtt    1260
gggagggaat ggtggacggt tggtacggtt tcaggcatca aaattctgag ggcacaggac    1320
aagcagcaga tctcaaaagc actcaagcag caatcaacca aatcaatggg aaactgaata    1380
ggttaatcgg gaaaacaaac gagaaattcc atcagattga aaaagaattc tcagaagtag    1440
aagggagaat tcaggacctc gagaaatatg ttgaggacac taaaatagat ctctggtcat    1500
acaacgcgga gcttcttgtt gccctggaga ccaacatac aattgatcta actgactcag     1560
aaatgaacaa actgtttgaa agaacaaaga gcaactgag ggaaaatgct gaggatatgg      1620
gcaatggttg tttcaaaata taccacaaat gtgacaatgc ctgcatagg tcaatcagaa      1680
atggaactta tgaccatgat gtatacagag atgaagcatt aaacaaccgg ttccagatca    1740
aaggtgttga gctgaagtca ggatacaaag attggatcct atggatttcc tttgccatct    1800
cctgttttct actctgtgtg gctctgctgg gttttattat gtgggcatgt cagaagggca    1860
atatacggtg taatatttgc atctgagttt aaactgagct aacagggcta gactgtatga    1920
ggccgtgctt ctgggttgaa ttaatcaggg gacgacctaa agaaaaaaca atctggacta    1980
gtgcgagcag catttctttt tgtggcgtga atagtgatac tgtagattgg tcttggccag    2040
acggtgctga gttgccattc agcattgaca agtagtctgt tcaaaaaact ccttgtttct    2100
act                                                                   2103
```

<210> SEQ ID NO 53
<211> LENGTH: 2103
<212> TYPE: DNA

<213> ORGANISM: Artificial Sequence
<220> FEATURE:
<223> OTHER INFORMATION: Synthetic: Victoria 2009 HA in Segment 6

<400> SEQUENCE: 53

| | |
|---|---:|
| agcgaaagca ggggtttaaa ttgaatccaa atcagaaaat aacaaccatt ggatcaatct | 60 |
| gtctggtagt cggactaatt agcctaatat tgcaaatagg gaatataatc tcaatttgga | 120 |
| ttagccattc aattcaaact ggaagtcaaa accatactgg aatttgcaac caagatatcg | 180 |
| ccaccatgaa acaattatc gctctttcat acattctttg cctcgtcttc gctcaaaaac | 240 |
| ttcccggaaa tgacaacagc acggcaacgc tgtgccttgg gcaccatgca gtaccaaacg | 300 |
| gaacgatagt gaaaacaatc acgaatgacc aaattgaagt tactaatgct actgagctgg | 360 |
| ttcagaattc ctcaacaggt gaaatatgcg acagtcctca tcagatcctt gatggaaaaa | 420 |
| actgcacact aatagatgct ctattgggag accctcagtg tgatggcttc caaaataaga | 480 |
| aatgggacct ttttgttgaa cgcagcaaag cctacagcaa ctgttaccct tatgatgtgc | 540 |
| cggattatgc ctcccttagg tcactagttg cctcatccgg cacactggag tttaacaatg | 600 |
| aaagcttcaa ttggactgga gtcactcaaa acggaacaag ctctgcttgc ataaggagat | 660 |
| ctaaaaacag tttctttagt agattgaatt ggttgactaa cttaaacttc aaatacccag | 720 |
| cattgaacgt gactatgccg aacaatgaac aatttgacaa attgtacatt tgggggggttc | 780 |
| accacccggt tacggacaaa gaccaaatct tcctgtatgc tcaagcatca ggaagaatca | 840 |
| cagtctctac caaaagaagc caacaaactg taatcccgaa tatcggatct agaccccgag | 900 |
| taaggaatat ccctagcaga ataagcatct attggacaat agtaaaaccg ggagacatac | 960 |
| ttttgattaa cagcacaggg aatctaattg ctcctagggg ttacttcaaa atgcaaagtg | 1020 |
| ggaaaagctc aataatgaga tcagatgcac ccattggcaa atgcaattct gaatgcatca | 1080 |
| ctccaaatgg aagcattccc aatgacaaac cattccaaaa tgtaaacagg atcacatacg | 1140 |
| gggcctgtcc cagatatgtt aagcaaaaca ctctgaaatt ggcaacaggg atgcgaaatg | 1200 |
| taccagagaa acaaactaga ggcatatttg gcgcaatcgc gggtttcata gaaaatggtt | 1260 |
| gggagggaat ggtggatggt tggtacggtt tcaggcatca aaattctgag ggaagaggac | 1320 |
| aagcagcaga tctcaaaagc actcaagcag caatcgatca aatcaatggg aagctgaata | 1380 |
| gattgatcgg gaaaaccaac gagaaattcc atcagattga aaagaattc tcagaagtcg | 1440 |
| aagggagaat tcaggacctt gagaaatatg ttgaggacac taaaatagat ctctggtcat | 1500 |
| acaacgcgga gcttcttgtt gccctggaga accaacatac aattgatcta actgactcag | 1560 |
| aaatgaacaa actgtttgaa aaacaaaga agcaactgag ggaaaatgct gaggatatgg | 1620 |
| gcaatggttg tttcaaaata aaccacaaat gtgacaatgc ctgcatagga tcaatcagaa | 1680 |
| atggaactta tgaccacaat gtatacagag atgaagcatt aaacaaccgg tttcagatca | 1740 |
| agggagttga gctgaagtca gggtacaaag attggatcct atggatttca tttgctatat | 1800 |
| cgtgctttct actatgcgta gcactcctcg ggtttattat gtgggcctgc caaaaggaa | 1860 |
| atattagatg caacatctgt atttgagttt aaactgagct aacagggcta gactgtatga | 1920 |
| ggccgtgctt ctgggttgaa ttaatcaggg acgacctaa agaaaaaaca atctggacta | 1980 |
| gtgcgagcag catttctttt tgtggcgtga atagtgtatac tgtagattgg tcttggccag | 2040 |
| acggtgctga gttgccattc agcattgaca agtagtctgt tcaaaaaact ccttgtttct | 2100 |
| act | 2103 |

<210> SEQ ID NO 54
<211> LENGTH: 2760
<212> TYPE: DNA
<213> ORGANISM: Artificial Sequence
<220> FEATURE:
<223> OTHER INFORMATION: Synthetic: Transmembrane ZsGreen In Segment 4 with the HA Protein

<400> SEQUENCE: 54

| | | | | | |
|---|---|---|---|---|---|
| agcaaaagca | ggggaaaata | aaaacaacca | aattgaaggc | aaacctactg | gtcctgttaa | 60 |
| gtgcacttgc | agctgcagtt | gcagacacaa | tttgtatagg | ccaccatgaa | tccaaatcag | 120 |
| aaaatcacca | caattggatc | catttgtctg | gtggtcggtc | tcatcagtct | cattcttcaa | 180 |
| attgggaaca | tcatttcaat | ttggatcagc | cattctatac | aaacgatggc | tcaaagcaag | 240 |
| catggactca | ctaaagaaat | gactatgaag | tacagaatgg | aaggatgtgt | ggatggccat | 300 |
| aagtttgtaa | ttactggaga | aggcattgga | tacccctta | aaggaaaaca | agcaattaac | 360 |
| ctgtgtgtcg | tagagggagg | gcctctccca | tttgctgagg | atatactcag | tgcagcgttt | 420 |
| atgtatggca | atagagtctt | tacagagtat | ccacaggaca | ttgttgatta | tttcaagaac | 480 |
| tcatgccccg | ccggttacac | atgggacaga | tcctttcttt | tcgaagatgg | agcagtttgt | 540 |
| atttgtaacg | cggatattac | ggttagtgtt | gaagaaaatt | gcatgtatca | tgagtccaaa | 600 |
| ttttatggag | tcaatttccc | cgcagatgga | ccagtcatga | agaagatgac | agataactgg | 660 |
| gaacccagct | gtgagaaaat | aataccggta | ccaaaacaag | gcatactcaa | aggtgatgtg | 720 |
| tcaatgtatt | tacttctcaa | agacggtgga | cgtttacgct | gccagtttga | cacagtgtat | 780 |
| aaggctaaat | ctgtccccag | gaaaatgcca | gattggcact | ttattcaaca | caagcttact | 840 |
| cgggaggaca | ggtctgatgc | aaagaatcag | aaatggcatc | ttacagaaca | tgctattgcc | 900 |
| agtggtagtg | ctctccctgg | cagtggggac | tataaggacg | atgatgacaa | aggaagcggt | 960 |
| gctactaatt | tttcacttct | caaacaagca | ggcgatgtgg | aagaaaaccc | cggaccaatg | 1020 |
| aaagcgaatt | gtgtagtttt | actgtccgcg | ttggcggccg | cggacgcaga | cacaatatgt | 1080 |
| ataggctacc | atgcgaacaa | ttcaaccgac | actgttgaca | cagtactcga | gaagaatgtg | 1140 |
| acagtgacac | actctgttaa | cctgctcgaa | gacagccaca | acggaaaact | atgtagatta | 1200 |
| aaaggaatag | ccccactaca | attggggaaa | tgtaacatcg | ccggatggct | cttgggaaac | 1260 |
| ccagaatgcg | acccactgct | tccagtgaga | tcatggtcct | acattgtaga | aacaccaaac | 1320 |
| tctgagaatg | gaatatgtta | tccaggagat | ttcatcgact | atgaggagct | gagggagcaa | 1380 |
| ttgagctcag | tgtcatcatt | cgaaagattc | gaaatatttc | caaagaaag | ctcatggccc | 1440 |
| aaccacaaca | caaacggagt | aacggcagca | tgctcccatg | aggggaaaag | cagttttac | 1500 |
| agaaatttgc | tatggctgac | ggagaaggag | ggctcatacc | caaagctgaa | aaattcttat | 1560 |
| gtgaacaaaa | aagggaaaga | agtccttgta | ctgtgggta | ttcatcaccc | gcctaacagt | 1620 |
| aaggaacaac | agaatctcta | tcagaatgaa | aatgcttatg | tctctgtagt | gacttcaaat | 1680 |
| tataacagga | gatttacccc | ggaaatagca | gaaagaccca | agtaagaga | tcaagctggg | 1740 |
| aggatgaact | attactggac | cttgctaaaa | cccggagaca | caataatatt | tgaggcaaat | 1800 |
| ggaaatctaa | tagcaccaat | gtatgctttc | gcactgagta | gaggctttgg | gtccggcatc | 1860 |
| atcacctcaa | acgcatcaat | gcatgagtgt | aacacgaagt | gtcaaacacc | cctgggagct | 1920 |
| ataaacagca | gtctcccta | ccagaatata | cacccagtca | aataggaga | gtgcccaaaa | 1980 |
| tacgtcagga | gtgccaaatt | gaggatggtt | acaggactaa | ggaacactcc | gtccattcaa | 2040 |
| tccagaggtc | tatttggagc | cattgccggt | tttattgaag | gggatggac | tggaatgata | 2100 |

```
gatggatggt atggttatca tcatcagaat gaacagggat caggctatgc agcggatcaa    2160
aaaagcacac aaaatgccat taacgggatt acaaacaagg tgaacactgt tatcgagaaa    2220
atgaacattc aattcacagc tgtgggtaaa gaattcaaca attagaaaaa aggatggaa     2280 aatttaaata aaaagttga tgatggattt ctggacattt ggacatataa tgcagaattg     2340
ttagttctac tggaaaatga aaggactctg gatttccatg actcaaatgt gaagaatctg    2400
tatgagaaag taaaaagcca attaaagaat aatgccaaag aaatcggaaa tggatgtttt    2460
gagttctacc acaagtgtga caatgaatgc atggaaagtg taagaaatgg gacttatgat    2520
tatcccaaat attcagaaga gtcaaagttg aacaggaaa aggtagatgg agtgaaattg     2580
gaatcaatgg ggatctatca gattctggcg atctactcaa ctgtcgccag ttcactggtg    2640
cttttggtct ccctgggggc aatcagtttc tggatgtgtt ctaatggatc tttgcagtgc    2700
agaatatgca tctgagatta gaatttcaga atatatgagga aaaacaccct tgtttctact  2760
```

<210> SEQ ID NO 55
<211> LENGTH: 2031
<212> TYPE: DNA
<213> ORGANISM: Artificial Sequence
<220> FEATURE:
<223> OTHER INFORMATION: Synthetic: Zika Full Length E in Segment 6

<400> SEQUENCE: 55

```
agcgaaagca ggggtttaaa ttgaatccaa atcagaaaat aacaaccatt ggatcaatct      60
gtctggtagt cggactaatt agcctaatat tgcaaatagg gaatataatc tcaatttgga    120
ttagccattc aattcaaact ggaagtcaaa accatactgg aatttgcaac caagatatcg    180
ccaccatgaa tccgggtttc gcactagcag ccgcggcaat agcttggcta ctcgggtctt    240
ctacgtcgca aaaggtgata tacctcgtca tgatactgct catagcgcca gcctactcaa    300
ttcgatgtat aggtgtatca aaccgagatt tcgttgaagg aatgtccgga ggaacatggg    360
tggatgtggt gctagagcac ggagggtgtg tgactgtaat ggctcaggat aaacccacag    420
tggatataga actagtaacc actacagttt ctaacatggc agaagttaga agctattgct    480
atgaagcaag tattagcgat atggcctcgg attccaggtg tcccacacag ggagaggcat    540
acctggataa acagtcggat actcaatatg tgtgcaagag aacctagtc gatagaggat    600 ggggaacgg tgtgtggcctc ttcgggaaag gaagtcttgt tacatgtgca agtttgctt    660 gttctaagaa gatgactggg aagtcaattc aaccagaaaa tctcgaatat cgaattatgc    720
ttagcgtgca cgggagtcag cattcaggca tgatagtcaa tgcacaggc cacgaaacag    780 acgagaatag ggctaaggtt gagattactc ctaattctcc tagagcagag gctactcttg    840
gagggtttgg aagcttagga ttagactgcg agcccaggac tggattggat ttcagcgatc    900
tgtattacct gactatgaac aacaaacatt ggctagtgca taaagagtgg ttccacgata    960
taccactccc atggcatgca ggggcagaca ctggaacacc gcattggaat aataaggaag   1020
ctctggttga atttaaagac gcgcatgcaa aaaggcaaac agtcgttgtg ttaggttccc   1080
aggaaggggc tgttcatacg gctttggcag gagcactcga ggcagaaatg gatgggcta    1140 agggtcgctt gagttcaggc catcttaaat gccgactcaa aatggacaaa cttaggctga   1200
agggagtctc atatagcctc tgtactgccg catttaccttc accaaaaatt ccagcagaaa   1260
cattgcacgg aacagtgact gtcgaagttc aatatgcagg aacagatgga ccttgcaagg   1320
taccggcgca aatggccgtt gacatgcaga ctctaactcc agttgggaga cttattacag   1380
```

```
-continued caaatcctgt cataacagaa tccacagaga actcaaagat gatgcttgaa ctcgaccctc    1440
ccttcgggga ttcgtatatt gttatcggcg ttggtgaaaa aaaaattaca caccattggc    1500
atcggagcgg ctctaccatc ggcaaggcct ttgaagccac tgtgaggggc gcaaaaagaa    1560
tggctgtgct tggcgacaca gcgtgggact tcggttctgt aggaggcgca ctaaatagct    1620
tgggaaaagg aatacaccaa attttcggag cagcattcaa atctttgttt ggaggtatgt    1680
catggtttag tcaaatcctg ataggcactc tacttatgtg gctgggacta aatacaaaaa    1740
atggatccat tagtcttatg tgtttagcct taggaggtgt tttgattttc ttatctacag    1800
ctgtgtccgc ttaggtttaa actgagctaa cagggctaga ctgtatgagg ccgtgcttct    1860
gggttgaatt aatcagggga cgacctaaag aaaaaacaat ctggactagt gcgagcagca    1920
tttctttttg tggcgtgaat agtgatactg tagattggtc ttggccagac ggtgctgagt    1980
tgccattcag cattgacaag tagtctgttc aaaaaactcc ttgtttctac t             2031
```